(12) United States Patent
Takashima et al.

(10) Patent No.: US 7,411,685 B2
(45) Date of Patent: Aug. 12, 2008

(54) SPECTROMETRIC MEASURING INSTRUMENT

(75) Inventors: Jun Takashima, Nara (JP); Koichi Ekawa, Kyoto-fu (JP); Hideyuki Murai, Nara (JP)

(73) Assignee: Omron Corporation, Kyoto-Shi (JP)

( * ) Notice: Subject to any disclaimer, the term of this patent is extended or adjusted under 35 U.S.C. 154(b) by 281 days.

(21) Appl. No.: 11/288,447

(22) Filed: Nov. 29, 2005

(65) Prior Publication Data

US 2006/0114470 A1 Jun. 1, 2006

(30) Foreign Application Priority Data

Nov. 30, 2004 (JP) ............................. P2004-347709

(51) Int. Cl.
*G01B 11/02* (2006.01)

(52) U.S. Cl. ..................................................... 356/504

(58) Field of Classification Search ......... 356/364–370, 356/492, 504
See application file for complete search history.

(56) References Cited

U.S. PATENT DOCUMENTS

| | | | |
|---|---|---|---|
| 5,872,630 A | 2/1999 | Johs et al. | |
| 6,137,575 A * | 10/2000 | Sugiyama et al. | ........... 356/503 |
| 6,320,657 B1 * | 11/2001 | Aspnes et al. | ............... 356/369 |
| 6,982,792 B1 | 1/2006 | Woollam et al. | |
| 2004/0075836 A1 | 4/2004 | Horie et al. | |

FOREIGN PATENT DOCUMENTS

| EP | 1 034 413 | 9/2000 |
|---|---|---|
| JP | 06-288835 A | 10/1994 |
| JP | 2004-138519 | 5/2004 |
| WO | WO 99/08068 | 2/1999 |

* cited by examiner

*Primary Examiner*—Tarifur R Chowdhury
*Assistant Examiner*—Jonathon D Cook
(74) *Attorney, Agent, or Firm*—Foley & Lardner LLP

(57) ABSTRACT

Providing a spectrometric measuring instrument suitable for in-line measurement for example in a semiconductor manufacturing process, an FPD manufacturing process, or the like, by realizing size reduction and imparting resistance to distance fluttering, angle fluttering in a horizontal direction, and angle fluttering in a perpendicular direction. A light interference type spectral element for gradually changing a wavelength of transmitted light by means of a transmitted position is provided immediately before the photoelectric transfer part array device, and based upon a light-receiving side optical system having the function of detecting a change in state of polarization of a reflected light from a sample, and a series of light-receiving amount data obtained from each of photoelectric transfer parts of the photoelectric transfer part array device, polarized light is analyzed. By fitting of a measured waveform to a theoretical waveform, a film thickness or film quality is obtained.

22 Claims, 52 Drawing Sheets

A View seen from front

B View seen from top

Fig. 2
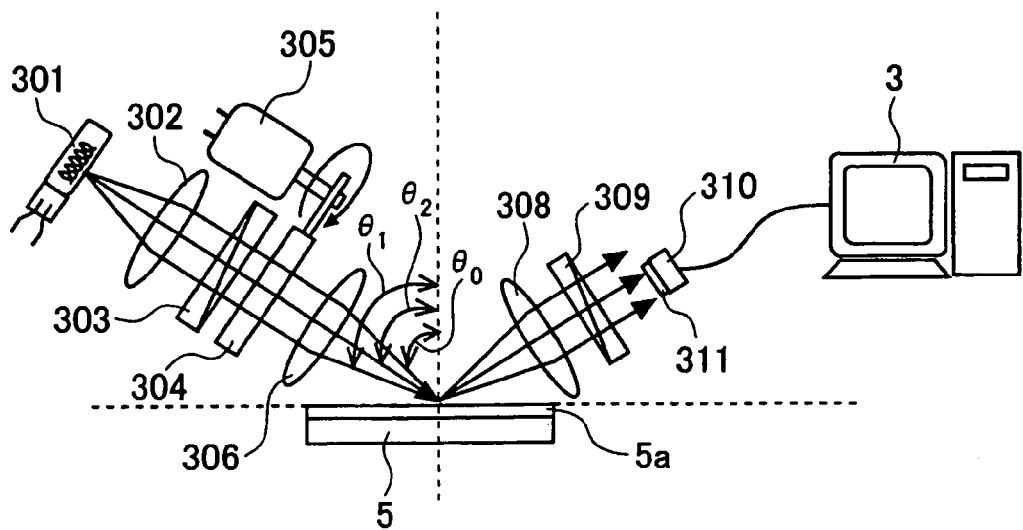
A  View seen from front
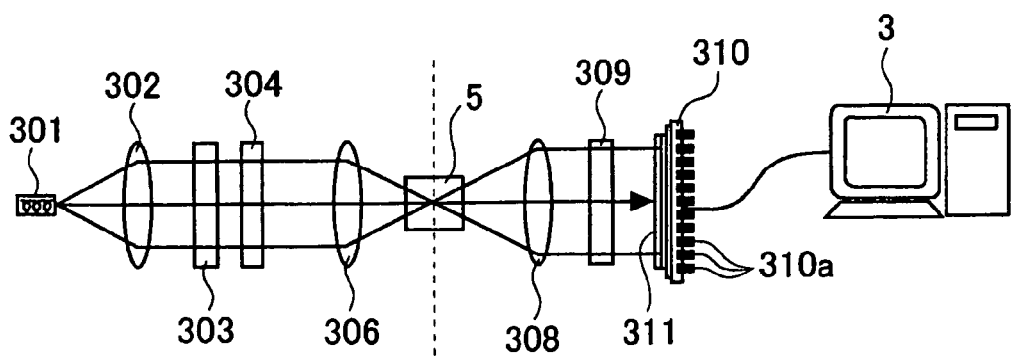
B  View seen from top r: Complex reflectance of opaque substrate in the absence of rear face reflection A   Optical model of single-layered film $$R_{all} = r + tr't + tr'rr't + tr'rr'rtr' + \cdots$$
$$= r + tr't\left[1 + rr' + (rr')^2 + \cdots\right]$$
$$= r + tr't\left[\frac{1}{1-rr'}\right] = r + \frac{t^2 r'}{1-rr'}$$
$$= r + \frac{(1-r)^2 r'}{1-rr'}$$

B   Arithmetic expression for guiding reflected light ($R_{all}$)

Fig. 8

| Wavelength / Film thickness | λp | λp+Δλ | λp+2Δλ | ... | ... | λq |
|---|---|---|---|---|---|---|
| Dx | Ψdx(λp) | Ψdx(λp+Δλ) | | | | Ψdx(λq) |
| dx+Δd | Ψdx+Δd(λp) | Ψdx+Δd(λp+Δλ) | | | | Ψdx+Δd(λq) |
| ... | | | | | | |
| dy | Ψdy(λp) | Ψdy(λp+Δλ) | | | | Ψdy(λq) |
| ... | | | | | | |
| dz | Ψdz(λp) | Ψdz(λp+Δλ) | | | | Ψdz(λq) |

Fig. 9

| Film thickness \ Wavelength | $\lambda p$ | $\lambda p+\Delta\lambda$ | $\lambda p+\Delta\lambda$ | ... | ... | $\lambda q$ |
|---|---|---|---|---|---|---|
| Dx | $\Delta dx(\lambda p)$ | $\Delta dx(\lambda p+\Delta\lambda)$ | | | | $\Delta dx(\lambda q)$ |
| $dx+\Delta d$ | $\Delta dx+\Delta d(\lambda p)$ | $\Delta dx+\Delta d(\lambda p+\Delta\lambda)$ | | | | $\Delta dx+\Delta d(\lambda q)$ |
| : | | | | | | |
| dy | $\Delta dy(\lambda p)$ | $\Delta dy(\lambda p+\Delta\lambda)$ | | | | $\Delta dy(\lambda q)$ |
| : | | | | | | |
| dz | $\Delta dz(\lambda p)$ | $\Delta dz(\lambda p+\Delta\lambda)$ | | | | $\Delta dz(\lambda q)$ |

Distance from target wavelength α

Fig. 16
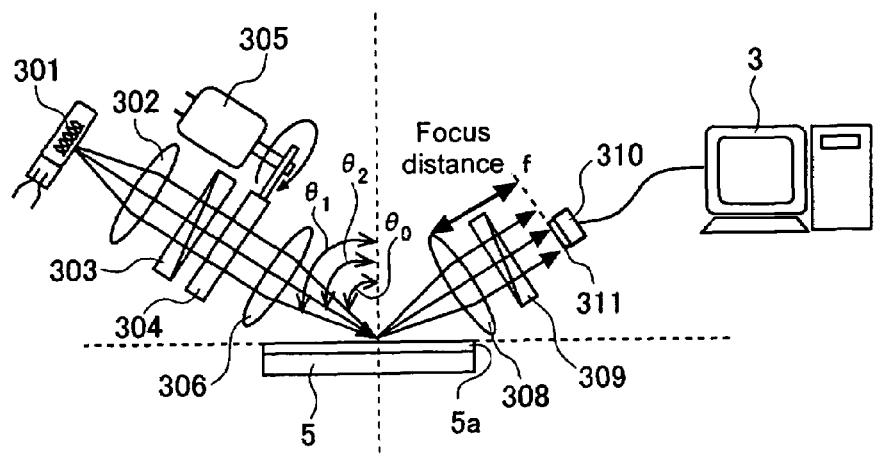
A  View seen from front
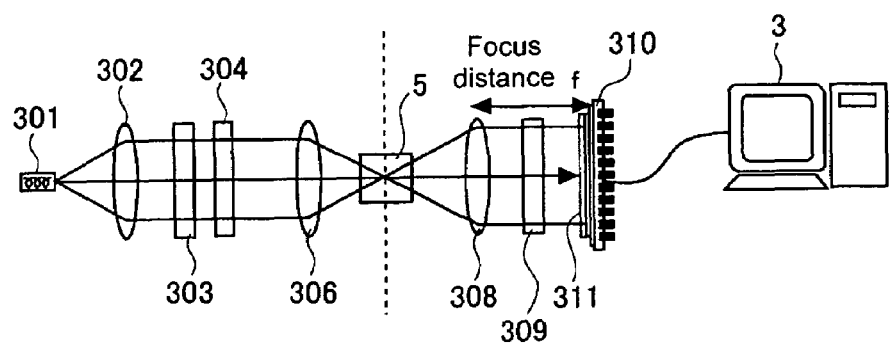
B  View seen from top

Fig. 28
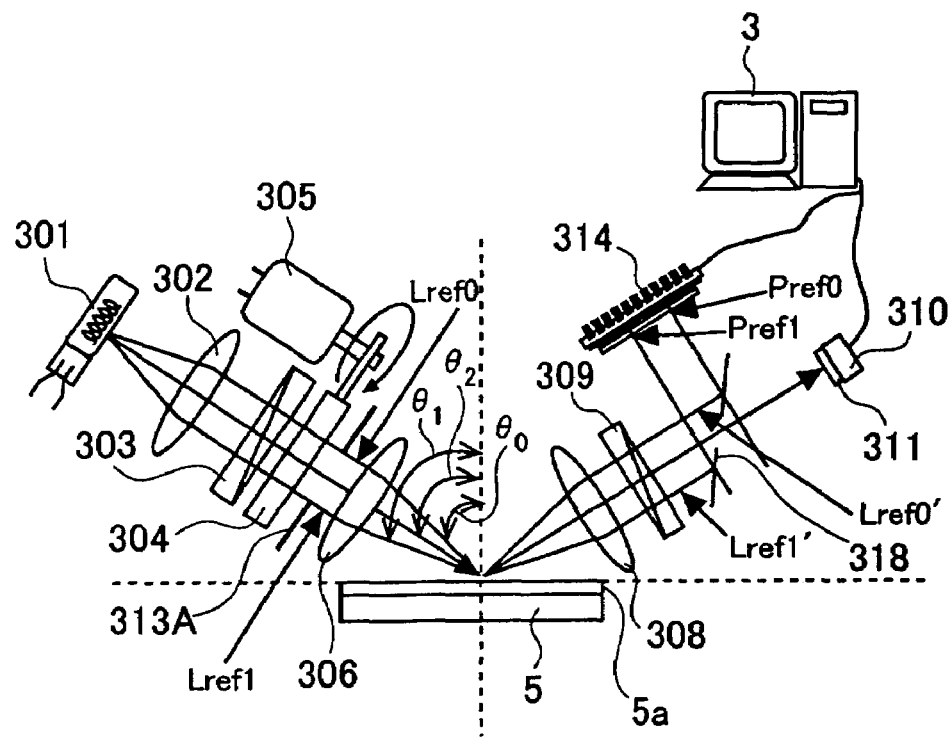
A  View seen from front
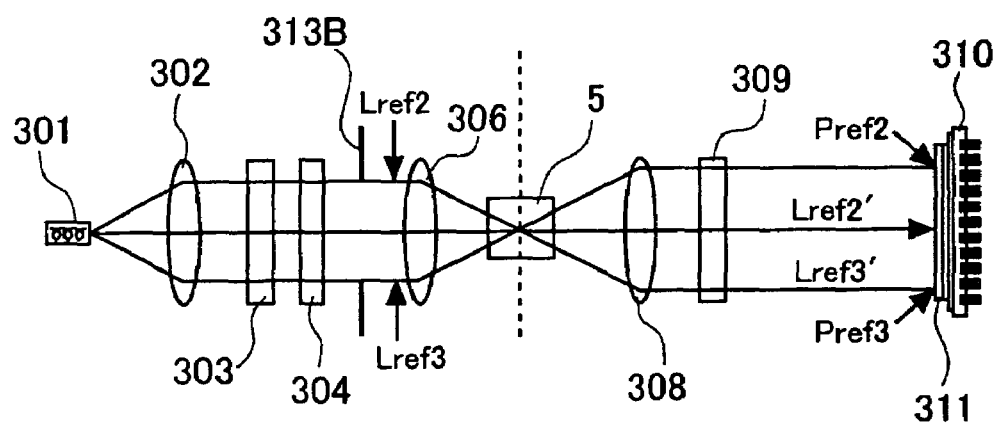
B  View seen from top

Fig. 29
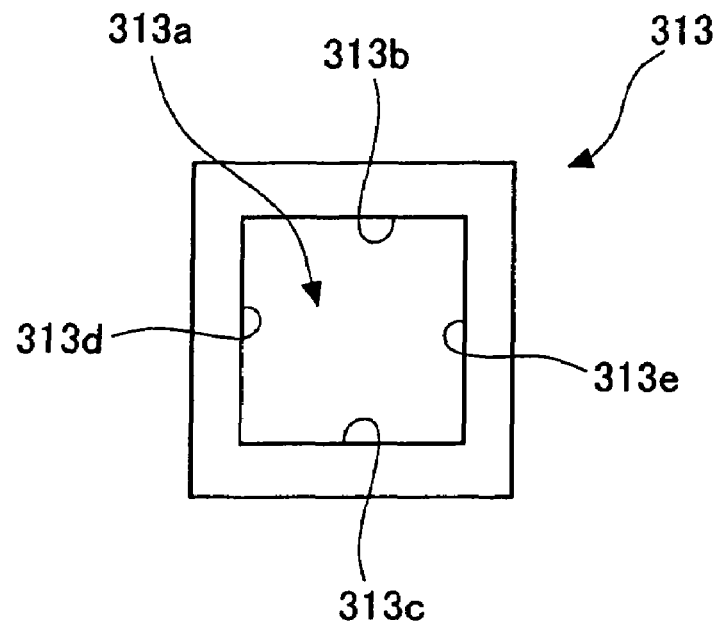
A
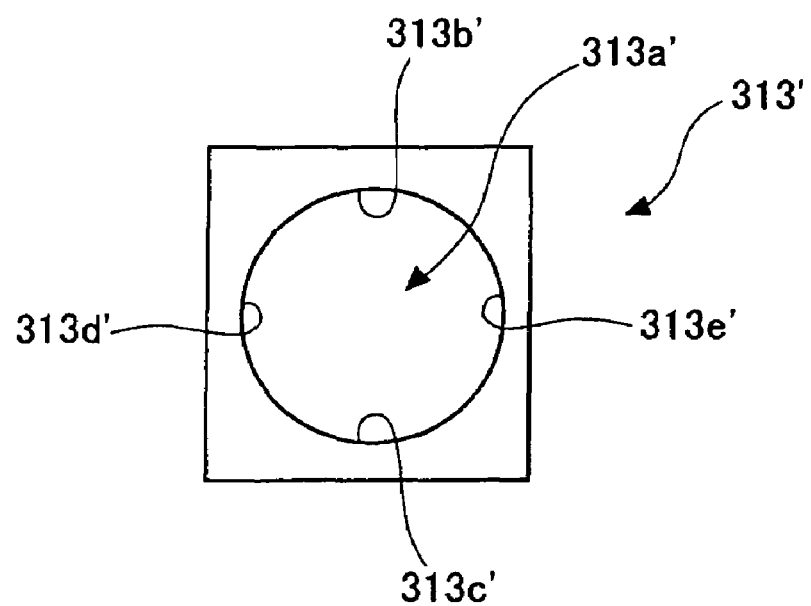
B

Fig. 30
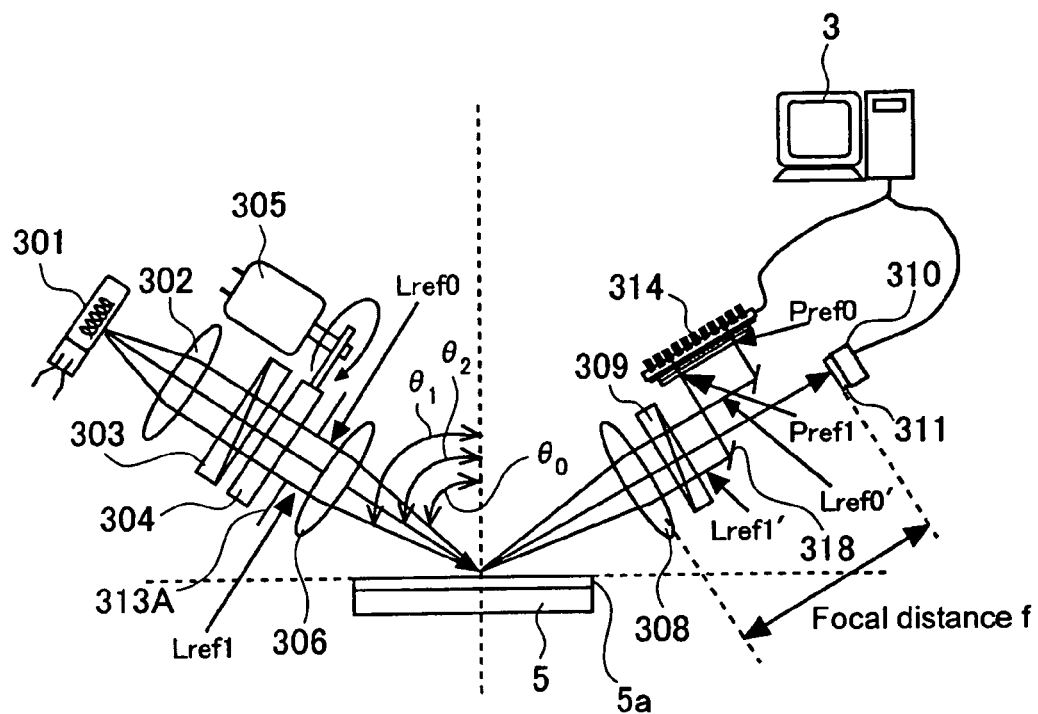
A  View seen from front
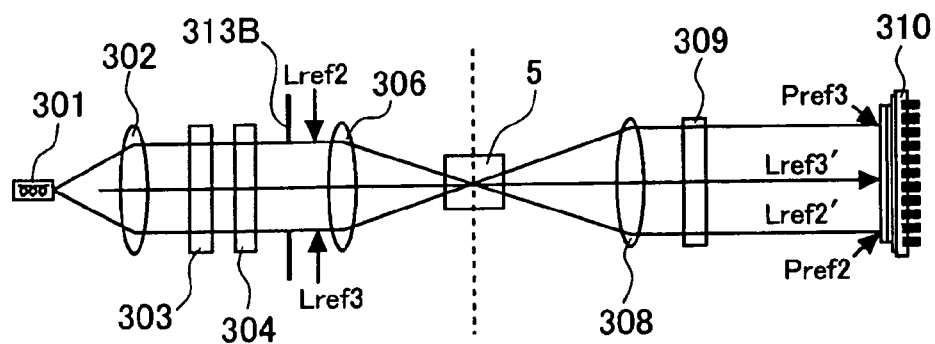
B  View seen from top

Fig. 35

| Film thickness \ Wavelength | $\lambda p$ | $\lambda p+\Delta\lambda$ | $\lambda p+2\Delta\lambda$ | ... | ... | $\lambda q$ |
|---|---|---|---|---|---|---|
| Dx | $Rdx(\lambda p)$ | $Rdx(\lambda p+\Delta\lambda)$ | | | | $Rdx(\lambda q)$ |
| $dx+\Delta d$ | $Rdx+\Delta d(\lambda p)$ | $Rdx+\Delta d(\lambda p+\Delta\lambda)$ | | | | $Rdx+\Delta d(\lambda q)$ |
| : | | | | | | |
| dy | $Rdy(\lambda p)$ | $Rdy(\lambda p+\Delta\lambda)$ | | | | $Rdy(\lambda q)$ |
| : | | | | | | |
| dz | $Rdz(\lambda p)$ | $Rdz(\lambda p+\Delta\lambda)$ | | | | $Rdz(\lambda q)$ |

| Incident angle | θ1 | θ1 | θ1 | ... | θ1 |
|---|---|---|---|---|---|
| Wavelength | λ1 | λ2 | λ3 | ... | λn |
| | Ccd θ1λ1 | Ccd θ2λ2 | Ccd θ3λ3 | ... | Ccd θnλn |

B

| Incident angle / Wavelength | θ1 | θ2 | θ3 | ... | θn |
|---|---|---|---|---|---|
| λ1 | Ccd θ1λ1 | Ccd θ2λ1 | Ccd θ3λ1 | ... | Ccd θnλ1 |
| λ2 | Ccd θ1λ2 | Ccd θ2λ2 | Ccd θ3λ2 | ... | Ccd θnλ2 |
| λ3 | Ccd θ1λ3 | Ccd θ2λ3 | Ccd θ3λ3 | ... | Ccd θnλ3 |
| ... | ... | ... | ... | ... | ... |
| λm | Ccd θ1λm | Ccd θ2λm | Ccd θ3λm | ... | Ccd θnλm |

Fig. 44
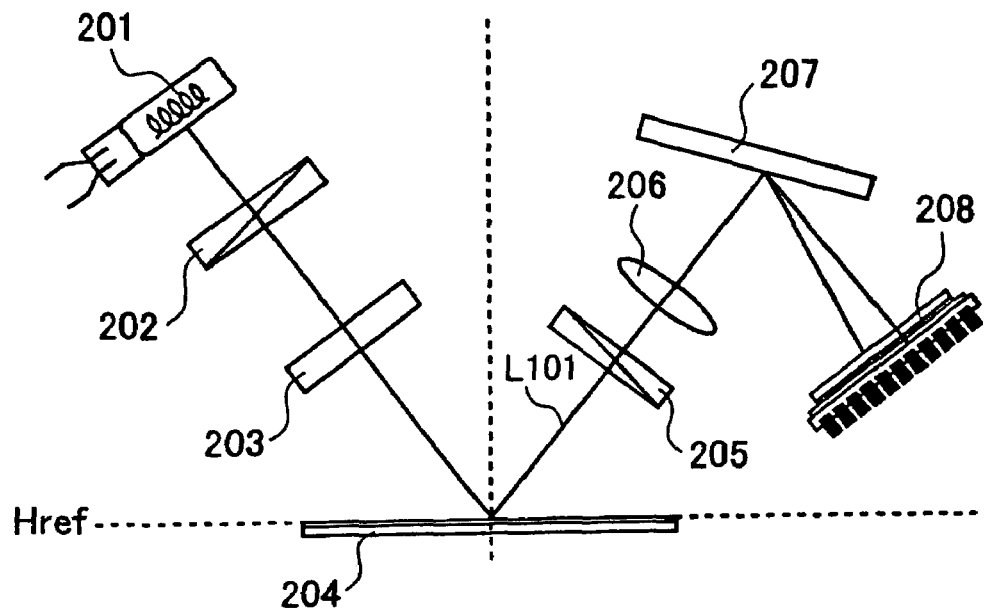
A  Positional relation between optical system and sample (reference height)
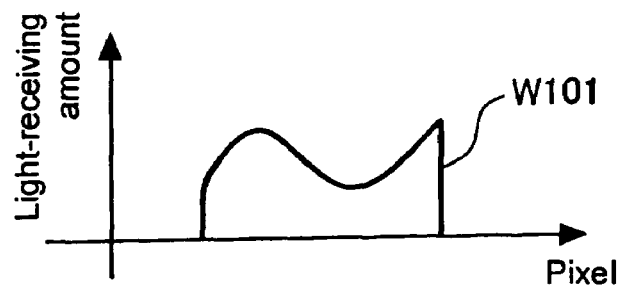
B  Reflected light intensity distribution waveform
PRIOR ART

Fig. 45
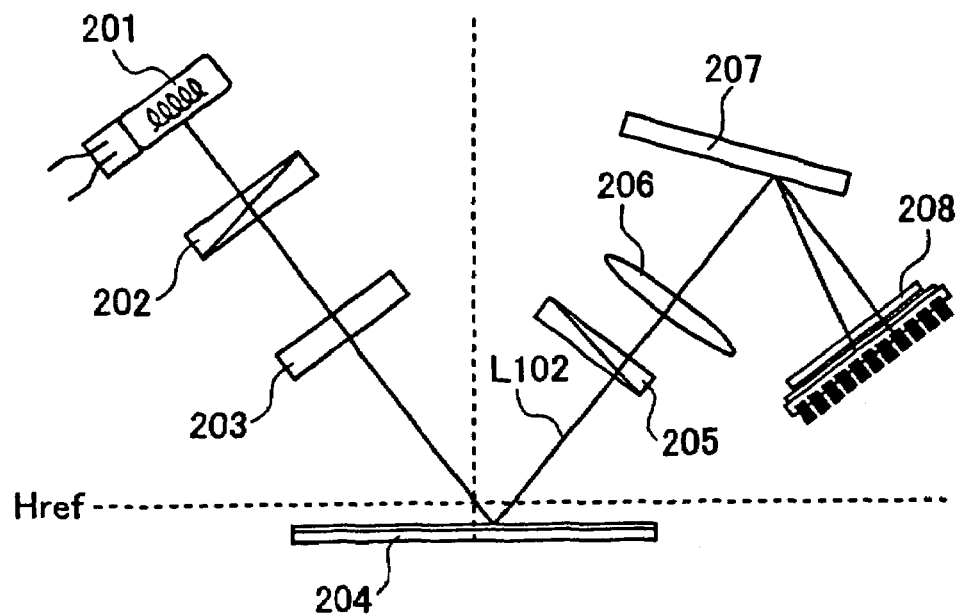
A  Positional relation between optical system and sample (lowered height)
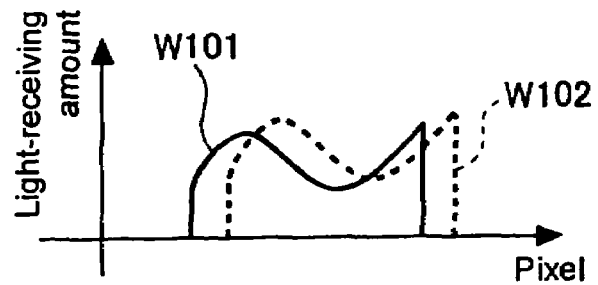
B  Reflected light intensity distribution waveform
PRIOR ART

Fig. 46
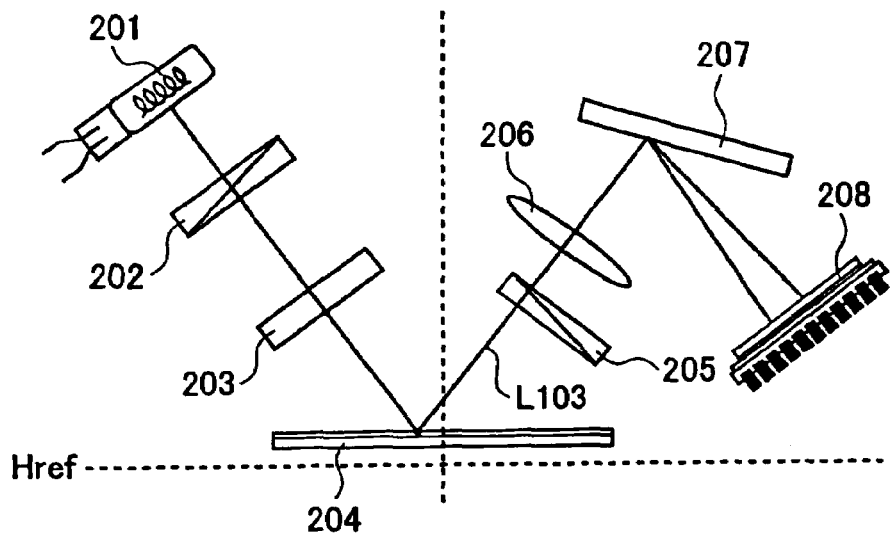
A  Positional relation between optical system and sample (raised height)
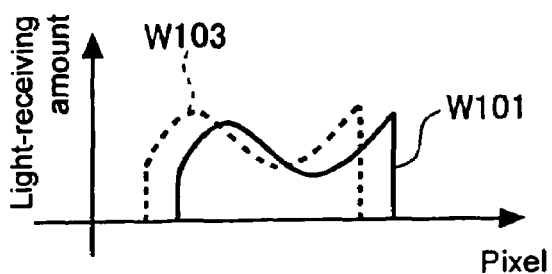
B  Reflected light intensity distribution waveform
PRIOR ART

Fig. 47
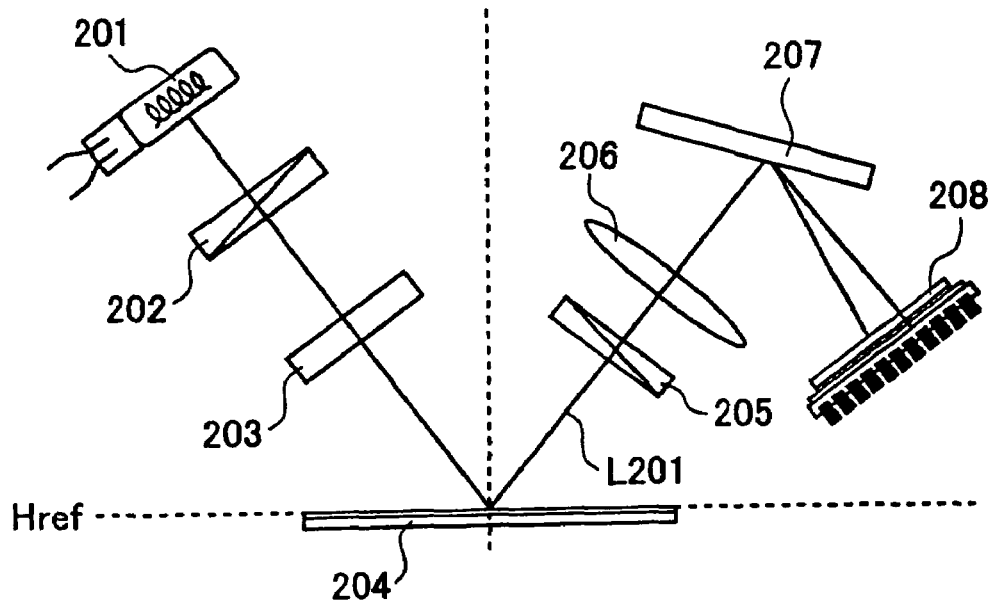
A  Positional relation between optical system and sample (reference angle)
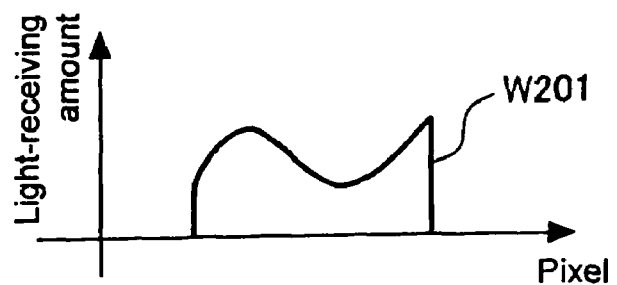
B  Reflected light intensity distribution waveform
PRIOR ART

Fig. 48
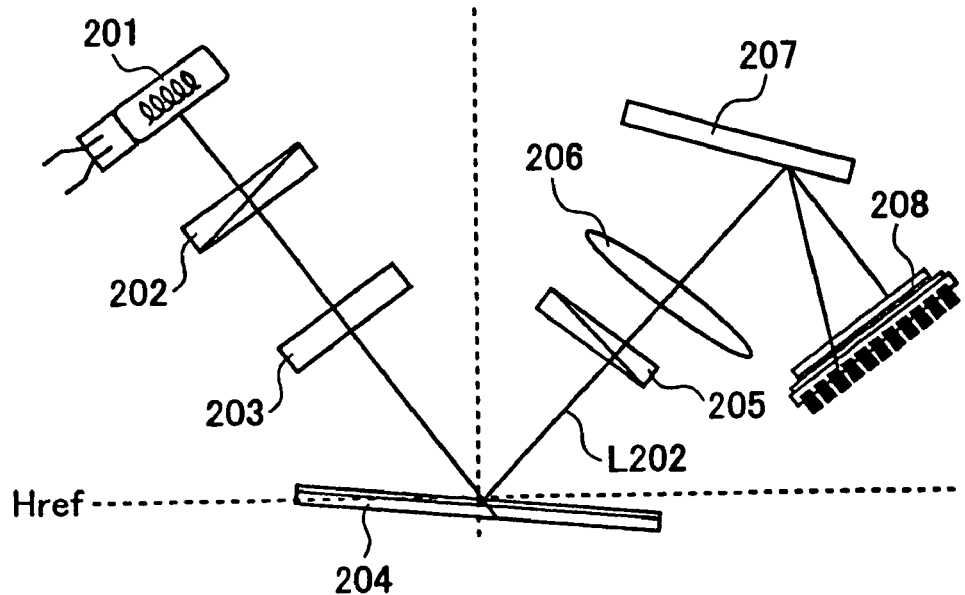
A  Positional relation between optical system and sample
(angle leaning to right)
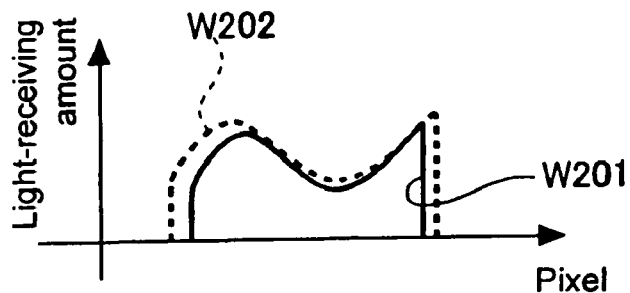
B  Reflected light intensity distribution waveform
PRIOR ART

Fig. 49
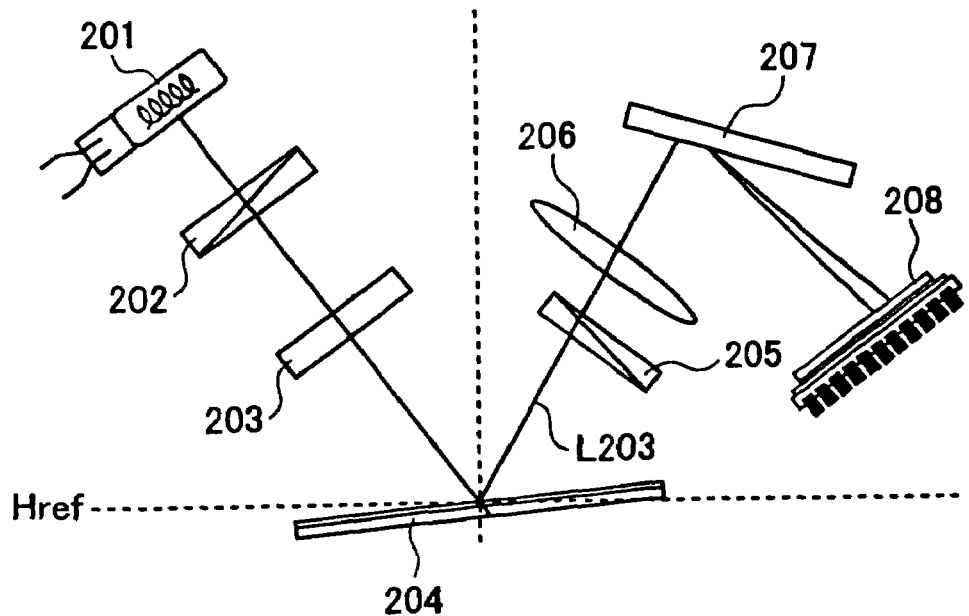
A  Positional relation between optical system and sample (angle leaning to left)
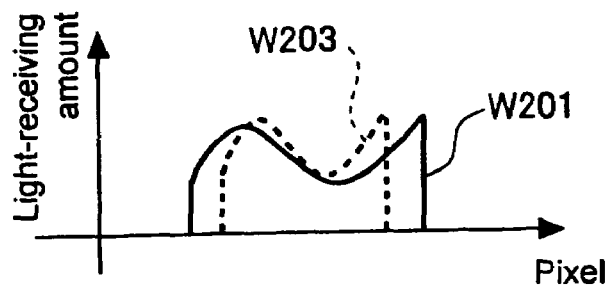
B  Reflected light intensity distribution waveform
PRIOR ART

Fig. 50
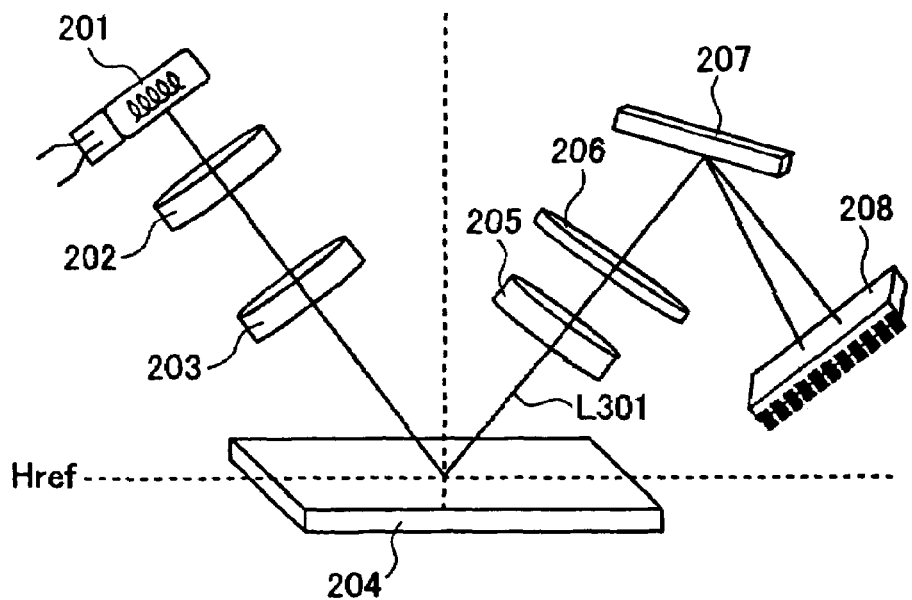
A  Positional relation between optical system and sample
(reference angle)
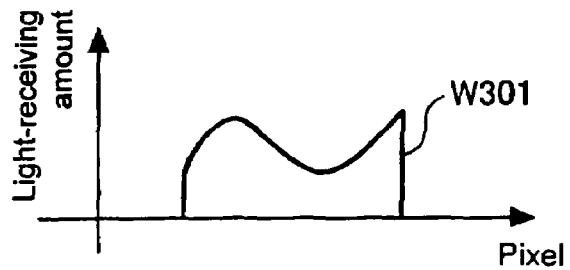
B  Reflected light intensity distribution waveform
PRIOR ART

Fig. 51
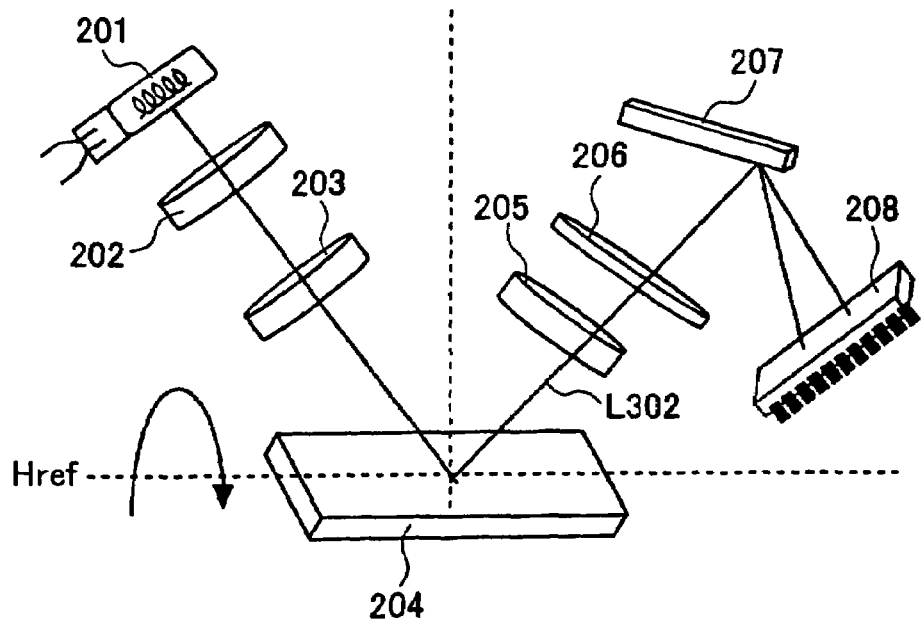
A  Positional relation between optical system and sample
(angle leaning backward)
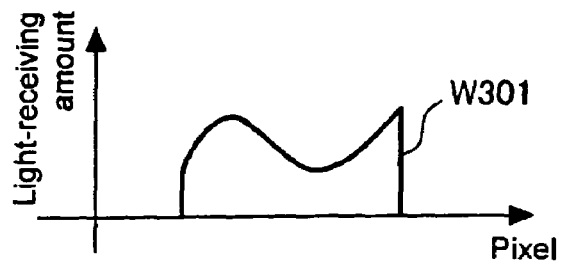
B  Reflected light intensity distribution waveform
PRIOR ART

Fig. 52
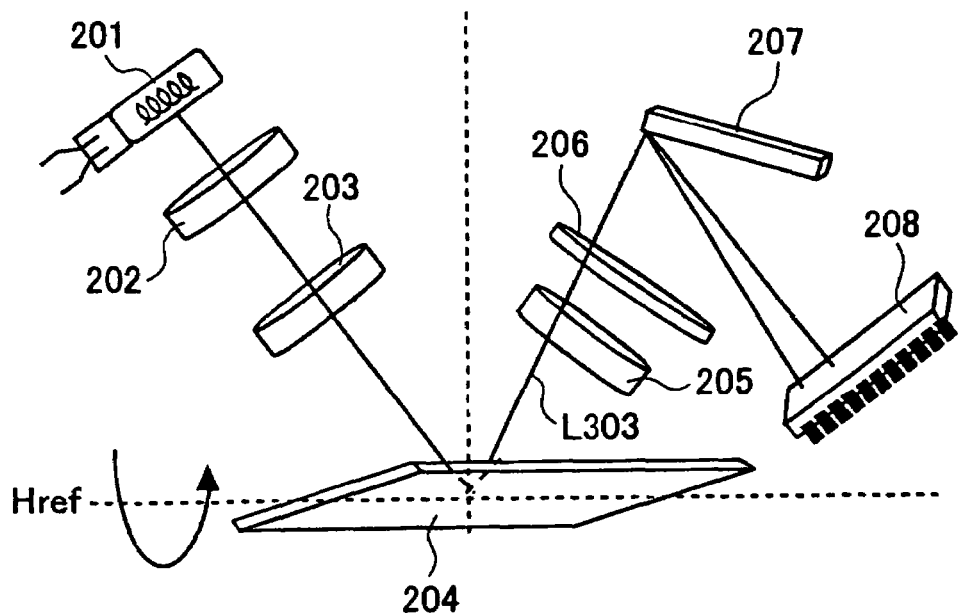
A  Positional relation between optical system and sample
(angle leaning forward)
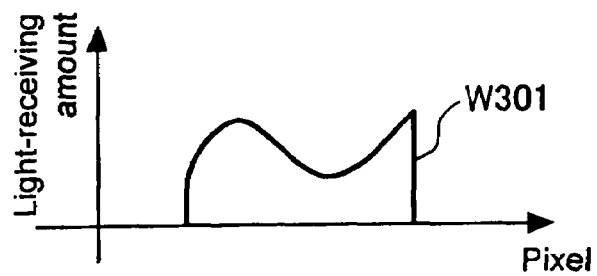
B  Reflected light intensity distribution waveform
PRIOR ART

SPECTROMETRIC MEASURING INSTRUMENT

BACKGROUND OF THE INVENTION

1. Field of the Invention

The present invention relates to a spectrometric measuring instrument using suitable changes in state of polarization of light for application of measurement of a thickness or quality (optical constant, sample structure, etc.) of a thin film, and the like, and particularly relates to a spectrometric measuring instrument suitable for in-line measurement performed in a production line.

2. Description of Related Art

In semiconductor manufacturing processes, recent upsizing, as well as miniaturization of design rules, of semiconductors substrates has raised the possibility of occurrence of excessive damage due to defect possible and necessitated control of delicate abnormality, and thereby testing is increasingly important.

Also in processes for manufacturing FPDs (flat panel displays) typified by an LCD (liquid crystal display) and a PDP (plasma display panel), screen sizes, fineness, and appearance quality are rapidly on the increase with increase in size of glass substrates. Therefore, in order to produce products of high quality in high yield, the importance of testing becomes increasingly high.

Tests of products in the manufacturing process of this kind, especially a film-thickness test, have hitherto been conducted in off-line measurement using a large and expensive spectrometric measuring instrument. This off-line measurement is performed through the following series of procedures. Products are sampled from a manufacturing process, carried to a spectrometric measuring instrument apart from the line, and then subjected to measurement and checking.

In such an off-line measurement, there has been a problem as follows. In the case where a measured result deviates from a control standard, it requires time to feedback that information to be reflected to the process so as to make a correction. Further, as for products not sampled in the manufacturing line, it is not possible to determine whether of not each of the products deviates from the control standard, thereby causing the yield to be lowered.

Therefore, the needs are growing for, for example, incorporating a spectrometric measuring instrument into a film formation process (in-situ) or immediately after the film formation process in a manufacturing line for products, to realize in-line film thickness measurement, in which a total measurement is performed without sampling products from the manufacturing process, so as to improve the product yield.

As a spectrometric measuring instrument applicable to such in-line measurement, it is required to satisfy the following conditions: (1) having an equivalent function to a function of a spectrometric measuring instrument to be used in a conventional film-thickness measurement; (2) being small-sized and capable of high-speed arithmetic processing; and (3) having resistance to later-described distance fluttering and angle fluttering. Additionally, as design rules have recently become finer, an insulating film and the like have become extremely thinner, and thereby testing of a thickness and quality of an ultra-thin film of several nanometers is increasingly important.

In a conventional film-thickness measurement, a thickness-meter of a spectroscopic analysis system or a polarimetry system is mainly used. However, the thickness-meters of those systems are both comprised of a spectroscope using a diffraction grating, and thus have a drawback of causing the instrument to be large-sized and thus be not suitable for the in-line measurement.

Moreover, since only a reflectance as an average value of an S polarized light and a P polarized light is measurable in the thickness-meter of the spectroscopic analysis system, an amount of information is small as compared to the thickness-meter of the polarimetry system typified by an ellipsometer for gathering up the reflectances of the S polarized light and a P polarized light to calculate a film thickness. It is therefore not possible for the thickness-meter of the spectroscopic analysis system to perform accurate measurement.

Further, in the thickness-meter of the spectroscopic analysis system, a reflectance is calculated by obtaining a ratio between an intensity distribution waveform of a wave incident on the sample and an intensity distribution waveform of a wave reflected from the sample. It is therefore necessary to perform another operation for measuring an intensity distribution waveform of an incident wave at the time of film thickness measurement. Consequently, the thickness-meter of the spectroscopic analysis system has a drawback of increasing the measurement time, which is disadvantageous for the in-line measurement.

On the other hand, in the thickness-meter of the polarimetry system, the intensity distribution waveform of the S polarized light and the intensity distribution waveform of the P polarized light are simultaneously measured, and a film thickness is measured based upon this measurement, thereby not requiring another operation for measuring an intensity distribution waveform of an incident wave. Therefore, the thickness-meter of the polarimetry system requires just a short measurement time and can thus be said to be suitable for the in-line measurement.

Further, analyzing film quality (optical constant, sample structure, etc.) of a material requires a spectrum measured in a wide wavelength region. In terms of measuring the film quality, the thickness-meter of the spectroscopic polarimetry system is advantageously used. It is to be noted that "film thickness" mentioned here means a variety of characteristics such as a refractive index, an absorption coefficient, a band structure, and a crystal structure.

FIG. 42 shows a conventional example of a single incident angle spectroscopic ellipsometer for rotating an analyzer as the thickness-meter of the polarimetry system (cf. Japanese Patent Laid-Open No. Hei 6-288835). In this figure, symbol a denotes a light source part, symbol b denotes a polarizer, symbol c denotes a quarter wavelength plate, symbol d denotes a measurement sample, symbol e denotes a rotating analyzer, symbol f denotes an analyzer driving part, symbol g denotes an electronic calculator, symbols h1 to h5 denote optical detectors, and symbol i denotes a diffraction grating.

For convenience of explanation, FIG. 43 shows an example in which the optical detectors h1 to h5 in the single incident angle spectroscopic ellipsometer shown in FIG. 42 have been replaced by a photo-array type detector. In this figure, numeral 101 denotes multi-colored light source, numeral 102 denotes a polarizer, a numeral 103 denotes a retarder, numeral 104 denotes a sample, numeral 105 denotes an analyzer, numeral 106 denotes a condenser lens, numeral 107 denotes a diffraction grating, and numeral 108 denotes a one-dimensional CCD.

As apparent from FIG. 43, light emitted from the multi-colored light source 101 passes through the retarder 102 and the analyzer 103 to be brought into a state of straight-line polarization, which is incident obliquely on the surface of the sample 104. On the optical path of the reflected light from the sample 104, the analyzer 105 for checking the state of polarization, the condenser lens 106, the diffraction grating 107 having a spectral function, and the photo-array detector 108 are arranged in this order. Thereby, the state of polarization of the reflected light with respect to each wavelength is measured to acquire a corresponding spectrum. Finally, an arithmetic part (not shown) performs fitting of a theoretical waveform to a measured waveform, to calculate a film thickness of the sample.

As for the foregoing single incident angle spectroscopic ellipsometer, since it is comprised of a spectrometer using a diffraction grating, the instrument becomes large-sized (first problem), and thus becomes difficult to incorporate the instrument in a line for the in-line measurement.

In the case where later-described distance fluttering occurs, an intensity distribution waveform of reflected light observed does not change. However, in the case where later-described angle fluttering in a horizontal direction or angle fluttering in a perpendicular direction occurs, an intensity distribution waveform of reflected light observed widely varies (second problem), to make measurement difficult. That is, since the single incident angle spectroscopic ellipsometer is susceptible to the distance fluttering as well as the angle fluttering, it is impossible to perform the in-line measurement in terms of actual application of the ellipsometer. For resolving such a situation, a stage needs arranging exclusively for fixing a sample required to be measured, which significantly restricts conditions for setting the instrument.

Further, since it is necessary to position a distance to the sample and inclination of the sample prior to measurement (third problem), it takes time to adjust the stage. This results in an increase in measurement time, and thereby the single incident angle spectroscopic ellipsometer is considered as not appropriate for the in-line measurement.

[Explanation of Distance Fluttering]

"Distance fluttering" is described while referring to FIGS. 44 to 46. In FIGS. 44 to 46, numeral 201 denotes a multicolored light source, numeral 202 denotes a polarizer, numeral 203 denotes a retarder, numeral 204 denotes a sample such as a semiconductor product or an FDP, numeral 205 denotes an analyzer, numeral 206 denotes a condenser lens having a convergence point on a light-receiving face of a one-dimensional CCD, numeral 207 denotes a diffraction grating, numeral 208 denotes a one-dimensional CCD, and those figures show simplified examples of the invention described in Japanese Patent Laid-Open No. Hei-288835.

It is to be noted that FIG. 44 shows a view of the case where the sample is arranged at a reference height, FIG. 45 shows a view of the case where the sample is arranged at a lowered height, and FIG. 46 shows a view of the case where the sample is arranged at a raised height.

The distance fluttering is a phenomenon that a distance between an optical system (e.g. the retarder 203) and the sample 204 varies. If this distance fluttering occurs, the position of a reflected light intensity distribution waveform observed through the one-dimensional CCD 208 varies although the width thereof in the direction of the array line does not vary. Accordingly, an optical constant of the thin film calculated based upon the intensity distribution waveform is inaccurate.

As apparent from the comparison between FIGS. 44 and 45, since the position of incidence of the reflected light L101 from the sample 204 arranged at the reference height on the diffraction grating 207 differs from that of the reflected light L102 from the sample 204 arranged at the lowered height, while the reflected lights L101 and L102 are in parallel, the reflected light intensity distribution waveform W101 when the sample 204 is arranged at the reference height does not agree with the reflected light intensity distribution waveform W102 when the sample 204 is arranged at the lowered height.

Similarly, as apparent from the comparison between FIGS. 44 and 46, since the position of incidence of the reflected light L101 from the sample 204 arranged at the reference height on the diffraction grating 207 differs from that of the reflected light L103 from the sample 204 arranged at the raised height, while the reflected lights L101 and L103 are in parallel, the reflected light intensity distribution waveform W101 when the sample 204 is arranged at the reference height does not agree with the reflected light intensity distribution waveform W103 when the sample 204 is arranged at the raised height.

[Explanation of Angle Fluttering in Horizontal Direction]

"Angle fluttering in a horizontal direction" is described while referring to FIGS. 47 to 49. In FIGS. 47 to 49, the same components as shown in FIGS. 44 to 46 are provided with the same numerals as in FIGS. 44 to 46, and explanations of those components are omitted.

It is to be noted that FIG. 47 shows a positional relation between the optical system and the sample when the sample is arranged at a reference angle (flat face perpendicular to the incident face), FIG. 48 shows the positional relation when the sample is in the state of slanting to the right (leaning to the right), and FIG. 49 shows the positional relation when the sample is in the state of slanting to the left (leaning to the left).

The angle fluttering in the horizontal direction is a phenomenon that the inclination of the sample 204 varies in a direction rotating around a straight line as a central axis, the line being perpendicular to the incident face. If this angle fluttering in the horizontal direction occurs, the width of a reflected light intensity distribution waveform in the direction of the array line observed through the one-dimensional CCD 208 varies, and thereby, an optical constant of the thin film calculated based upon the intensity distribution waveform is inaccurate.

As apparent from the comparison between FIGS. 47 and 48, the reflected light L201 from the sample 204 when arranged at the reference angle and the reflected light L202 from the sample 204 when arranged at the angle leaning to the right are not in parallel, and the respective angles and positions at which the reflected lights L201 and L202 are incident on the diffraction grating 207 differ. Therefore, the reflected light intensity distribution waveform W201 when the sample 204 is arranged at the reference angle does not agree with the reflected light intensity distribution waveform W202 when the sample 204 is arranged at the angle leaning to the right.

Similarly, as apparent from the comparison between FIGS. 47 and 49, the reflected light L201 from the sample 204 when arranged at the reference angle and the reflected light L203 from the sample 204 when arranged at the angle leaning to the left are not in parallel, and the respective angles and positions at which the reflected lights L201 and L203 are incident on the diffraction grating 207 differ. Therefore, the reflected light intensity distribution waveform W201 when the sample 204 is arranged at the reference angle does not agree with the reflected light intensity distribution waveform W203 when the sample 204 is arranged at the angle leaning to the left.

[Explanation of Angle Fluttering in Perpendicular Direction]

"Angle fluttering in a perpendicular direction" is described while referring to FIGS. 50 to 52. In FIGS. 50 to 52, the same components as shown in FIGS. 44 to 46 are provided with the same numerals as in FIGS. 44 to 46, and explanations of those components are omitted.

It is to be noted that FIG. 50 shows a positional relation between the optical system and the sample when the sample is arranged at a reference angle (flat face perpendicular to the incident face), FIG. 51 shows the positional relation when the sample is in the state of slanting backward (leaning backward), and FIG. 52 shows the positional relation when the sample is in the state of slanting backward (leaning backward).

The angle fluttering in the perpendicular direction is a phenomenon that inclination of a sample varies in a direction rotating around a straight line as a central axis, the line being an intersection between an incident face and a face to be measured. If this angle fluttering in the perpendicular direction occurs, the stretching direction of the light diffracted on the diffraction grating 207 is displaced from the array line direction of the one-dimensional CCD 208, whereby the reflected light intensity distribution cannot be completely received on the one-dimensional CCD 208. As a result, an optical constant of the thin film calculated based upon the intensity distribution waveform is inaccurate.

As apparent from the comparison between FIGS. 50 and 51, the reflected light L301 from the sample 204 when arranged at the reference angle and the reflected light L302 from the sample 204 when arranged at the angle leaning backward are not in parallel, and the respective angles and positions at which the reflected lights L301 and L302 are incident on the diffraction grating 207 differ. Therefore, the reflected light intensity distribution waveform W301 when the sample 204 is arranged at the reference angle does not agree with the reflected light intensity distribution waveform W302 when the sample 204 is arranged at the angle leaning backward.

Similarly, as apparent from the comparison between FIGS. 50 and 52, the reflected light L301 from the sample 204 when arranged at the reference angle and the reflected light L303 from the sample 204 when arranged at the angle leaning backward are not in parallel, and the respective angles and positions at which the reflected lights L301 and L303 are incident on the diffraction grating 207 differ. Therefore, the reflected light intensity distribution waveform W301 when the sample 204 is arranged at the reference angle does not agree with the reflected light intensity distribution waveform W303 when the sample 204 is arranged at the angle leaning backward.

It is to be noted that, hereinafter, the angle fluttering in the horizontal direction and the angle fluttering in the perpendicular direction are collectively referred to as the angle fluttering.

SUMMARY OF THE INVENTION

The present invention was made with the focus on the foregoing problems of conventional thickness-meters including those of the spectroscopic analysis system and the polarimetry system. An object of the present invention is to provide a spectrometric measuring instrument suitable for in-line measurement for example in a semiconductor manufacturing process, an FPD manufacturing process, or the like.

More specific object of the present invention is to provide a spectrometric measuring instrument with the size thereof reduced, having resistance to distance fluttering and angle fluttering in horizontal and perpendicular directions.

The spectrometric measuring instrument of the present invention is a measuring instrument, which is a measuring instrument for irradiating a sample with measuring medium light to receive a reflected light and detecting a change in polarized state of the reflected light from the irradiated light, to obtain a film thickness or film quality of the sample, wherein the instrument comprises: a light-projecting side optical system for applying and condensing measuring medium light, including various azimuth angle components, onto a sample surface; a light-receiving side optical system, which includes a photoelectric transfer part array means formed by arranging a large number of photoelectric transfer parts in arrayed form in a direction perpendicular to an incident face and a light interference type spectral element for gradually changing a wavelength of transmitted light by means of a lens and a transmitted position, and in which the spectral element is provided immediately before the photoelectric transfer part array means and a distance between the lens and the light-receiving face of the photoelectric transfer part array means is set so as to almost agree with a focal distance of the lens so that the light is received from the sample through the lens by the photoelectric transfer part array means; and an arithmetic part for making an amount of change in state of polarization of the reflected light from the irradiated light correspond to the transmission wavelength of the spectral element based upon a series of light-receiving amount data which is obtained from each of the photoelectric transfer parts of the photoelectric transfer part array means and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness,or film quality, and further, the light-projecting side optical system includes a characterization means of characterizing variations in inclination of the sample in a direction rotating around a straight line as a central axis, the line being perpendicular to the incident face of the measured medium light, the light-receiving side optical system includes an inclination detecting photoelectric transfer means of receiving the reflected light of the measuring medium light reaching from a film-thickness measuring point of the sample, to detect a characteristic in variations in inclination of the sample included in the received reflected light, and the arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means.

The characterization means of characterizing variations in inclination of the sample in a direction rotating around a straight line as a central axis, the line being perpendicular to the incident face of the measured medium light, is performed in cases including the case where a measuring medium light having a predetermined shape or intensity distribution is applied on the sample.

Further, the light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means, includes a means in which the reflected light from the sample is received by the inclination detecting photoelectric transfer means, and according to the shape or the intensity distribution of the received light, the light-receiving position of the measuring medium light irradiated as having the predetermined shape or intensity distribution is found, whereby an error component generated due to variations in inclination of the sample is corrected based upon a comparison with a position in which the light is to be received if the sample is not inclined. The predetermined shape or intensity distribution of the measuring medium light may be at least a shape or an intensity distribution in a direction perpendicular to the traveling direction of the measuring medium light or in a direction parallel to the incident face.

The spectrometric measuring instrument of the present invention is a measuring instrument, which is a measuring instrument for irradiating a sample with measuring medium light to receive a reflected light and detecting a change in state of polarization of the reflected light from the irradiated light, to obtain a film thickness or film quality of the sample, wherein the instrument comprises: a light-projecting side optical system for applying and condensing measuring medium light, including various azimuth angle components, onto a sample surface; a light-receiving side optical system, which includes a photoelectric transfer part array means formed by arranging a large number of photoelectric transfer parts in arrayed form in a direction perpendicular to an incident face and a light interference type spectral element for gradually changing a wavelength of transmitted light by means of a lens and a transmitted position, and in which the spectral element is provided immediately before the photoelectric transfer part array means and a distance between the lens and the light-receiving face of the photoelectric transfer part array means is set so as to almost agree with a focal distance of the lens so that the light is received from the sample through the lens by the photoelectric transfer part array means; and an arithmetic part for making an amount of change in state of polarization of the reflected light from the irradiated light correspond to the transmission wavelength of the spectral element based upon a series of light-receiving amount data which is obtained from each of the photoelectric transfer parts of the photoelectric transfer part array means and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness or film quality, and further, the light-projecting side optical system includes a characterization means of characterizing variations in inclination of the sample in a direction rotating around a straight line as a central axis, the line being an intersection between the incident face and a face to be measured, and the arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the photoelectric transfer part array means.

The characterization means of characterizing variations in inclination of the sample in a direction rotating around a straight line as a central axis, the line being an intersection between the incident face and a face to be measured, is performed in cases including the case where a measuring medium light having a predetermined shape or intensity distribution is applied on the sample. Further, the light-receiving amount data correcting means includes a means in which the reflected light from the sample is received by the inclination detecting photoelectric transfer means, and according to the shape or the intensity distribution of the received light, the light-receiving position of the measuring medium light irradiated as having the predetermined shape or intensity distribution is found, whereby an error component generated due to variations in inclination of the sample is corrected based upon a comparison with a position in which the light is to be received if the sample is not inclined. The predetermined shape or intensity distribution of the measuring medium light may be at least a shape or an intensity distribution in a direction perpendicular to the face of the sample on which the measuring medium light is incident.

The spectrometric measuring instrument of the present invention is a measuring instrument, which is a measuring instrument for irradiating a sample with measuring medium light to receive a reflected light and detecting a change in state of polarization of the reflected light from the irradiated light, to obtain a film thickness or film quality of the sample, wherein the instrument comprises: a light-projecting side optical system for applying and condensing measuring medium light, including various azimuth angle components, onto a sample surface; a light-receiving side optical system, which includes a photoelectric transfer part array means formed by arranging a large number of photoelectric transfer parts in arrayed form in a direction perpendicular to an incident face and a light interference type spectral element for gradually changing a wavelength of transmitted light by means of a lens and a transmitted position, and in which the spectral element is provided immediately before the photoelectric transfer part array means and a distance between the lens and the light-receiving face of the photoelectric transfer part array means is set so as to almost agree with a focal distance of the lens so that the light is received from the sample through the lens by the photoelectric transfer part array means; and an arithmetic part for making an amount of change in state of polarization of the reflected light from the irradiated light correspond to the transmission wavelength of the spectral element based upon a series of light-receiving amount data which is obtained from each of the photoelectric transfer parts of the photoelectric transfer part array means and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness or film quality, and further, the light-projecting side optical system includes a first characterization means of characterizing variations in inclination of the sample in a direction rotating around a straight line as a central axis, the line being perpendicular to the incident face of the measured medium light, and further includes a second characterization means of characterizing variations in inclination of the sample in a direction rotating around a straight line as a central axis, the line being an intersection between the incident face and a face to be measured, the light-receiving side optical system includes an inclination detecting photoelectric transfer means of receiving the reflected light of the measuring medium light reaching from a film-thickness measuring point of the sample, to detect a characteristic in the first characterization means included in the received reflected light, and further, a distance between the lens and the inclination detecting photoelectric transfer means, which are included in the light-receiving side optical system, is set so as to almost agree with a focal distance of the lens, and the arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the photoelectric transfer part array means, and further includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means.

The predetermined shape or intensity distribution of the measuring medium light may be a shape or an intensity distribution in a direction perpendicular to the traveling direction of the measuring medium light or in a direction parallel to the incident face or in a direction perpendicular to the face of the sample on which the measuring medium light is incident.

In a preferred embodiment, the characterization means is a section contour shaping means of edge-shaping a part, corresponding to an inclination reference of the sample, in the section contour of the measuring medium light.

In a preferred embodiment, the section contour shaping means at least includes a slit, an aperture, or a knife edge.

In a preferred embodiment, a white light source is used as the light source.

In a preferred embodiment, the white light source is an LED light source.

In a preferred embodiment, a diameter of a spot on the sample is not larger than 1 mm.

In a preferred embodiment, a two-dimensional array means is used as the photoelectric transfer part array means.

In a preferred embodiment, the arithmetic part for calculating the theoretical waveform includes a process for correcting an error due to wavelength resolution of the spectrometric element.

In a preferred embodiment, the arithmetic part includes a process for calculating a theoretical waveform according to a theoretical formula of reflectance of light including light reflected from the rear face of a sample substrate in the case where the sample substrate is a transparent substrate.

In a preferred embodiment, the arithmetic part has an input means capable of inputting whether the sample substrate is a transparent substrate or an opaque substrate.

In a preferred embodiment, the instrument comprises a mechanism for rotating a retarder having the function of retarding a phase, the light-projecting side optical system includes a polarizer, and the light-receiving side optical system includes an analyzer.

In a preferred embodiment, the light-projecting side optical system comprises the retarder having the function of retarding a phase.

In a preferred embodiment, the measuring medium light irradiated from the light-projecting side optical system includes two or more polarized components, and the light-receiving side optical system includes: two or more photoelectric transfer part array means corresponding to the respective polarized components; and a polarization splitting means of splitting reflected light, reaching from a film-thickness measuring point on the sample, into polarized components to guide the respective split polarized components to appropriate photoelectric transfer part array means.

In a preferred embodiment, the chromaticity of the sample is measured.

In a preferred embodiment, the film thickness of the sample is measured.

In a preferred embodiment, the film quality of the sample is measured.

In a preferred embodiment, the instrument is disposed in a manufacturing line and performs an in-line measurement.

In a preferred embodiment, the instrument is disposed in the manufacturing line and performs a one-hundred-percent, testing, and then a logged and analyzed result can be fed back to the instrument in the manufacturing line.

According to the spectrometric measuring instrument of the present invention, size reduction is realized, and also resistance can be obtained to the distance fluttering, the angle fluttering in the horizontal direction, and the angle fluttering in the perpendicular direction. It is thereby possible to realize a spectrometric measuring instrument suitable for in-line measurement for example in a semiconductor manufacturing process, an FPD manufacturing process, or the like.

BRIEF DESCRIPTION OF THE SEVERAL VIEWS OF THE DRAWINGS

FIG. 2 shows a view showing one example of an optical configuration of a sensor head part.

FIG. 8 shows a view showing a description of table data (No. 1).

FIG. 9 shows a view showing a description of table data (No. 2).

FIG. 16 shows a view showing another example of the optical configuration of the sensor head part.

FIG. 28 shows a view showing another example of the optical configuration of the sensor head part.

FIG. 29 shows an explanatory view of an edge shaping means.

FIG. 30 shows a view showing another example of the optical system of the sensor head part.

FIG. 35 shows a view showing a description of table data.

FIG. 41 shows a view showing a description of table data.

FIG. 44 shows an explanatory view of distance flattering (No. 1).

FIG. 45 shows an explanatory view of distance flattering (No. 2).

FIG. 46 shows an explanatory view of distance flattering (No. 3).

FIG. 47 shows an explanatory view of angle flattering in the horizontal direction (No. 1).

FIG. 48 shows an explanatory view of angle flattering in the horizontal direction (No. 2).

FIG. 49 shows an explanatory view of angle flattering in the horizontal direction (No. 3).

FIG. 50 shows an explanatory view of angle flattering in the perpendicular direction (No. 1).

FIG. 51 shows an explanatory view of angle flattering in the perpendicular direction (No. 2).

FIG. 52 shows an explanatory view of angle flattering in the perpendicular direction (No. 3).

DETAILED DESCRIPTION OF THE PREFERRED EMBODIMENTS

First, in order to clarify the positioning of embodiments of the present invention, problems of the conventional spectroscopic ellipsometer and the relation thereof with the present invention are described.

[Problems of Conventional Spectroscopic Ellipsometer]

(1) First Problem

Since a diffraction grating type spectroscopic element is used as a spectroscopic means, the instrument becomes large-sized and is thus not suitable for the in-line measurement.

(2) Second Problem

Since the conventional spectroscopic ellipsometer is vulnerable to the distance fluttering and the angle fluttering, it is not possible to perform the in-line measurement.

Relation Between Above Problems and Embodiments of Present Invention (1) Solution to First Problem As shown in Embodiments 1 to 9, an interference type spectroscopic element (inclined film) was used as the spectroscopic means, to realize size reduction.

(2) Solution to Second Problem

Optical systems resistant to the distance fluttering shown in Embodiments 2 and 6, optical systems resistant to the angle fluttering in horizontal and perpendicular directions shown in Embodiments 3 and 7, optical systems resistant to the distance fluttering and the angle fluttering in horizontal and perpendicular directions shown in Embodiments 4 and 8 were realized, to make the in-line measurement possible.

Below, one preferred embodiment of the spectrometric measuring instrument according to the present invention is specifically described according to attached drawings.

Embodiment 1

Figure 1:
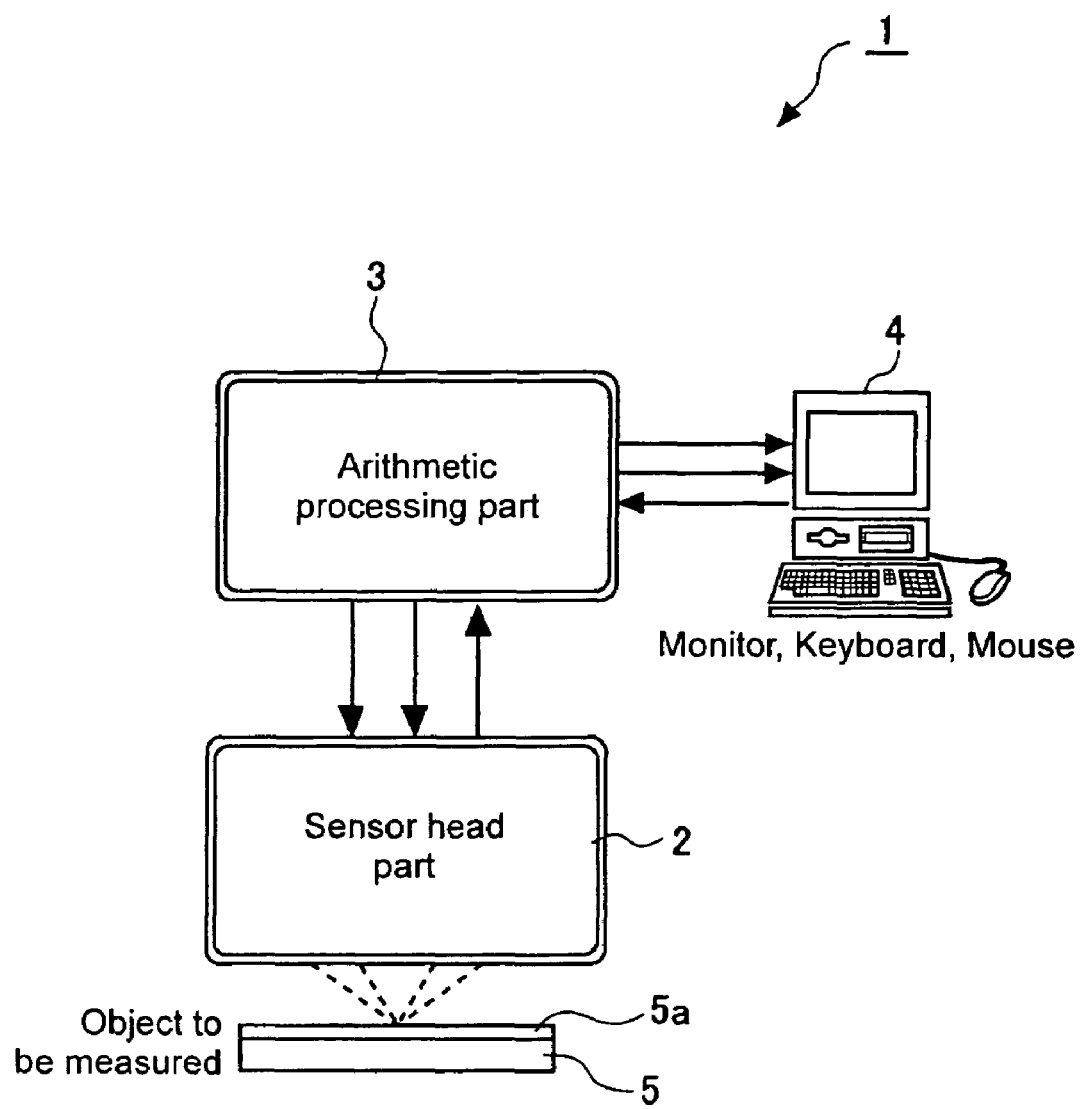
FIG. 1 shows a view of an overall configuration of a single incident angle spectroscopic ellipsometer (common among all embodiments).

FIG. 1 shows a configuration view showing the whole of a single incident angle spectroscopic ellipsometer. As shown in the figure, this ellipsometer 1 includes a sensor head part 2, an arithmetic processing part 3, and an HMI (human machine interface) part 4, such as a monitor keyboard mouse. It should be noted that, in this figure, numeral 5 denotes a substrate constituting a sample (e.g. semiconductor, FPD, etc.), and symbol 5a denotes a thin film to be measured which is present on the surface of the substrate 5. The basic configuration of the ellipsometer shown in this FIG. 1 is applied in common to all Embodiments 1 to 9 described below.

By reference to FIGS. 2 to 15, an ellipsometer of Embodiment 1 is specifically described. This ellipsometer has realized size reduction by using a light-interference type spectroscopic element (hereinafter, referred to as an inclined film) which gradually changes a transparent light wavelength by a transparent position, on the assumption that the basic configuration shown in FIG. 1 is adopted.

FIG. 2 shows an optical configuration of the sensor head part 2 with a small-sized technique incorporated therein. As shown in this figure, the ellipsometer 1 has a light-projecting optical system and a light-receiving optical system.

The light-projecting optical system includes: a light source (white light source in the illustrated example) 301; a collimator lens 302 for adjusting light emitted from the light source 301 into collimator light; a polarizer 303 for allowing only some polarized component in the collimator light launched from the collimator lens 302 to pass; a retarder 304 for retarding the phase of the light launched from the polarizer 303 by a quarter of light wavelength; a driving means 305 for rotating the retarder 304; and a condenser lens 306 for condensing the light after passage through the retarder to apply the light on a film-thickness measuring point of the thin film 5a of the substrate (sample) 5. It is to be noted that, as well known by the skilled person in the art, the retarder 304 rotates around the light axis as the center, upon receiving the drive from the driving means 305.

The light-receiving optical system comprises: a collimator lens (light-receiving lens) 308 for receiving reflected light of the measuring medium light applied on the substrate 5 and converting the light into collimator light; an analyzer 309 for allowing only some polarized component of the collimator light launched from the collimator lens 308 to pass; an inclined film 311 as an light-interference type spectroscopic element for gradually changing a transparent wavelength according to each position in the longitudinal direction; and a photoelectric transfer part array means (corresponding to one-dimensional CCD 310 in the illustrated example) formed by arranging a large number of photoelectric transfer parts in arrayed form in a direction perpendicular to the incident face (direction perpendicular to paper face).

The inclined film 311 is in the state of being attached to the light-receiving face of the one-dimensional CCD 310 constituting the photoelectric transfer part array means, and oriented such that the longitudinal direction thereof matches the direction of a pixel line of the one-dimensional CCD 310.

A series of light-receiving amount data obtained from each photoelectric transfer part of the photoelectric transfer part array means is sent to an arithmetic means (corresponding to the arithmetic processing part 3 in the illustrated example), to obtain the thickness of the thin film 5a to be measured.

Figure 3:
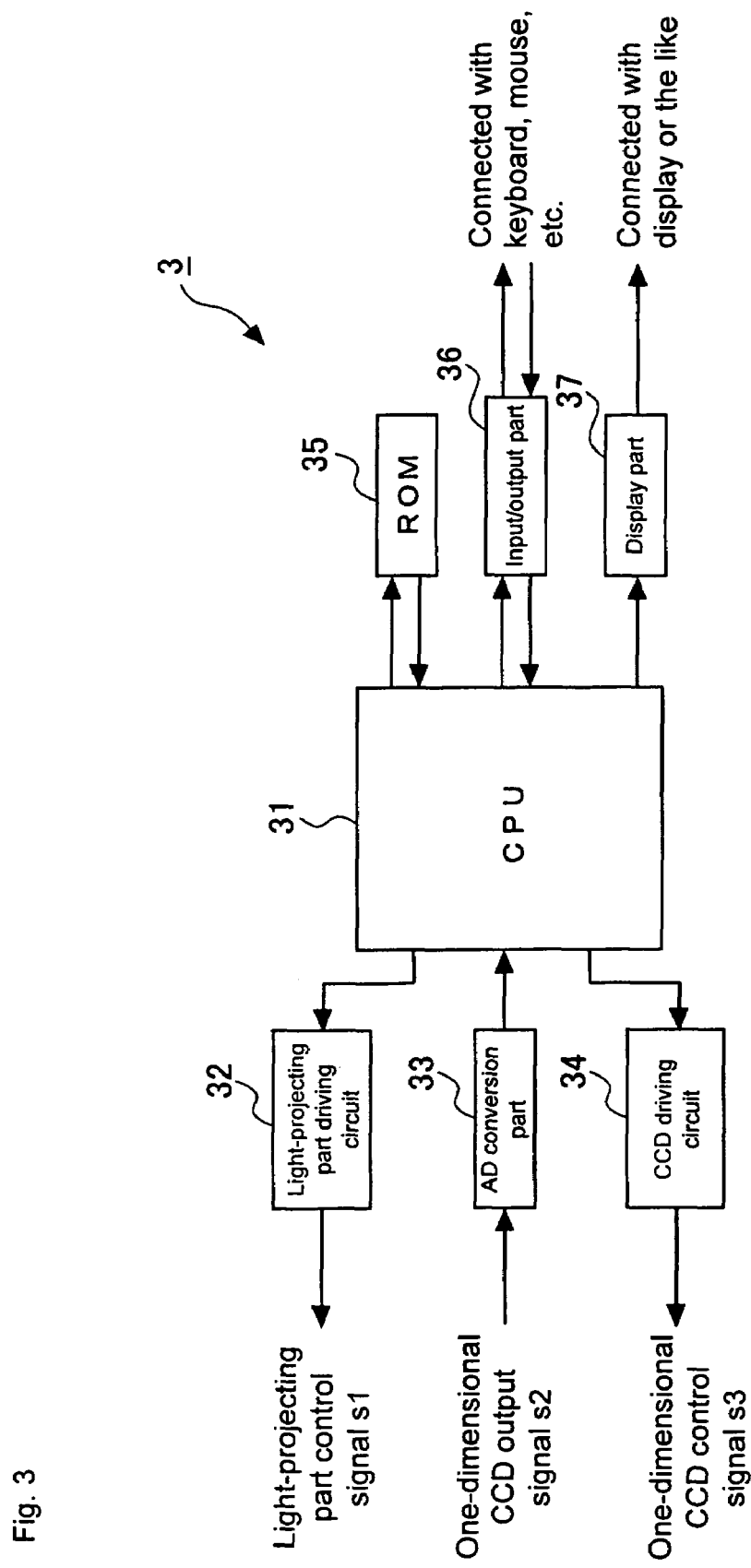
FIG. 3 shows a view showing an electric configuration of an arithmetic processing part.
Figure 4:
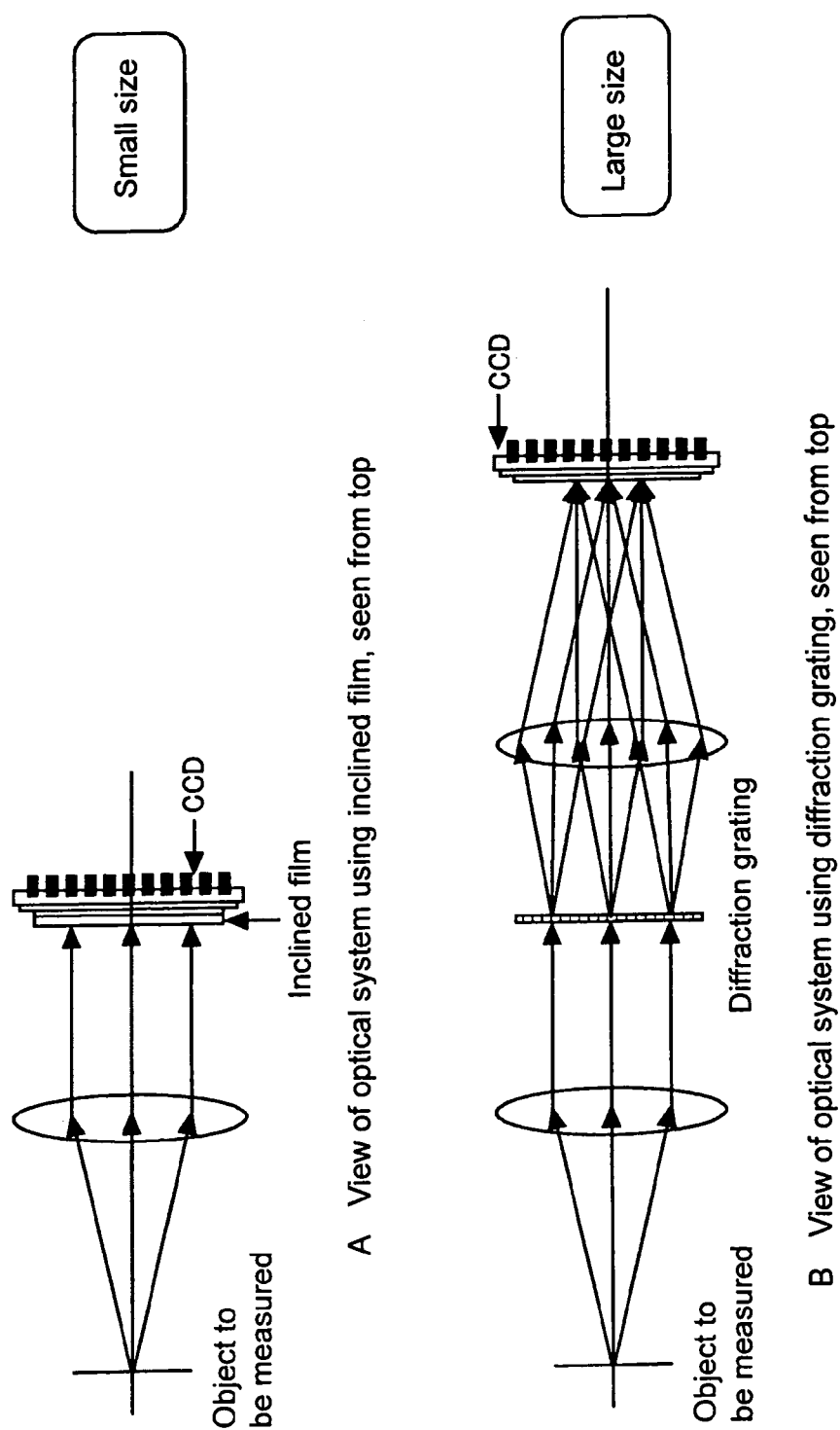
FIG. 4 shows an explanatory view of comparison between an optical system using an inclined film and an optical system using a diffraction grating.

FIG. 3 shows an electric configuration of the arithmetic processing part 3. As shown in the figure, the arithmetic processing part 3 is configured by comprising: a light-projecting part driving circuit 32 for producing and outputting a light-projecting part control signal s1, an A/D conversion part 33 for converting the digital signal to an output signal s2 from the one-dimensional CCD; a CCD driving circuit 34 for producing and outputting a one-dimensional CCD control signal s3; a ROM 35 stalling a variety of system programs; an input/output part 36 for functioning as an interface with a key board or a mouse which constitutes the HMI part; a display part 37 for functioning as an interface with a display which constitutes the HMI part; and a CPU 31 for integrally controlling the components 32 to 37 and also executing a later-described film-thickness measuring operation and the like.

Next, the function of the present embodiment according to the above configuration is described. In the present embodiment, the adoption of a rotation retarding method capable of obtaining all Stokes parameters ($S_0$ to $S_3$) enabled an accurate measurement. Further, the adoption of the interference type spectroscopic element (inclined film) leads to omission of a lens or the like in the diffraction grating subsequent step, to realize size reduction of the instrument (cf. FIG. 4).

A basic operation for film-thickness measurement is described while referring to FIG. 2. The measuring medium light emitted from the light source 301 converges and is applied on the thin film 5a on the substrate 5 to be measured by the function of the condenser lens 306, through the collimator lens 302, a polarizer 303 and a retarder 304. A film-thickness measuring point of the sample is set to almost the position on which the incident light converges. At this time, measuring medium light having a continuous incident light in the range of θ0 to θ1 is incident on the sample.

The measuring medium light incident through the condenser lens 306 is reflected on the sample. Light incident at an angle of θ2, out of the reflected light of the measuring medium light reaching from the film-thickness measurement point of the sample, is guided to the light-receiving face of the one-dimensional CCD 310 by the function of the light-receiving lens 308 through the collimator lens 308, the analyzer 309 and the inclined film 311.

Thereby, the one-dimensional CCD output signal s2, corresponding to serially aligned data on a light-receiving amount of each light-receiving element (pixel) from the one-dimensional CCD 310, is sent from the one-dimensional CCD 310. Based upon this one-dimensional CCD output signal s2, a reflected light intensity distribution according to a wavelength at the incident angle (θ2) is observed. The reflected light intensity distribution is observed at this time in an amount according to the wavelength.

The driving means (retarder) 305 is rotated by an angle of x degrees each time, to subsequently measure one-dimensional CCD data. When the driving means (retarder) 305 has rotated a half-turn (180 degrees), the data are processed in the arithmetic processing part 3, to calculate measured values in terms of a phase difference Δ and an amplitude ratio ψ. Simultaneously, the arithmetic part 3 calculates theoretical values in terms of the phase difference Δ and the amplitude ratio ψ, to obtain a film thickness by contrast of the measured values and the theoretical values.

A method for calculating measured values of the phase difference Δ and the amplitude ratio ψ are shown below. In the rotating retarder method, a light intensity waveform I detected by the one-dimensional CCD 310 is generally expressed by the following expression $I = I_0(1 + \alpha_0 \cos 2\omega t + \alpha_1 \sin 2\omega t + \alpha_2 \cos 4\omega t + \alpha_3 \sin 4\omega t)$ Here, $\alpha_0, \alpha_1, \alpha_2, \alpha_3$ indicate standardized Fourier series, ωt indicates a rotation angle of a retarder.

Further, a relational expression of the standardized Fourier series and Stokes parameter $S_0, S_1, S_2, S_3$ is generally expressed as follows.

[Expression 1]

$$S_0 = \frac{1}{\sin^2 2A}\alpha_0 - \frac{[1+\cos\phi(\lambda)]\cos 4P + 2\cos 2P \cos 2A}{[1-\cos\phi(\lambda)]\sin^2 2A} \times \alpha_1 - \frac{[1+\cos\phi(\lambda)]\sin 4P + 2\sin 2P \cos 2A}{[1-\cos\phi(\lambda)]\sin^2 2A} \times \alpha_2 \quad \text{Expression (1)}$$

$$S_1 = \frac{\cos 2A}{\sin^2 2A}\alpha_0 + \frac{[1+\cos\phi(\lambda)]\cos 4P \cos 2A + 2\cos 2P}{[1-\cos\phi(\lambda)]\sin^2 2A} \times \alpha_1 + \frac{[1+\cos\phi(\lambda)]\sin 4P \cos 2A + 2\sin 2P}{[1-\cos\phi(\lambda)]\sin^2 2A} \times \alpha_2 \quad \text{Expression (2)}$$

$$S_2 = \frac{2[\alpha_2 \cos 2P - \alpha_1 \sin 2P]}{[1-\cos\phi(\lambda)]\sin 2A} \quad \text{Expression (3)}$$

$$S_3 = \frac{\alpha_3}{\sin 2A \sin 2P \sin \phi(\lambda)} \quad \text{Expression (4)}$$

Here, P indicates an azimuthal angle of a retarder, A indicates an azimuthal angle of an analyzer, φ indicates a phase difference of a retarder, and λ indicates a wavelength. Further, a relational expression of the Stokes parameter $S_0$, $S_1$, $S_2$, $S_3$, the phase difference $\Delta$, and the amplitude ratio $\psi$ is generally expressed as follows. It should be noted that p indicates a polarization degree.

[Expression 2]

$$p = \sqrt{\left(\frac{S_1'}{S_0'}\right)^2 + \left(\frac{S_2'}{S_0'}\right)^2 + \left(\frac{S_3'}{S_0'}\right)^2} \qquad \text{Expression (5)}$$

$$\frac{S_1}{S_0} = -p \cos 2\psi \qquad \text{Expression (6)}$$

$$\frac{S_2}{S_0} = -p \sin 2\psi \cos \Delta \qquad \text{Expression (7)}$$

$$\frac{S_3}{S_0} = -p \sin 2\psi \sin \Delta \qquad \text{Expression (8)}$$

From the above expressions (1) to (8), the phase difference $\Delta$ and the amplitude ratio $\psi$ can be calculated.

Figure 5:
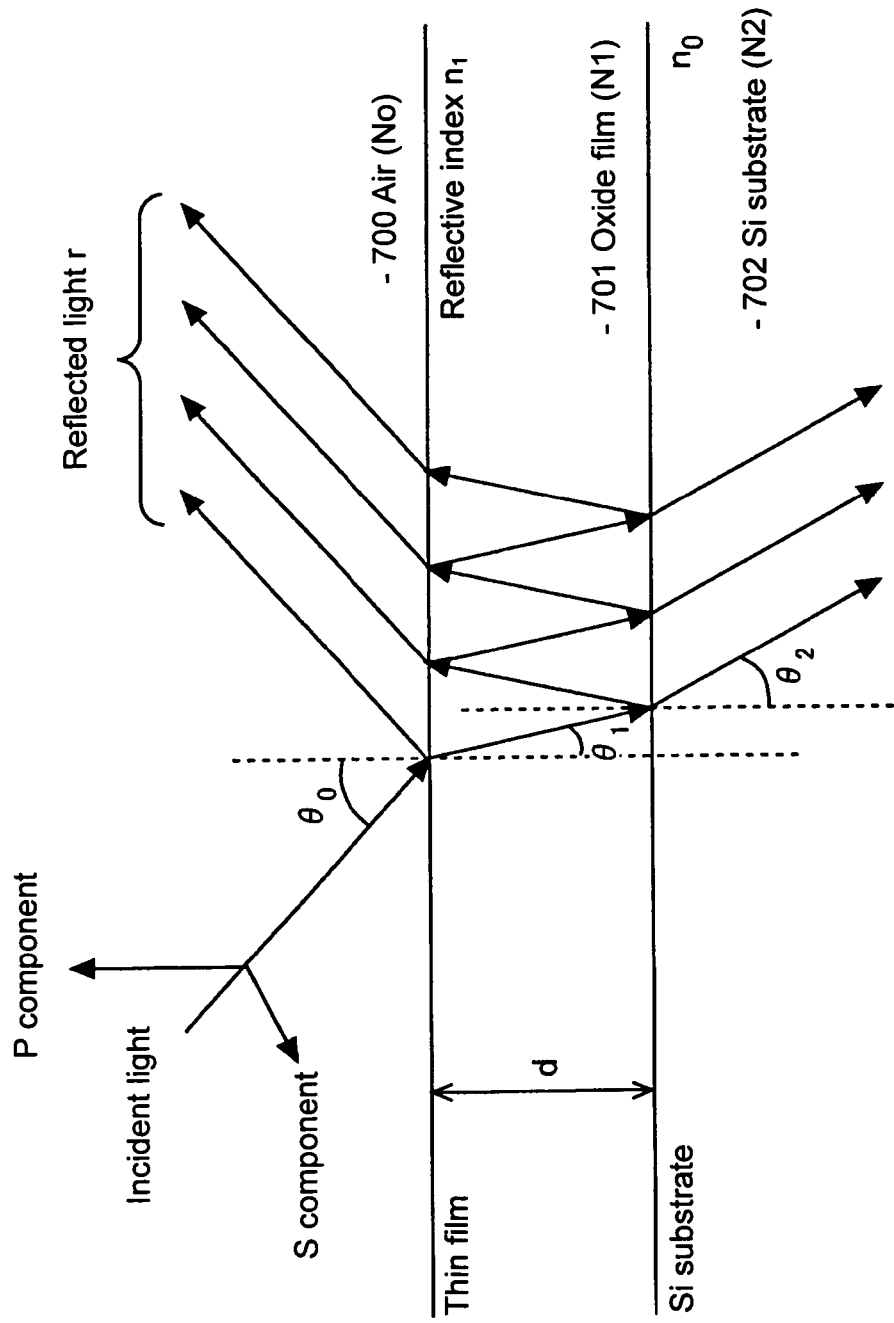
FIG. 5 shows an explanatory view showing relations between a thin film and incident light/reflected light.

Next, a method for calculating theoretical values of the phase difference $\Delta$ and the amplitude ratio $\psi$ is shown below. For example, as shown in FIG. 5, in the case of measuring a thickness of an oxide film (gate oxide film etc.) 701 formed on an Si substrate 702, as described above, incident light emitted in an elliptically polarized state from air (refractive index=N0) 700 reflects on the surface of the oxide film (refractive index=N1) 701, and most thereof is incident in the oxide film 701.

The light incident in the oxide film 701 reflects on the interface of the Si substrate (substrate face) (refractive index=N2) 702 and returns from the oxide film 701 to the air 700. The returned light interferes under polarization with light reflected on the surface of the oxide film 701. A p polarized component and an s polarized component of each of such light are calculated, to calculate the film thickness from each phase difference $\Delta$ and amplitude ratio $\omega$.

The p polarized component ($r_{1p}$) and the s polarized component ($r_{1s}$) of the reflected light on the face of the Si substrate 702 are respectively calculated in the following expressions:

$$r_{1p}=(n_2 \cos \theta_1 - n_1 \cos \theta_2)/(n_2 \cos \theta_1 + n_1 \cos \theta_2)$$

$$r_{1s}=(n_1 \cos \theta_1 - n_2 \cos \theta_2)/(n_1 \cos \theta_1 + n_2 \cos \theta_2)$$

Further, from the above $r_{1p}$, $r_{1s}$, the p polarized component ($r_{0p}$) and the s polarized component ($r_{0s}$) of the reflected light on the face of the oxide film 701, a p polarized component ($R_p$) and an s polarized component ($R_s$) of detected light are calculated according to the following expressions:

$$R_p=(r_{0p}+r_{1p}\exp(-2i\delta))/(1+r_{0p}\cdot r_{1p}\exp(-2i\delta))$$

$$R_s=(r_{0p}+r_{1s}\exp(-2i\delta))/(1+r_{0s}\cdot r_{1s}\exp(-2i\delta))$$

wherein, $\delta=2\pi n_1 d \cos \theta_1/\lambda$.

Figure 6:
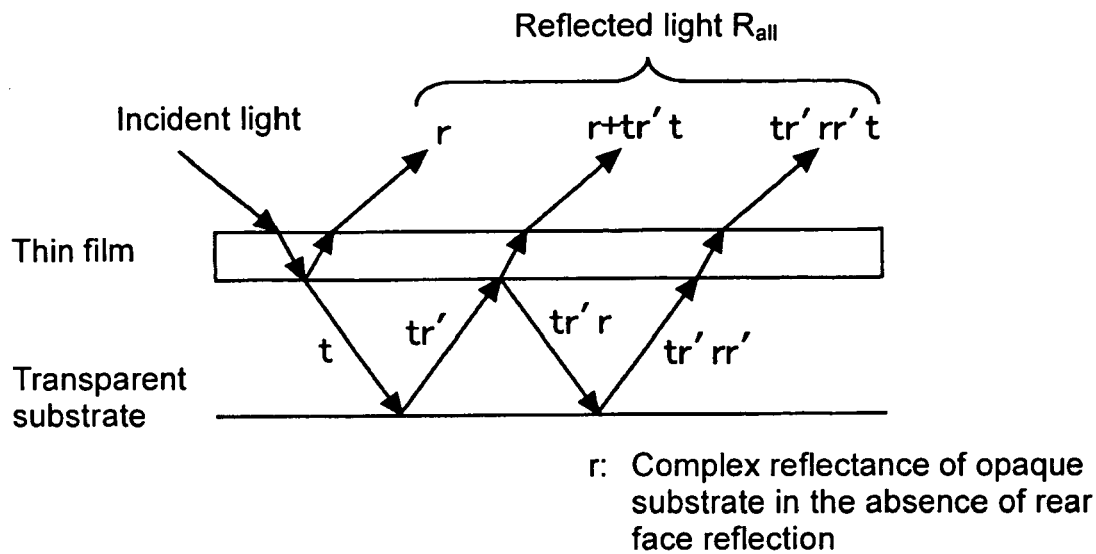
FIG. 6 shows an explanatory view showing a relation between a single-layered film and reflected light.
Figure 7:
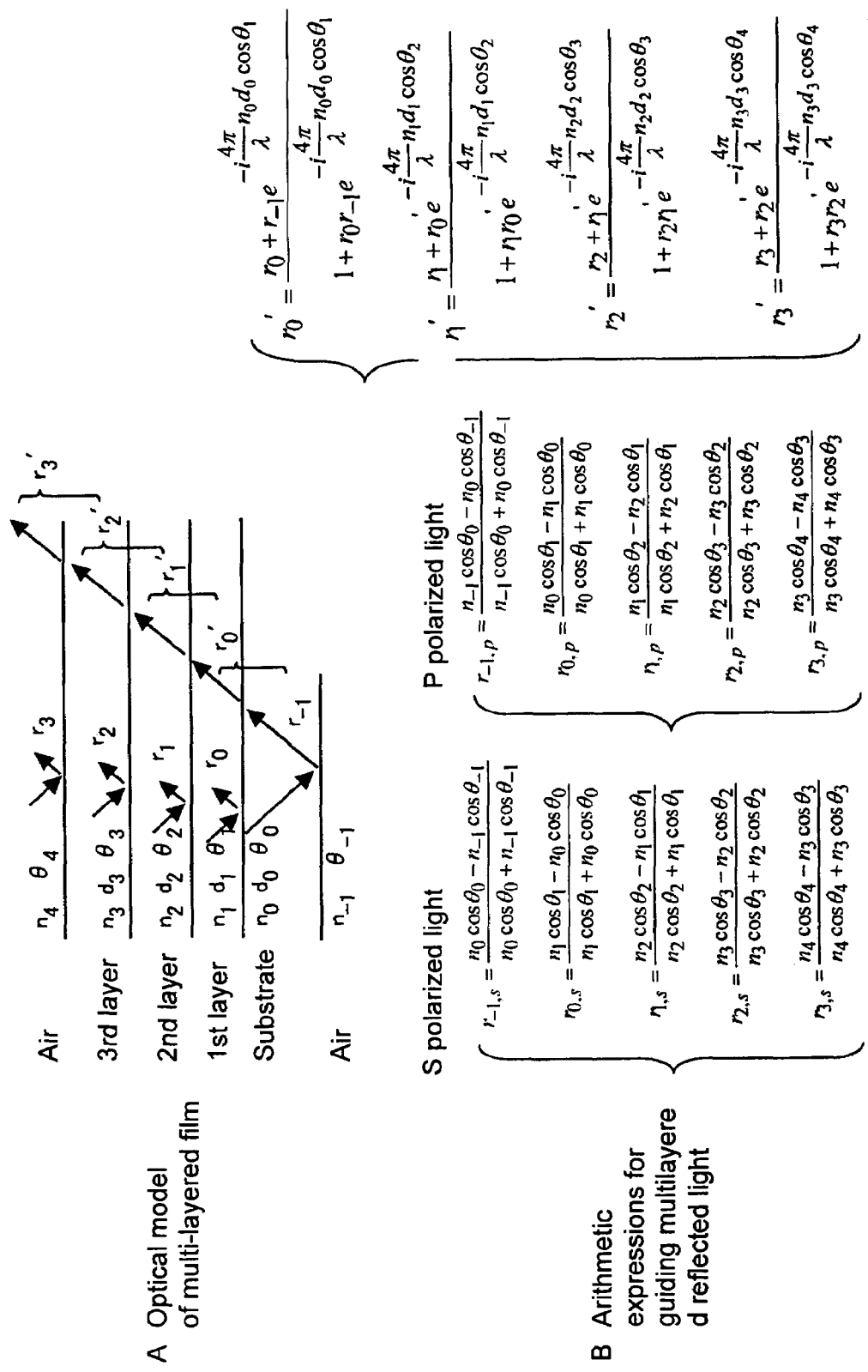
FIG. 7 shows an explanatory view showing a relation between a multi-layered film and reflected light.
Figure 10:
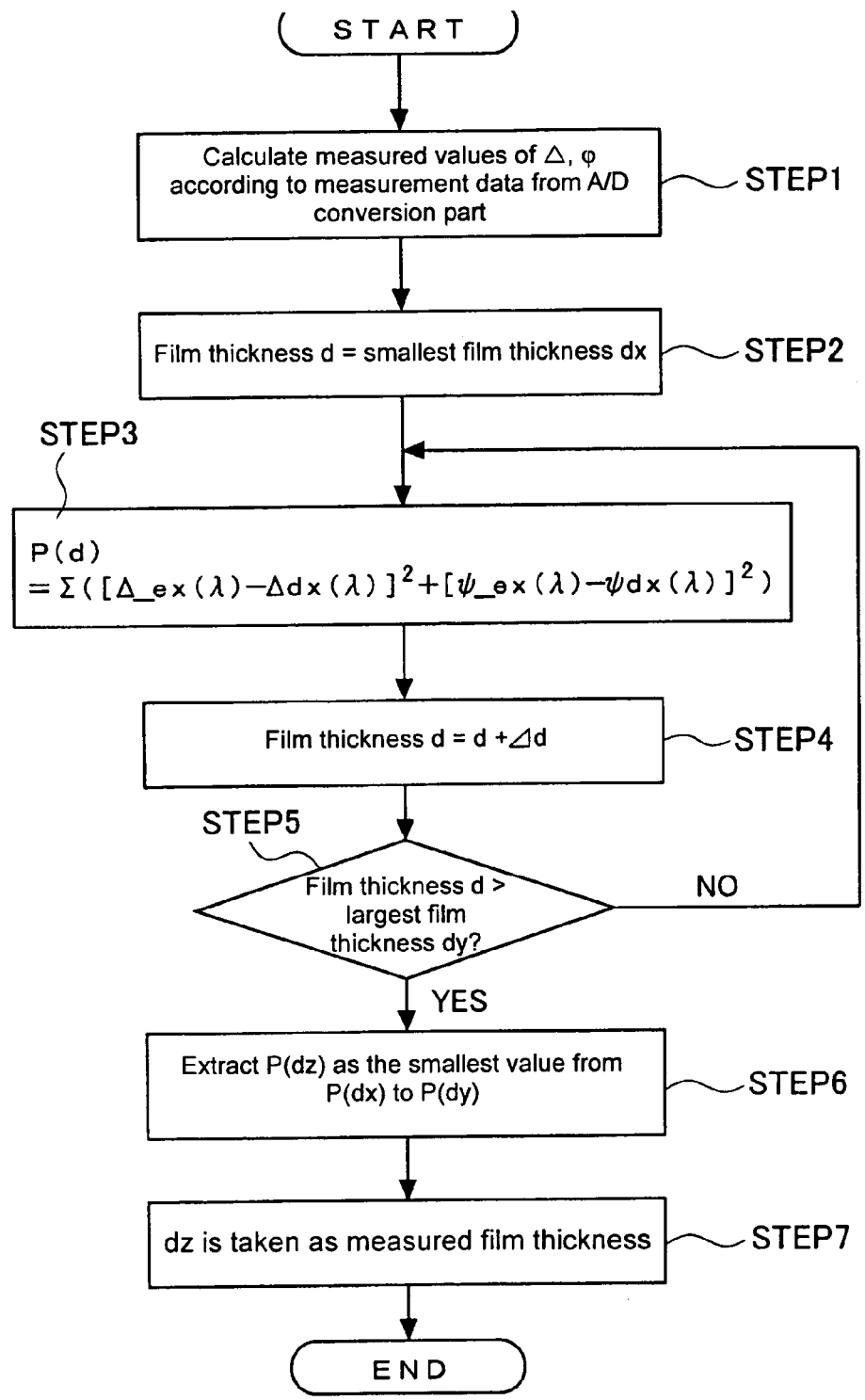
FIG. 10 shows a flowchart showing details of a film thickness measurement program.

Eventually, the expression:

$$R_p/R_s=\tan(\psi)\cdot\exp(-i\Delta) \qquad \text{Expression (9)}$$

is used to calculate respective wavelengths of $\Delta$ and $\psi$, to obtain a wavelength dependence spectrum. Then, using a thickness value d of the oxide film 701 as a parameter, the measured spectrum is compared with a theoretical spectrum (table data) which is obtained after a later-described half value width correcting process for the inclined film, so that the film thickness value d can be calculated. $R_p$ and $R_s$ are derived with the thin film restricted to a single-layered film in FIG. 6. However, as shown in FIG. 7, a theoretical expression corresponding to a multi-layered film is also capable of derivation, whereby it is possible to measure a thickness and a reflective index of a multi-layered film.

As a film-thickness arithmetic processing method in the CPU 31 of the arithmetic processing part 3, a curve fitting method can be used. The curve fitting method comprises the steps of: comparing waveform data (table data) on theoretical values of a phase difference $\Delta$ and an amplitude ratio $\psi$ after performance of a later-described inclined film half value width correcting process with respect to each film thickness, which was previously calculated and stored as a table, and waveform data on measured values of the phase difference $\Delta$ and the amplitude ratio $\psi$, which was calculated from measured data on a light-receiving amount; extracting data having a smallest error by the least-squares method; and obtaining a film thickness of the waveform data as a thickness of a thin film to be measured. Another usable film-thickness arithmetic processing method may be a method such as an extreme value searching method or a film-thickness calculating method for weighting the phase difference $\Delta$ and the amplitude ratio $\psi$.

When a reflective index n of a thin film to be measured, $r_0$ and $r_1$ are previously inputted from the input/output part such as the keyboard, the arithmetic part performs an arithmetic operation on values of the phase difference $\Delta$ and the amplitude ratio $\psi$ with respect to each value of the film thickness d and the wavelength $\lambda$, at the incident angle $\theta$, and the obtained value is held as a table in a memory in the arithmetic part. FIGS. 8 and 9 show examples of such a table.

Next, the curve fitting is specifically described. First, the CPU 31 acquires measurement data digitalized by the A/D conversion part 33, to calculate measured values of a phase difference $\Delta ex$ ($\lambda$) and an amplitude ratio $\psi ex$ ($\lambda$) (STEP 1). Next, the film thickness d is made the smallest film thickness dx (STEP 2), and using the theoretical tables of FIGS. 8 and 9, a square of a difference between theoretical values (film thickness d=dx) of the phase difference $\Delta dx$ ($\lambda$) and the amplitude ratio $\psi dx$ ($\lambda$) and measured values of the phase difference $\Delta ex$ ($\lambda$) and the amplitude ratio $\psi ex$ ($\lambda$), [$\Delta ex$ ($\lambda$)−$\Delta dx$ ($\lambda$)]$^2$ +[$\psi ex$ ($\lambda$)−$\psi dx$ ($\lambda$)]$^2$, is calculated in the wavelength range of $\lambda_p$ to $\lambda_q$ in units of $\Delta\lambda$. A sum of the squares is obtained using the following valuation expression (STEP 3):

Valuation expression $P(d)=\Sigma([\Delta ex\ (\lambda)-\Delta dx\ (\lambda)]^2 + [\psi ex\ (\lambda)-\psi dx\ (\lambda)]^2)$, and then stored into the memory. It is to be noted that the valuation expression P(d) in the fitting may be different from the one shown above so long as expressing differences between theoretical values and measured values.

As thus described, values of the film thickness d are sequentially increased by $\Delta d$ until reaching the largest film thickness dy (STEP 5). At that time, a sum of squares of difference in film thickness between theoretical data and measured data is obtained (STEP 3), and then stored into the memory.

Upon completion of the above-mentioned calculation of the sum of squares performed until the film thickness reaches the largest film thickness dy (in the case of YES in STEP 5), a sum of squares P(dz), taking the smallest value, out of the sums of squares P(dx) to P(dy) in the film thickness range of dx to dy having been stored into the memory is extracted (STEP 6), and the film thickness dz at that time is taken as a measurement film thickness (STEP 7)

In the above-mentioned case, the use of an opaque substrate was assumed and reflection from the back face of the substrate was thus not considered. When the use of a transparent substrate is assumed, however, it is necessary to consider reflection from the back face of the substrate. In such a case, as shown in FIG. 6, a theoretical expression is also capable of derivation, and hence it is possible by using this theoretical expression to perform measurement of a thickness and quality of a multi-layered film in the transparent substrate as in the above-mentioned case. However, symbol r in the FIG. 6 denotes a reflected light r shown in FIG. 5.

Figure 11:
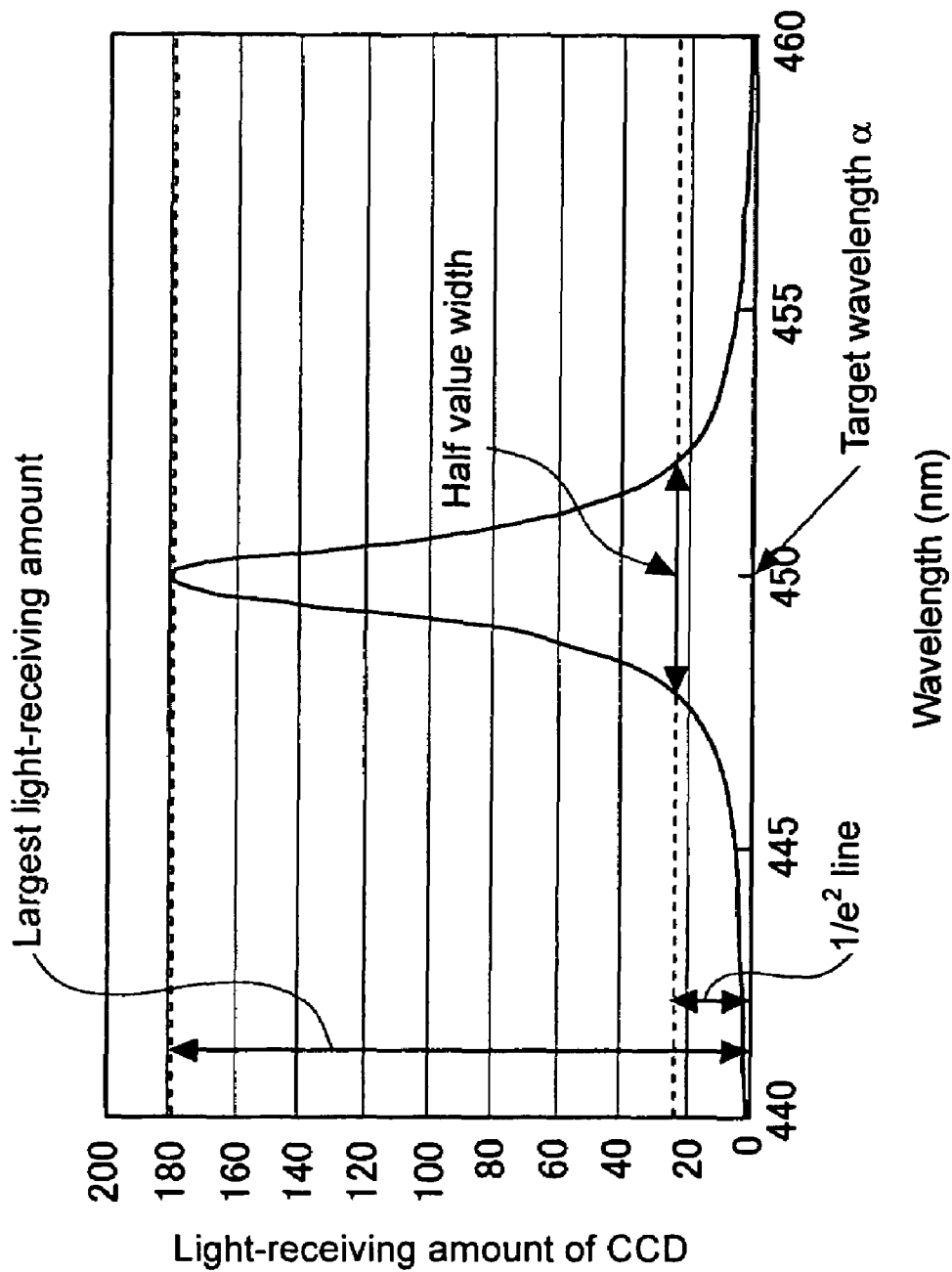
FIG. 11 shows a graph showing a relation between a light-receiving intensity spectrum and a half value width.
Figure 12:
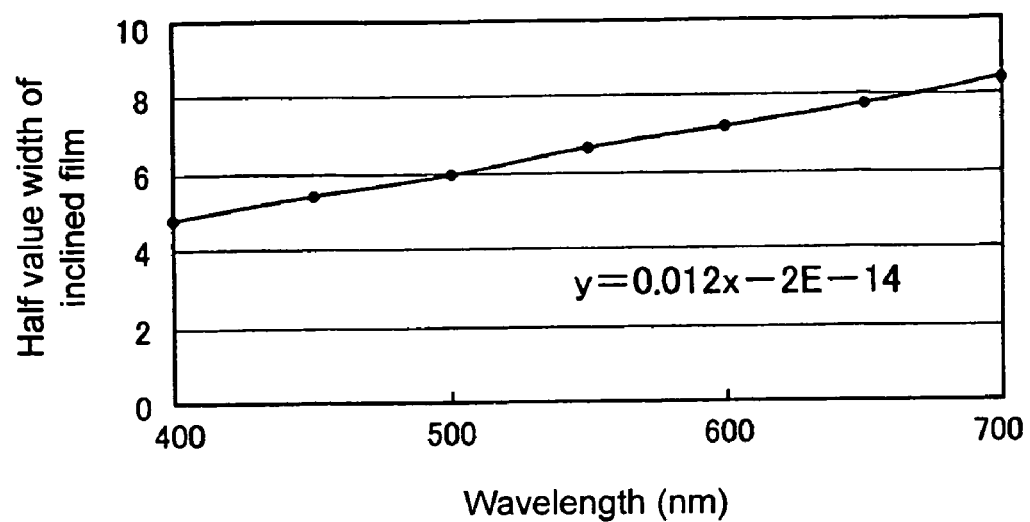
FIG. 12 shows a graph showing a relation between a wavelength and a half value width of an inclined film.

Here described is the inclined film to be used in the present invention. For example, FIG. 11 shows a light-receiving wave form when light with the wavelength of 450 nm is incident on the inclined film and received on the one-dimensional CCD. Namely, the light-receiving wave form has a half value width h to some degree due to an error of wavelength resolution. The half-value width h shows a width at the height (on the line in the figure) of the largest light-receiving amount. As shown in FIG. 12, the half-value width h has a wavelength characteristic as a characteristic of the inclined film. As a result, a process is necessary for correcting an error of the wave length resolution of the inclined film when theoretical values and measured values are compared to obtain a film thickness. This process is referred to as "half value width correction".

Next, a method for creating tables shown in FIGS. 8 and 9 is described. A method for correcting half value widths of theoretical values of phase difference Δ and the amplitude ratio ψ is described as follows. First, using the following expressions (10) to (12), Stokes parameters $S_1, S_2, S_3$ prior to correction are obtained. It is to be noted that the following expressions are general ones to be used in the rotating retarder method.

$S_1 = -\cos 2\psi$   Expression (10)

$S_2 = \sin 2\psi \cos \Delta$   Expression (11)

$S_3 = -\sin 2\psi \sin \Delta$   Expression (12)

Figure 13:
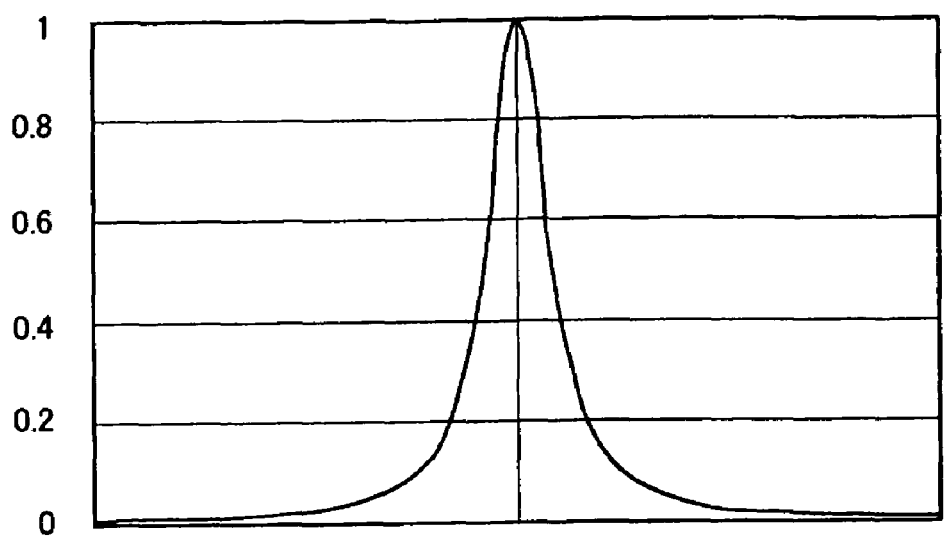
FIG. 13 shows a graph showing the Lorentz function.

$S_1, S_2, S_3$ prior to correction are weighted with respect to every target wavelength α of the light-receiving amount data by means of the half value width h of the inclined film shown in FIG. 12 and the Lorentz function f(x) shown in FIG. 13. Here, x indicates an arbitral wavelength of the light-receiving amount data. Expressions for calculating $S_1, S_2, S_3$ after correction are indicated as follows. It is to be noted that, although the error of the wavelength resolution of the inclined film is corrected here by using the Lorentz function, another method may be applied so long as being a method for correcting an error of wavelength resolution of an inclined film.

[Expression 3]

$$S1(\alpha) \text{ after correction} = \int_a^b \frac{S1(x) f(x, h)}{\int_a^b f(x, h) dx} dx \quad \text{Expression (13)}$$

$$S2(\alpha) \text{ after correction} = \int_a^b \frac{S2(x) f(x, h)}{\int_a^b f(x, h) dx} dx \quad \text{Expression (14)}$$

-continued $$S3(\alpha) \text{ after correction} = \int_a^b \frac{S3(x) f(x, h)}{\int_a^b f(x, h) dx} dx \quad \text{Expression (15)}$$

∗Lorentz function $$f(x, h) = \frac{1}{\pi} \times \frac{\beta}{\beta^2 + (x - \alpha)^2}$$

$$\beta = \frac{h}{2\sqrt{e^2 - 1}}. \quad \alpha \text{ is a target wavelength}$$

where the range of fitting wavelength is a(nm) to b(nm).

Figure 14:
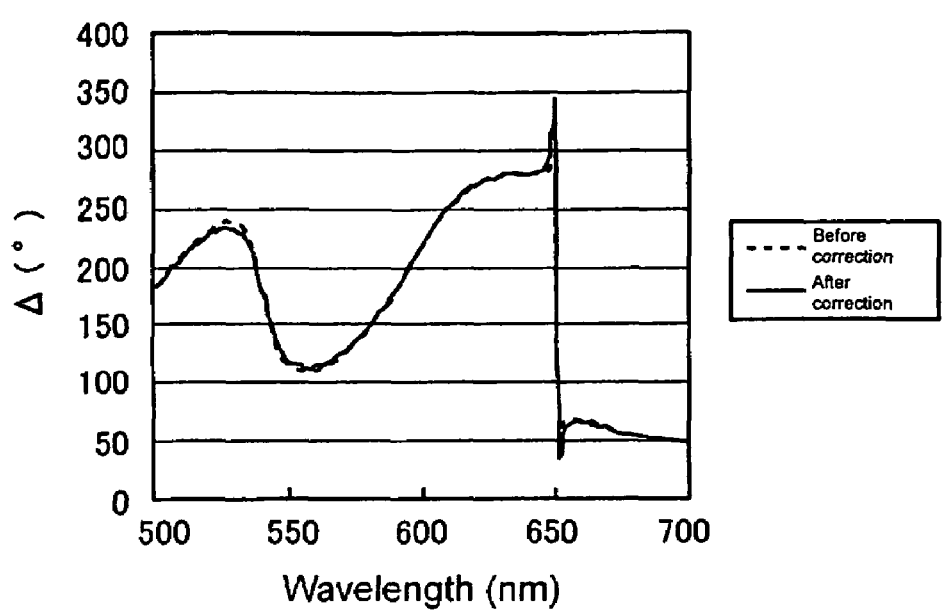
FIG. 14 shows a graph showing relations between a wavelength and a phase difference before/after correction.
Figure 15:
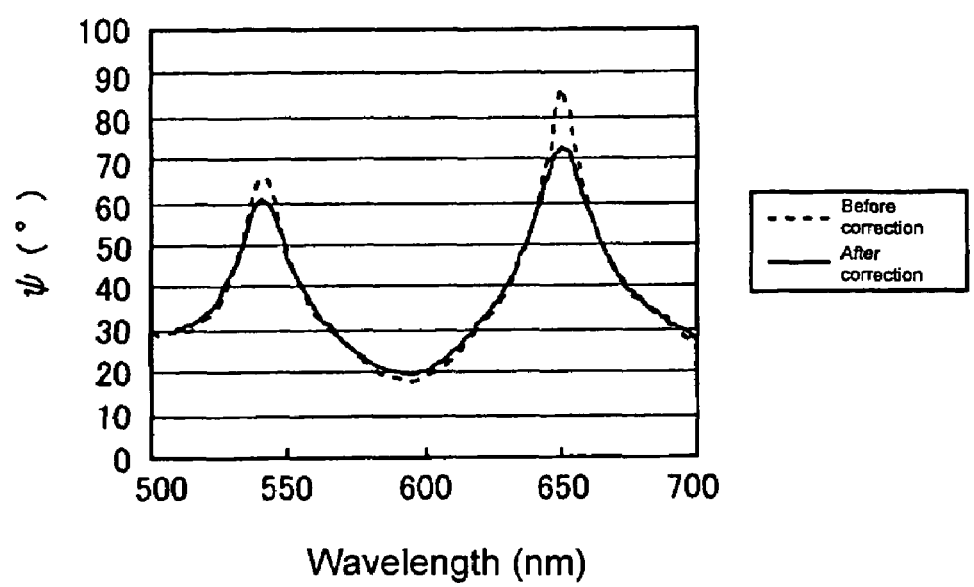
FIG. 15 shows a graph showing relations between a wavelength and an amplitude ratio before/after correction.

Theoretical values of the phase difference Δ and the amplitude ratio ψ are again calculated from the Stokes parameters $S_1, S_2, S_3$ after correction obtained above, according to the expressions (10) to (12), and the obtained values are stored as table data into the memory. FIGS. 14 and 15 show results of the half value width correction.

It should be noted that there are applications in the present embodiment as follows. Those are also applicable to later-described Embodiments 2 to 9.

(Application 1)

As the light source, an LED other than the white light source can be used. With the use of a plurality of LEDs, it is possible to realize a broad wavelength band, equivalent to the wavelength of the white light source, so as to significantly extend a life span as the light source, thereby leading to improvement in maintenance performance of the instrument of the present invention, which thus becomes more effective for the in-line measurement.

(Application 2)

Considered here is the case of using a two-dimensional CCD, other than the one-dimensional CCD, as the photoelectric transfer part array means. The incident angle hardly changes and the wavelength changes in the one-dimensional CCD, whereas the incident angle and the wavelength change independently from one another in the two-dimensional CCD. Namely, in the case of the two-dimensional CCD, an amount of information is larger and thereby enables accurate measurement.

Embodiment 2

An embodiment of a spectroscopic ellipsometer with a measure against the distance fluttering incorporated therein is specifically described while referring to FIGS. 16 to 26. It is to be noted that a configuration view showing the whole of a single incident angle spectroscopic ellipsometer, an electric configuration of an arithmetic processing part, and a basic operation for film-thickness measurement in the present embodiment are the same as shown in Embodiment 1 by reference to FIGS. 1, 3 and the like.

FIG. 16 shows an optical configuration of the sensor head part 2 with the measure against the distance fluttering incorporated therein. As shown in this figure, the ellipsometer 1 has a light-projecting optical system and a light-receiving optical system.

The light-projecting optical system includes: a light source (white light source in the illustrated example) 301; a collimator lens 302 for adjusting light emitted from the light source 301 into collimator light; an polarizer 303 for allowing only some polarized component in the collimator light launched from the collimator lens 302 to pass; a retarder 304 for retarding the phase of the light launched from the polarizer 303 by a quarter of light wavelength; a driving means 305 for rotating the retarder 304; and a condenser lens 306 for condensing the light after passage through the retarder to apply the light on a film-thickness measuring point of the thin film 5a of the substrate (sample) 5.

The light-receiving optical system comprises: a collimator lens (light-receiving lens) 308 for receiving reflected light of the measuring medium light applied on the substrate 5 and converting the light into collimator light; an analyzer 309 for allowing only some polarized component of the collimator light launched from the collimator lens 308 to pass; an inclined film 311 as a light-interference type spectroscopic element for gradually changing a transparent wavelength according to each position in the longitudinal direction; and a photoelectric transfer part array means (corresponding to one-dimensional CCD 310 in the illustrated example) formed by arranging a large number of photoelectric transfer parts in arrayed form in a direction perpendicular to the incident face (direction perpendicular to paper face). The inclined film 311 is in the state of being attached to the light-receiving face of the one-dimensional CCD 310 constituting the photoelectric transfer part array means, and oriented such that the longitudinal direction thereof matches the direction of a pixel line of the one-dimensional CCD 310.

Additionally, a distance between the lens included in the light-receiving side optical system (corresponding to the light-receiving lens in the illustrated example) and the light-receiving face of the photoelectric transfer part array means (corresponding to the one-dimensional CCD) is set so as to almost agree with a focal distance (f) of the lens.

A series of light-receiving amount data obtained from each photoelectric transfer part of the photoelectric transfer part array means is sent to an arithmetic means (corresponding to the arithmetic processing part 3 in the illustrated example), to obtain the thickness of the thin film 5a to be measured.

Main characteristics of the sensor head part of the present embodiment include: [1] adoption of a spectroscopic ellipsometer for use in the rotating retarder method; [2] adoption of an interference type spectroscopic element (inclined film) as the spectroscopic means; [3] arrangement of the one-dimensional CCD at a rear focal distance from the light-projecting lens; and [4] arrangement of a retarder in the light-projecting side optical system. Since [1], [2] and [4] are the same as shown in Embodiment 1, the descriptions thereof are left out.

In the following, the characteristics of [3] are specifically described. The characteristics of [3] are basically that: (1) the light-receiving lens 308 is in parallel with the light-receiving face of the one-dimensional CCD 310; and (2) the distance between the light-receiving lens 308 and the light-receiving face of a photoelectric transfer part array means 310 almost agree with the focal distance f of the lens. That is to say, when it is defined that the sample (substrate 5) arranged side is front while the one-dimensional CCD 310 arranged side is rear, the position of the light-receiving face of the one-dimensional CCD 310 can be expressed as almost a rear focal position of the light-receiving lens 308. Such an arrangement allows realization of an optical system unaffected by the distance fluttering.

Figure 17:
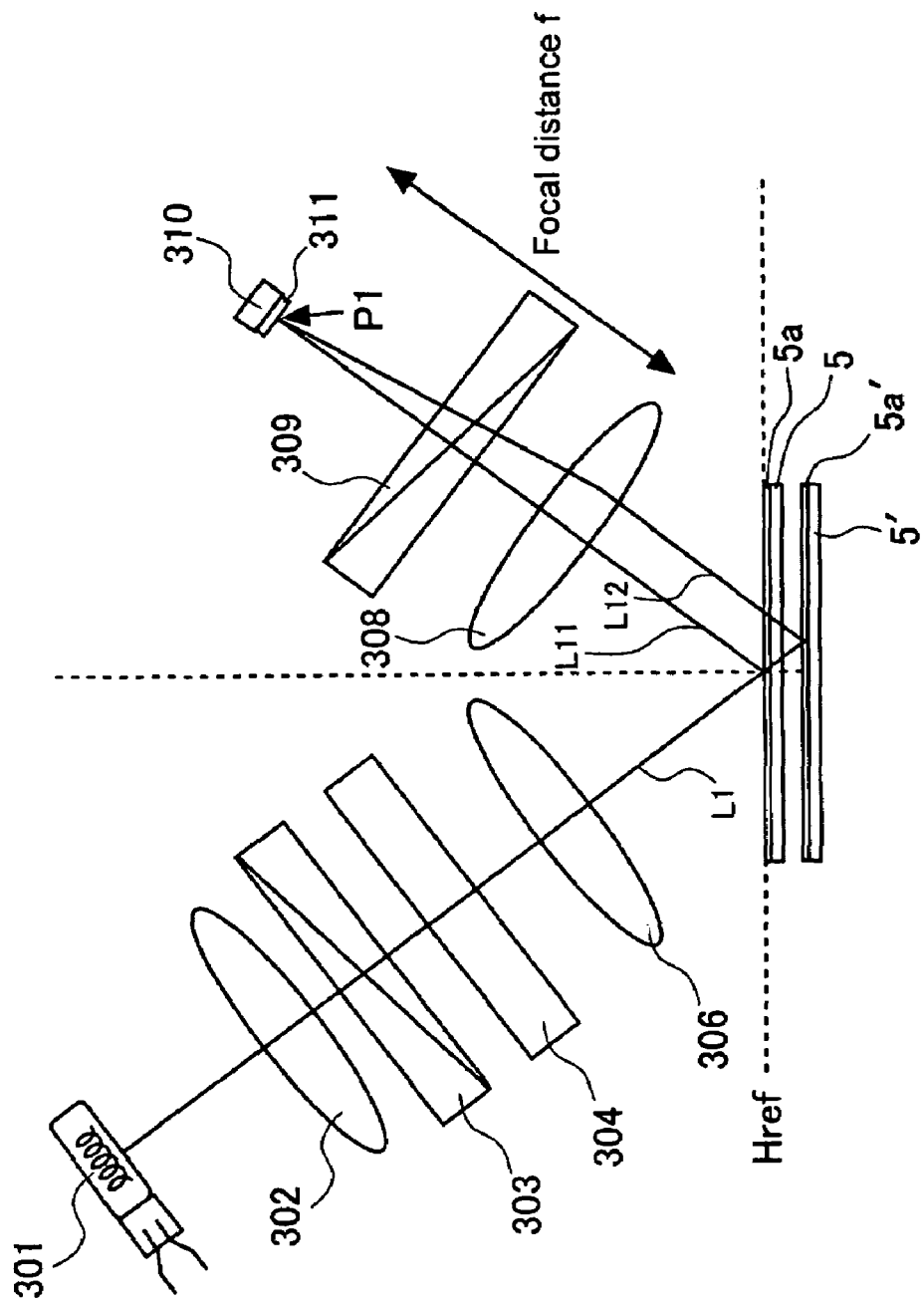
FIG. 17 shows an explanatory view of a function of a measure against distance fluttering.

FIG. 17 shows an explanatory view of the function of the measure against the distance fluttering. Here, the following are defined. A light ray that passes through a light axis out of a light flux from the condenser lens 306 is L1. A substrate when arranged at a reference height Href is numeral 5 (thin film is 5a), and the substrate when lowered due to the distance fluttering is numeral 5' (thin film is 5a'). A reflected light ray which is the light ray L1 reflected on the substrate 5, is L11, and a reflected light ray reflected on the substrate 5' is L12. An incident point of the reflected light rays L11, L12 on the light-receiving face of one-dimensional CCD 310 is P1.

As apparent from the figure, it is thus understood that the reflected light rays (L11, L12) corresponding to the uniform incident light ray L1 are incident on the identical incident point P1 on the light-receiving face of one-dimensional CCD 310 even if the substrate varies up or down due to the distance fluttering.

The foregoing function of eliminating an influence due to the distance fluttering is based upon the following principle. It is known according to the Snell's law that determination of an angle of incident light and a normal line of a sample leads to unique determination of a reflection angle.

Figure 18:
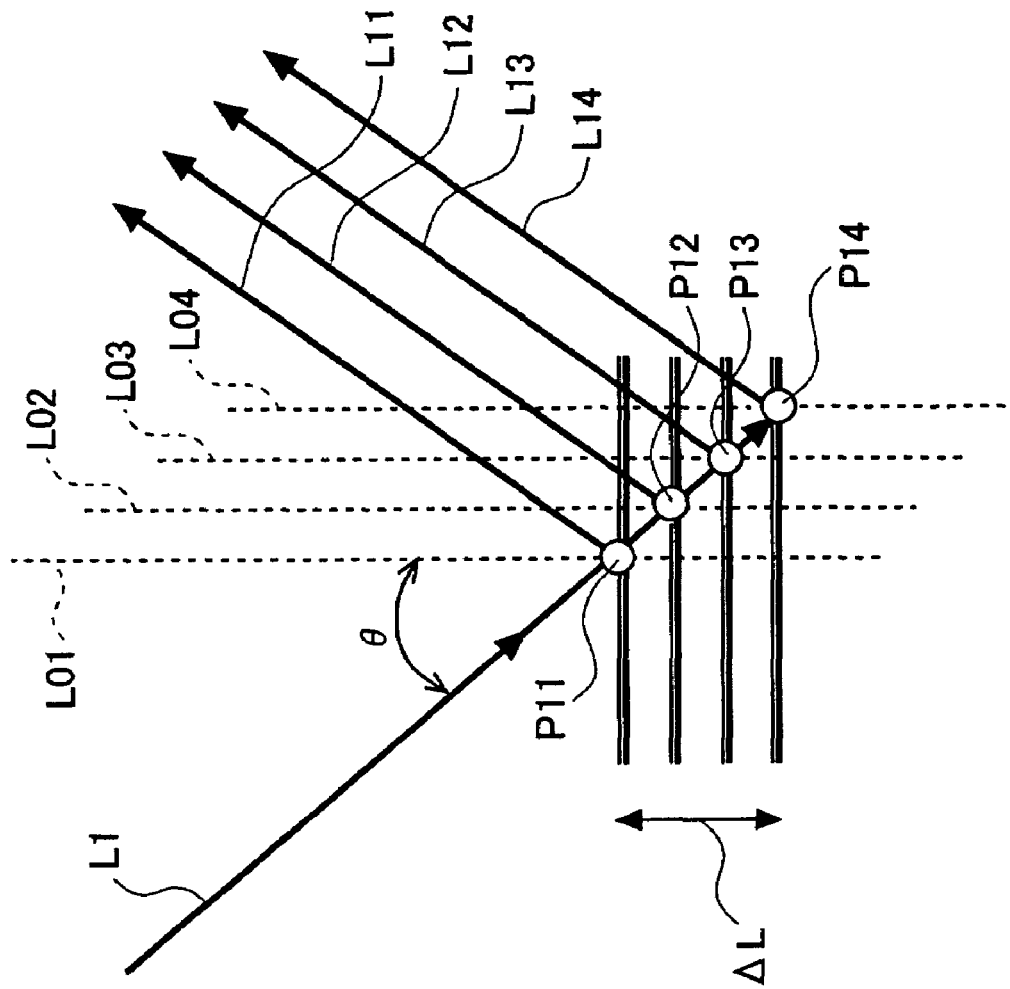
FIG. 18 shows an explanatory view of a principle of the measure against distance fluttering.

As shown in FIG. 18, considering a state where the light ray L1 is incident on the sample at the incident angle θ, it is found that, even if the up and down variation ΔL of the sample occurs due to the distance fluttering, the angle θ of incident light ray L1 and the directions of the normal lines L01, L02, L03, L04 of the sample remain unchanged, and thereby the reflection angle also remain unchanged. However, if the distance fluttering occurs, with parallel shift of the reflection surface, the reflection point shifts as shown with P11, P12, P13, P14, whereby the reflected light ray also shifts in parallel respectively to L11, L12, L13, L14.

Figure 19:
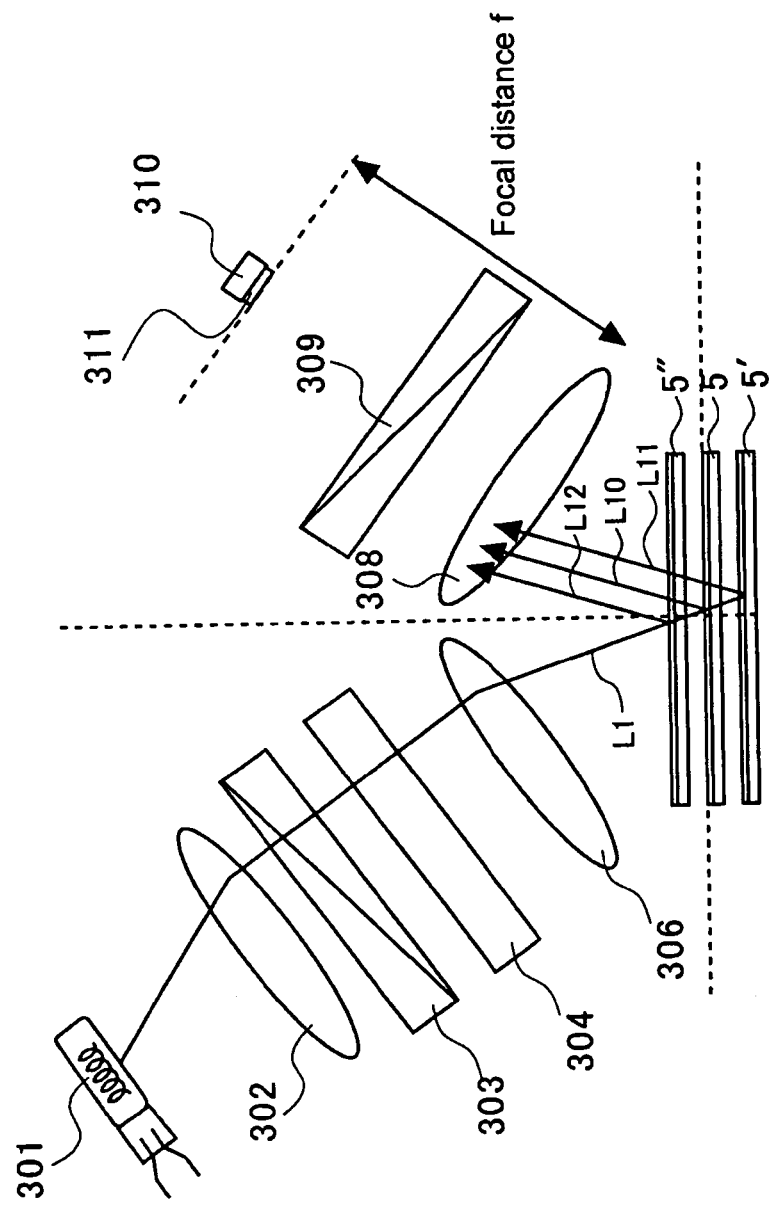
FIG. 19 shows an explanatory view showing a function of the measure against distance fluttering by incident optical path (No. 1).
Figure 20:
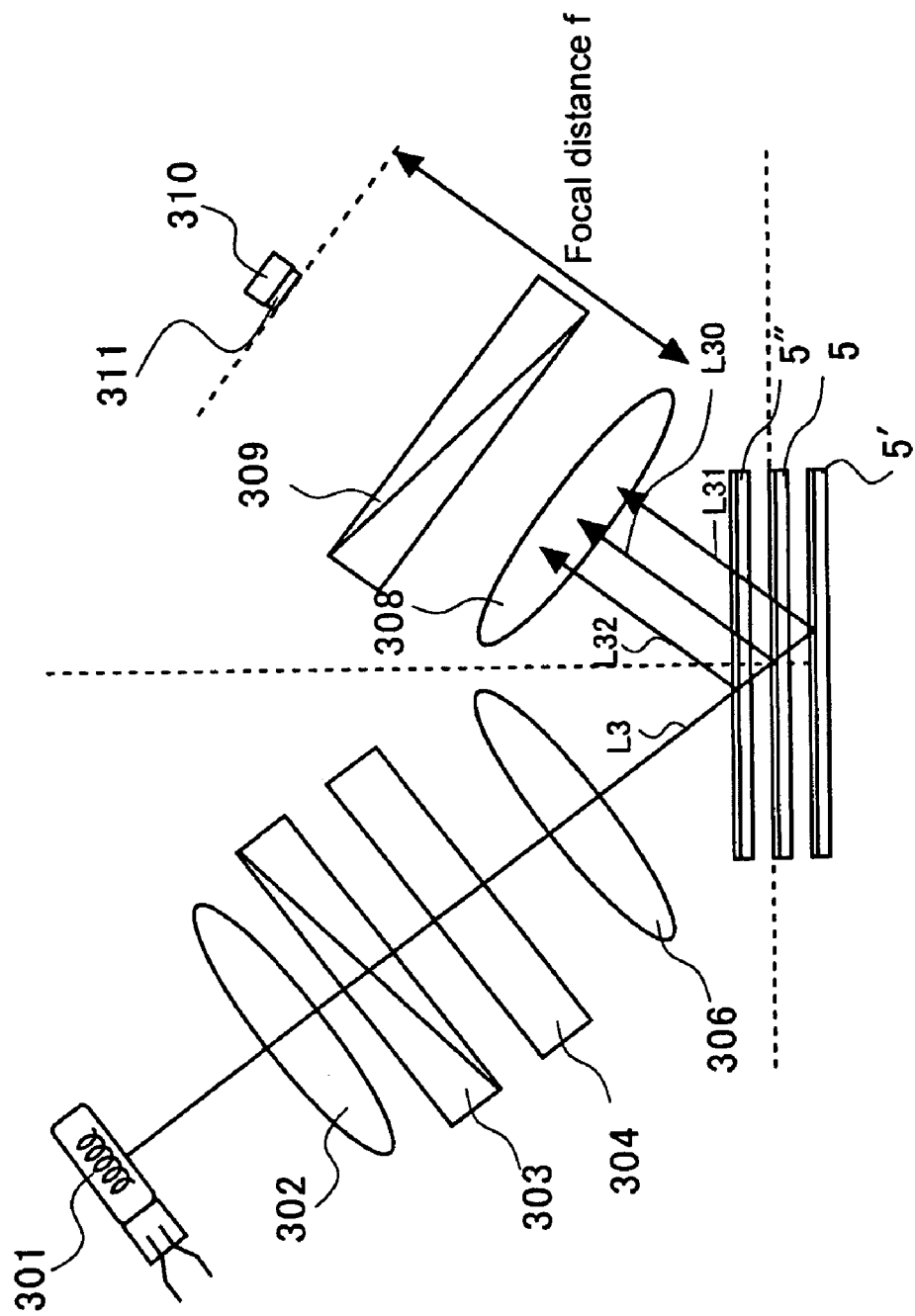
FIG. 20 shows an explanatory view showing a function of the measure against distance fluttering by incident optical path (No. 2).
Figure 21:
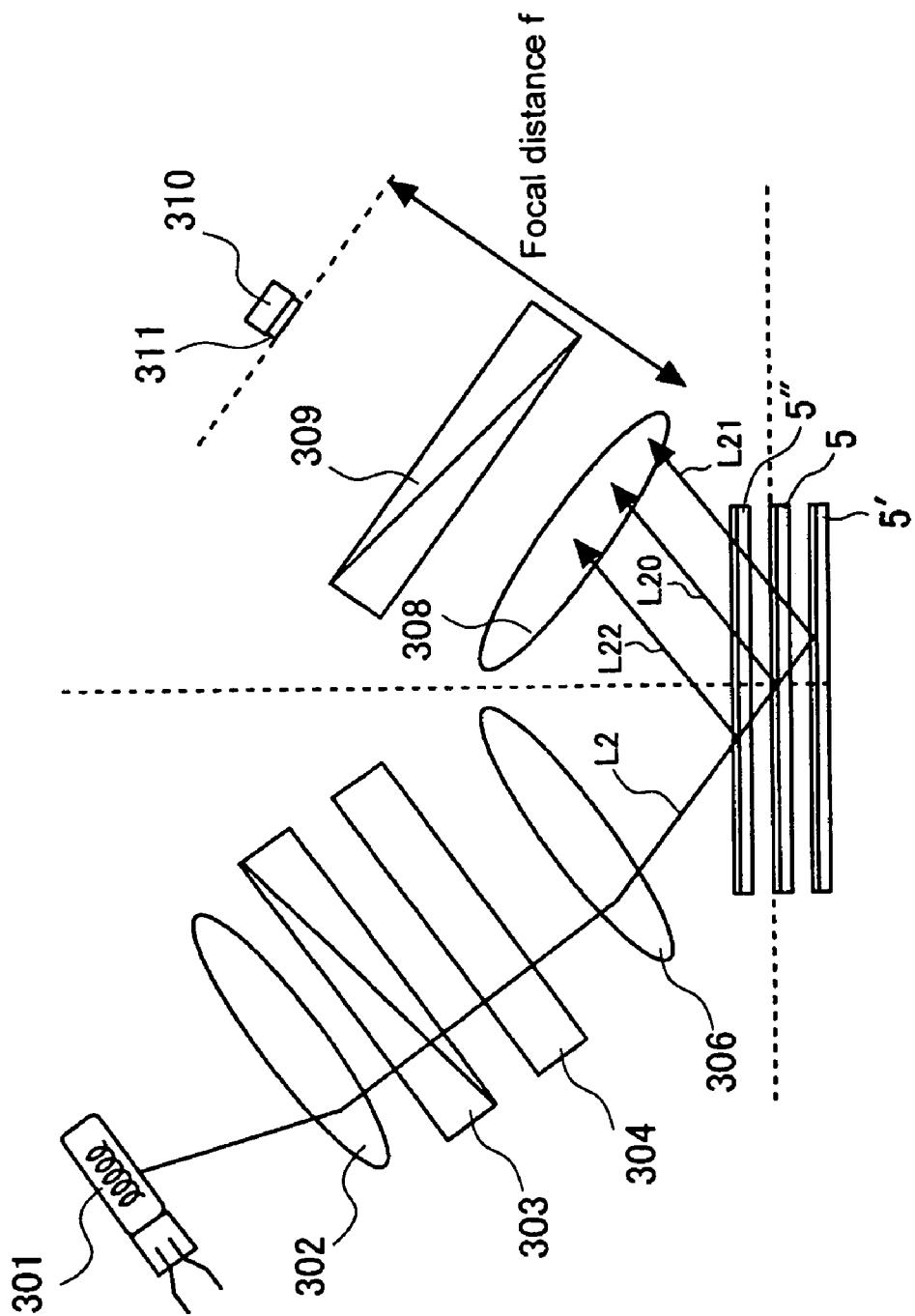
FIG. 21 shows an explanatory view showing a function of the measure against distance fluttering by incident optical path (No. 3).

Here, three incident light rays L1, L3, L2, respectively having different incident angles θ1, θ2, θ3, are assumed. At this time, if the distance fluttering (the substrate 5 at the reference height, the substrate 5' at the lowered position, the substrate 5" at the raised position) occurs, three parallel reflected light rays (L10, L11, L12), (L30, L31, L32), (L20, L21, L22) are generated with respect to each of the respective incident light rays L1, L3, L2, as shown in FIGS. 19 to 21.

Figure 22:
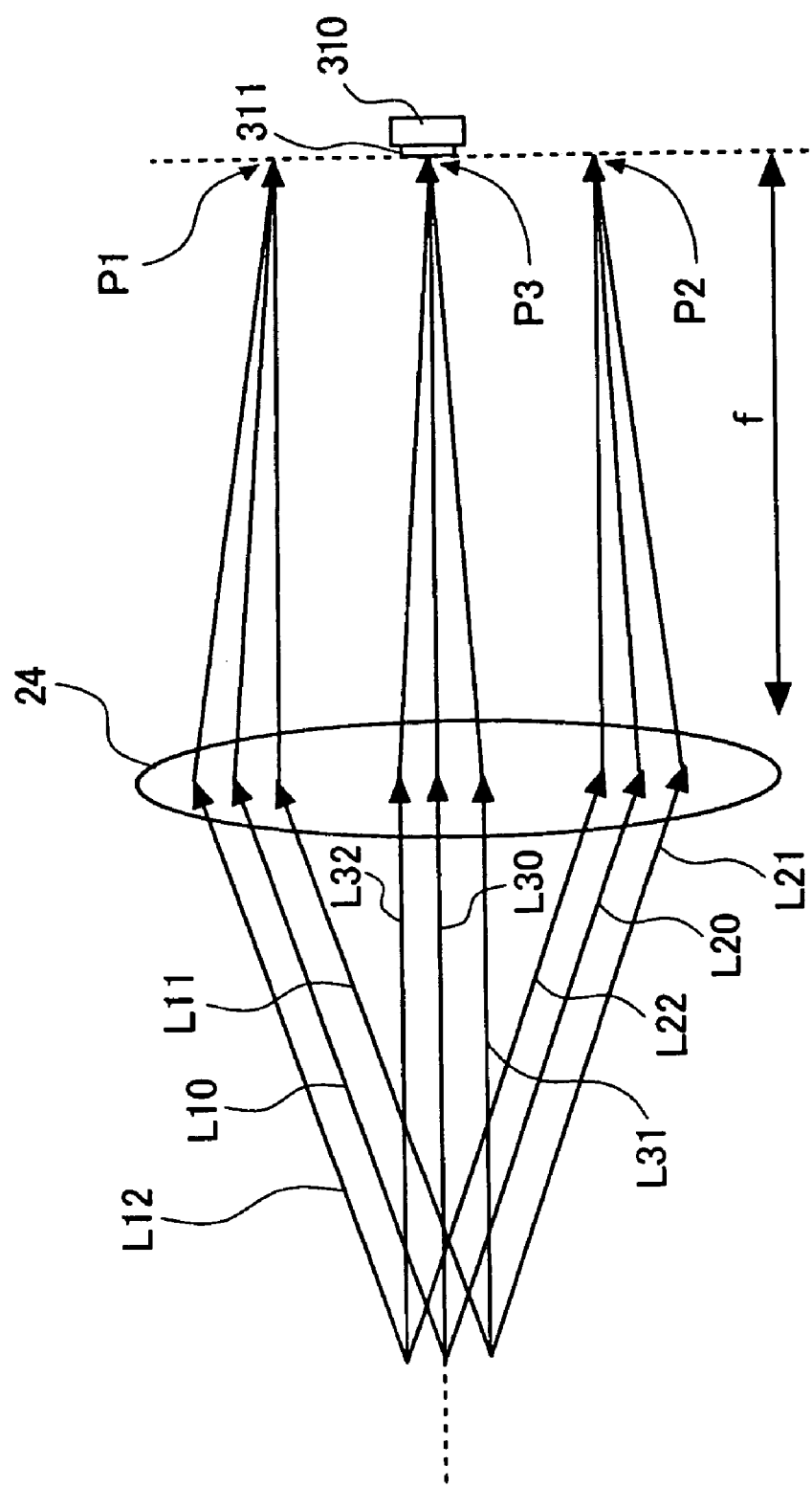
FIG. 22 shows an explanatory view showing a function of distance fluttering in a subsequent stage of a light-receiving lens.
Figure 23:
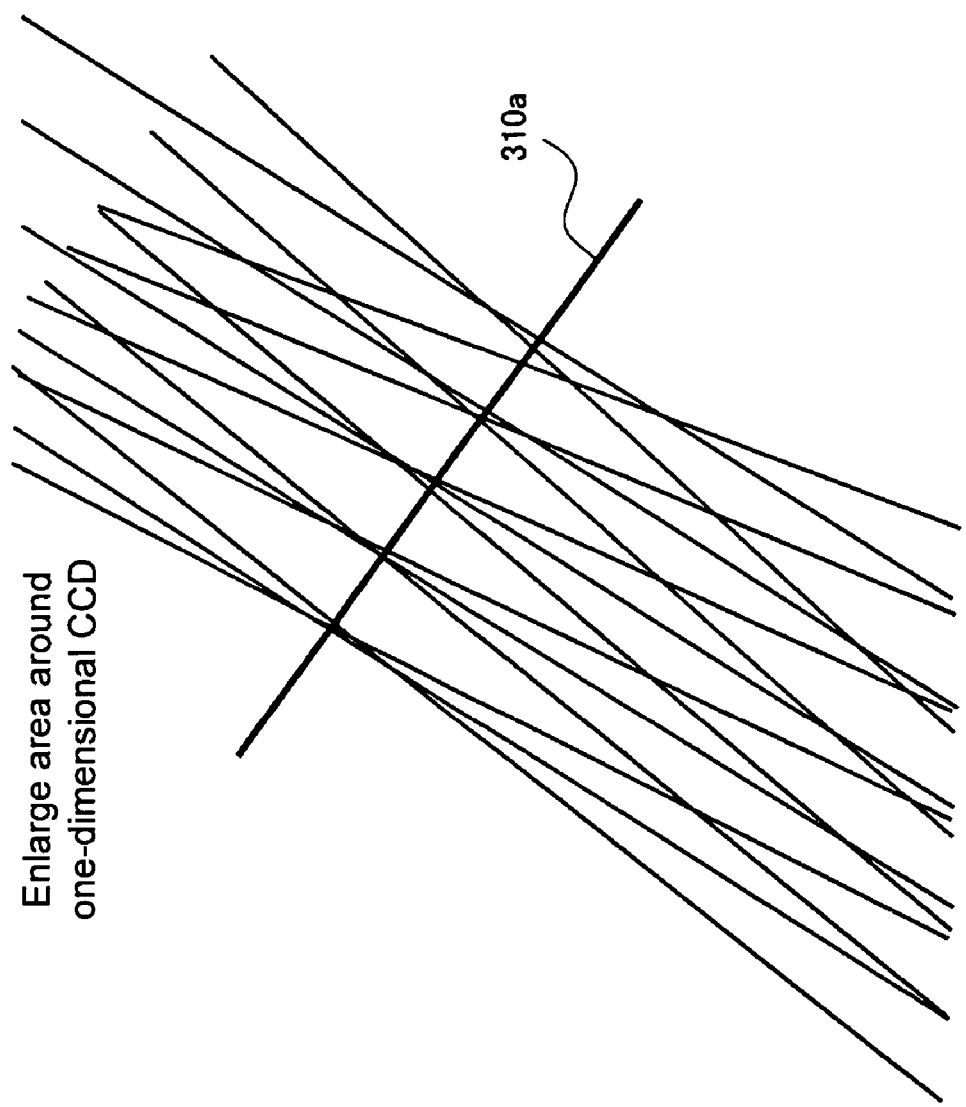
FIG. 23 shows an enlarged explanatory view showing state of light focusing around a light-receiving face of a one-dimensional CCD.

As described above, the distance between the light-receiving lens and the light-receiving face of the one-dimensional CCD is set so as to almost agree with the focal distance f of the light-receiving lens 308. Hence, as shown in FIG. 22, the three groups of parallel reflected light rays (L10, L11, L12), (L20, L21, L22), (L30, L31, L32) respectively converge on the three points P1, P2, P3 on the light-receiving face of one-dimensional CCD 310. Namely, it is understood that, even if the distance fluttering occurs, the reflected light intensity distribution according to a waveform observed through the output signal s2 from one-dimensional CCD 310 remains unchanged, and a normal film-thickness measurement is thus possible.

However, since the light-receiving lens 308 normally has an aberration, even if assuming that the light-receiving lens 308 is in parallel with the light-receiving face 310a of one-dimensional CCD 310, and the distance therebetween completely agrees with the focal distance f of the light-receiving lens, the convergence points of the parallel light rays of the respective groups do not converge on one point on the light-receiving face in the strict sense. The expression "almost agree with the focal distance f" has been used based upon the awareness of what was described above.

Figure 24:
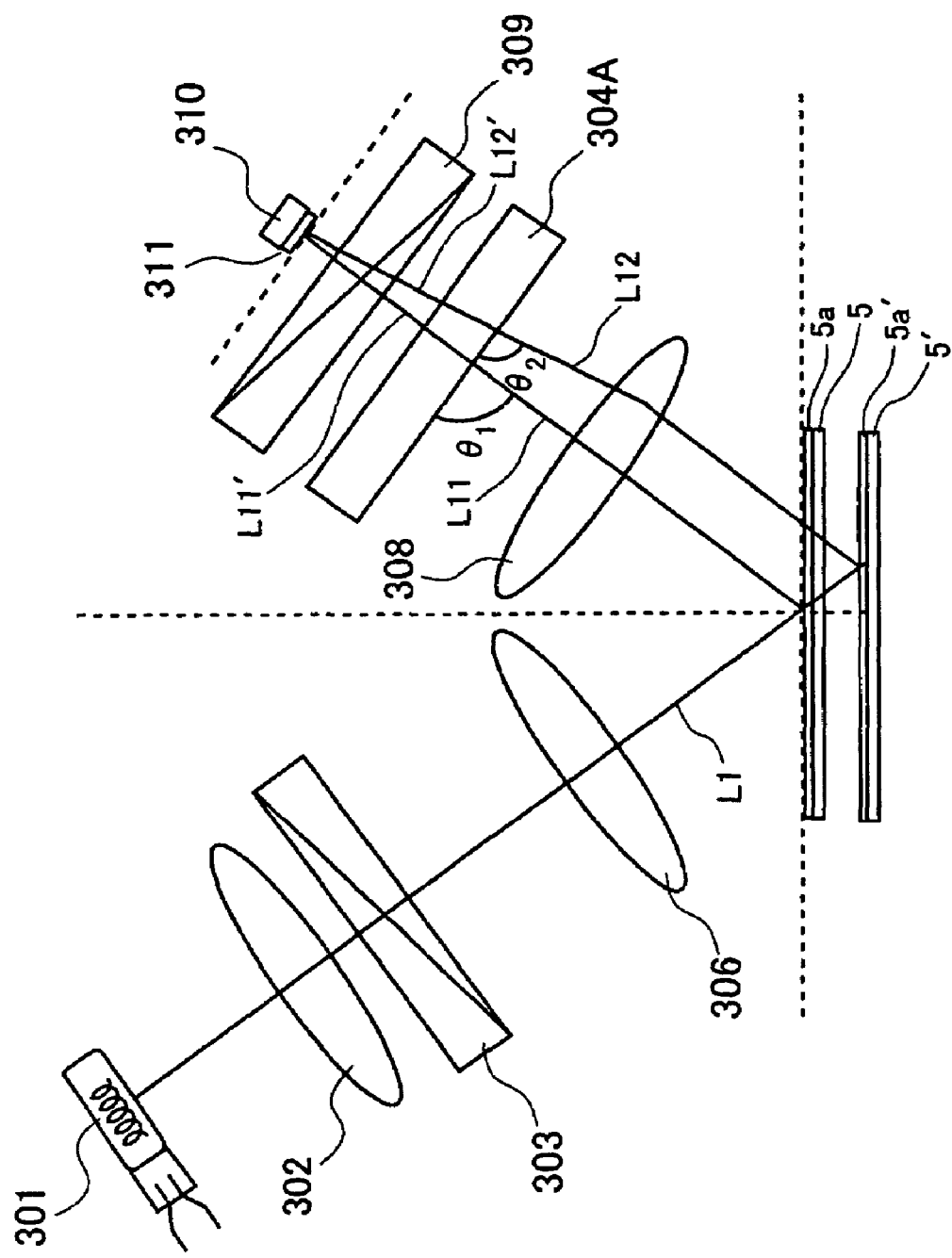
FIG. 24 shows an explanatory view of the case where distance fluttering has occurred (a retarder is in a light-receiving system).

For confirmation purpose, FIG. 24 shows the case different from the case of the present invention, where a retarder 304A is arranged in the light-receiving side optical system, and the distance fluttering occurs. Here, the following are assumed. A light ray of a light axis out of a light flux from the condenser lens 306 is defined as L1. A substrate when arranged at a reference height Href is numeral 5 (thin film is 5a), and the substrate when lowered due to the distance fluttering is numeral 5' (thin film is 5a'). A light ray immediately after the light ray L1 has been reflected on the substrate 5 and passed through the collimator lens 308 is L11, and a light ray immediately after the light ray L11 has reflected on the substrate 5' and passed through the collimator lens 308 is L12. Further, a light ray immediately after passage of the light ray L11 through the retarder 304A, and a light ray immediately after passage of the light ray L11 through the retarder 304A.

It is found from FIG. 24 that the angle θ1 at which the light ray L12 is incident on the retarder 304A is not equal to the angle θ2 at which the light ray L11 is incident on the retarder 304A. Since the retarder typically has incident angle dependency, the polarized states of L11' and L12' are different from one another. It is therefore found that an optical system with a retarder arranged in the light-receiving side optical system and resistant to the distance fluttering cannot be realized.

Figure 25:
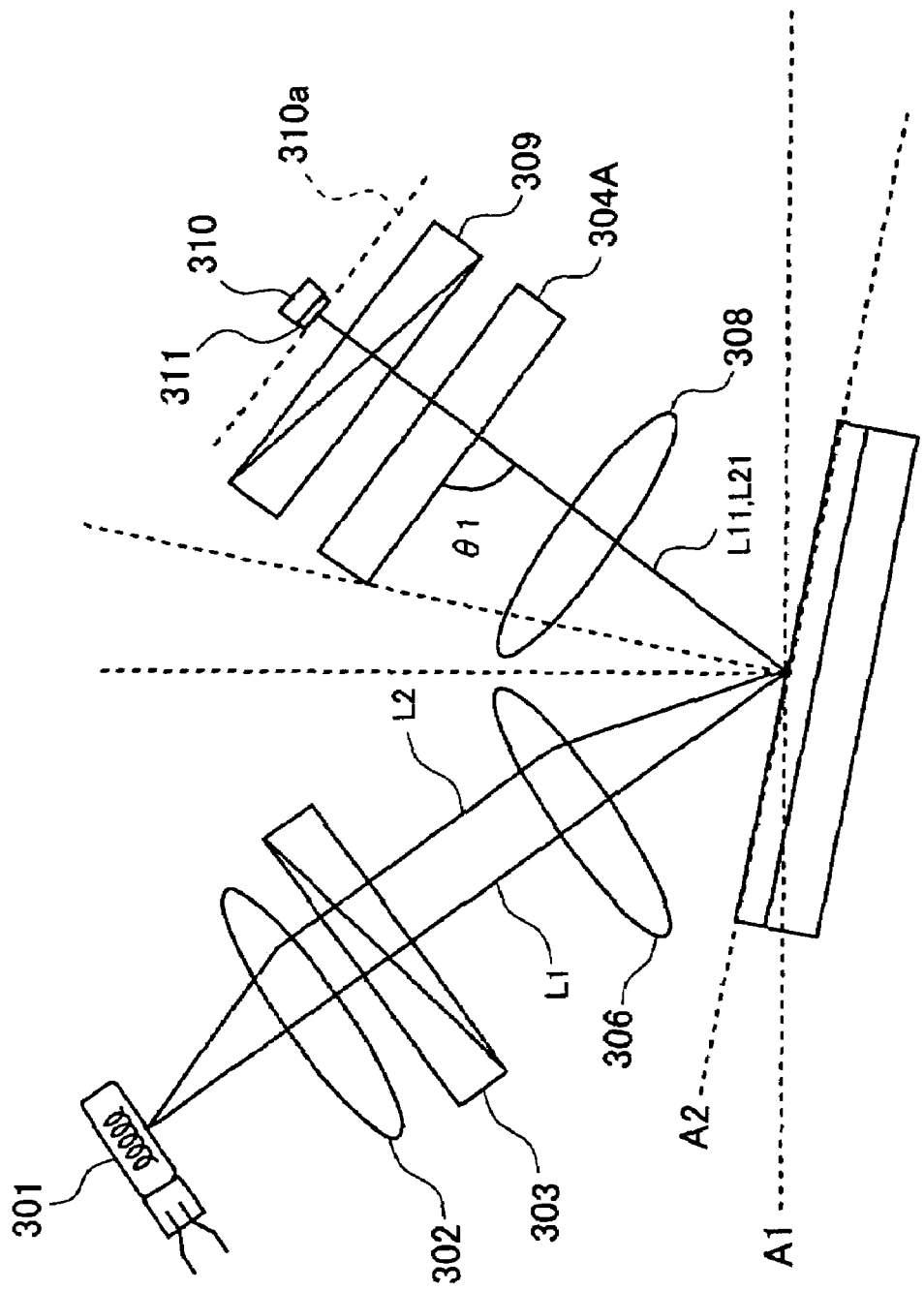
FIG. 25 shows an explanatory view of the case where angle fluttering has occurred (the retarder is in the light-receiving system).

FIG. 25 shows the case where a retarder is arranged in the light-receiving side optical system, and the angle fluttering occurs. Here, the following are assumed. A light ray incident on the CCD 310 at a reference angle A1 out of a light flux from a condenser lens is L1. A light ray incident on the CCD 310 at an angle A2 is L2. A light ray reflected on the substrate 5 on which the light ray L1 is incident at the reference angle A1 is L11. A light ray reflected on the substrate 5 on which the light ray L2 is incident at the angle A2 is L21. At this time, the light L11 agrees with the light lay 21. Namely, it is found that the light ray incident on the CCD 310 when no angle fluttering has occurred agrees with the same light ray when the angle fluttering has occurred. As a result, the angles at which those light rays are incident on the retarder, as well as the polarized states of those light rays, become equal to one another. Accordingly, in the case of arrangement of the retarder 304A in the light-receiving side optical system, it is possible to realize an optical system resistant to the angle fluttering if an angle at which a light ray is incident on the CCD 310 can be calculated.

It is revealed from the above that, when the retarder 304A is arranged in the light-receiving side optical system, an optical system resistant to the distance fluttering cannot be realized although an optical system resistant to the angle fluttering can be realized. Namely, an optical system resistant to both the angle fluttering and the distance fluttering cannot be realized, whereby it is not possible to perform the in-line measurement.

Figure 26:
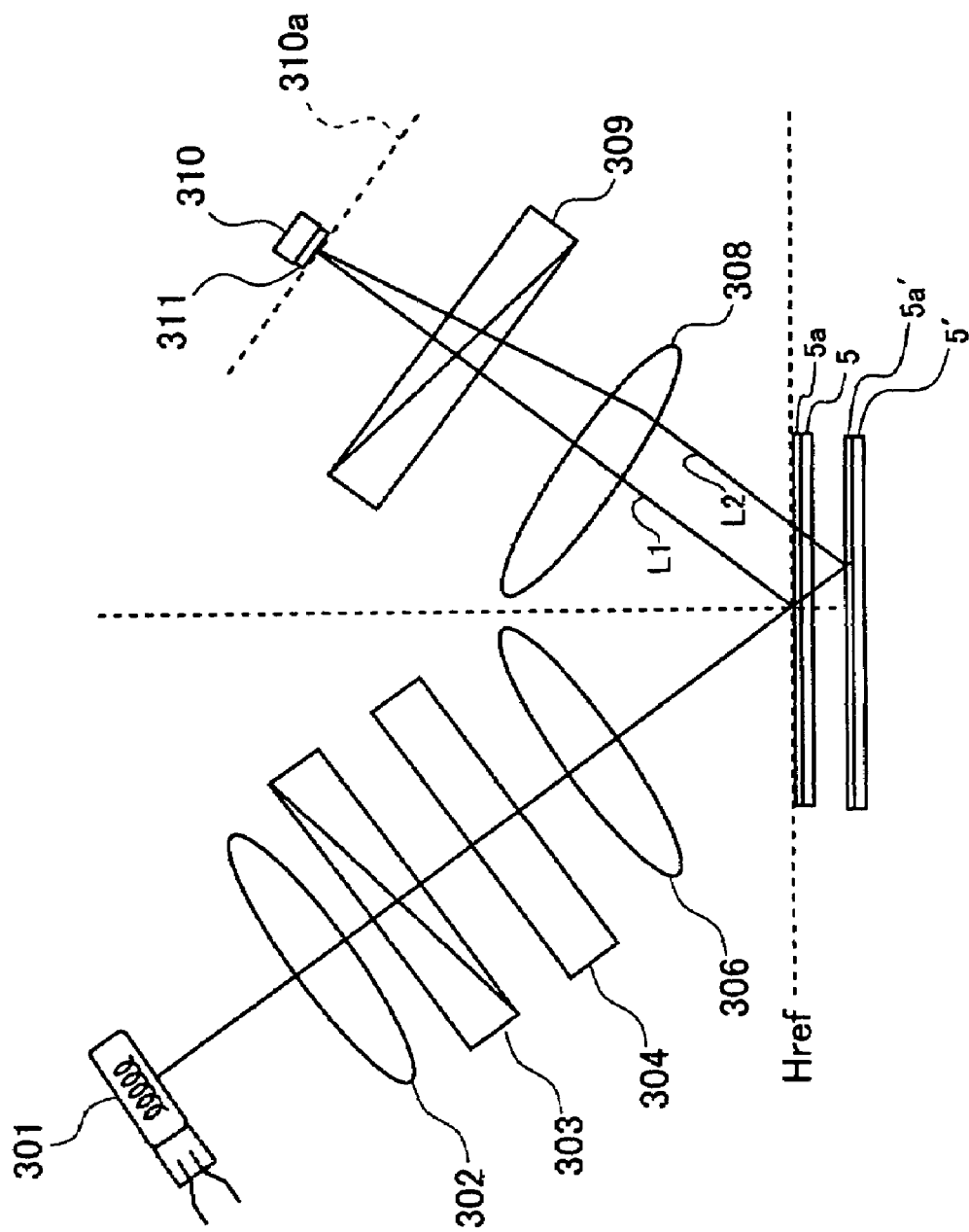
FIG. 26 shows an explanatory view of the case where distance fluttering has occurred (the retarder is in a light-projecting system).

Next, FIG. 26 shows the case where a retarder is arranged in the light-projecting side optical system, and the distance fluttering occurs. Here, the following are assumed. A substrate when arranged at a reference height Href is numeral 5 (thin film is 5a), and the substrate when lowered due to the distance fluttering is numeral 5' (thin film is 5a'). A light ray of a light axis out of a light flux from the condenser lens 306 is defined as L1. A light ray reflected on numeral 5 is L1, and a light ray reflected on numeral 5' is L2.

It is revealed from the figure that the light ray incident on the CCD 310 when no angle fluttering has occurred agrees with the same light ray when the angle fluttering has occurred. As a result, the angles at which those lights are incident on the retarder 304, as well as the polarized states, become uniform. Accordingly, in the case of arrangement of a retarder in the light-projecting side optical system, it is possible to realize an optical system resistant to the distance fluttering. It should be noted that the applications shown in Embodiment 1 are applicable to the applications of the present embodiment.

Embodiment 3

Figure 27:
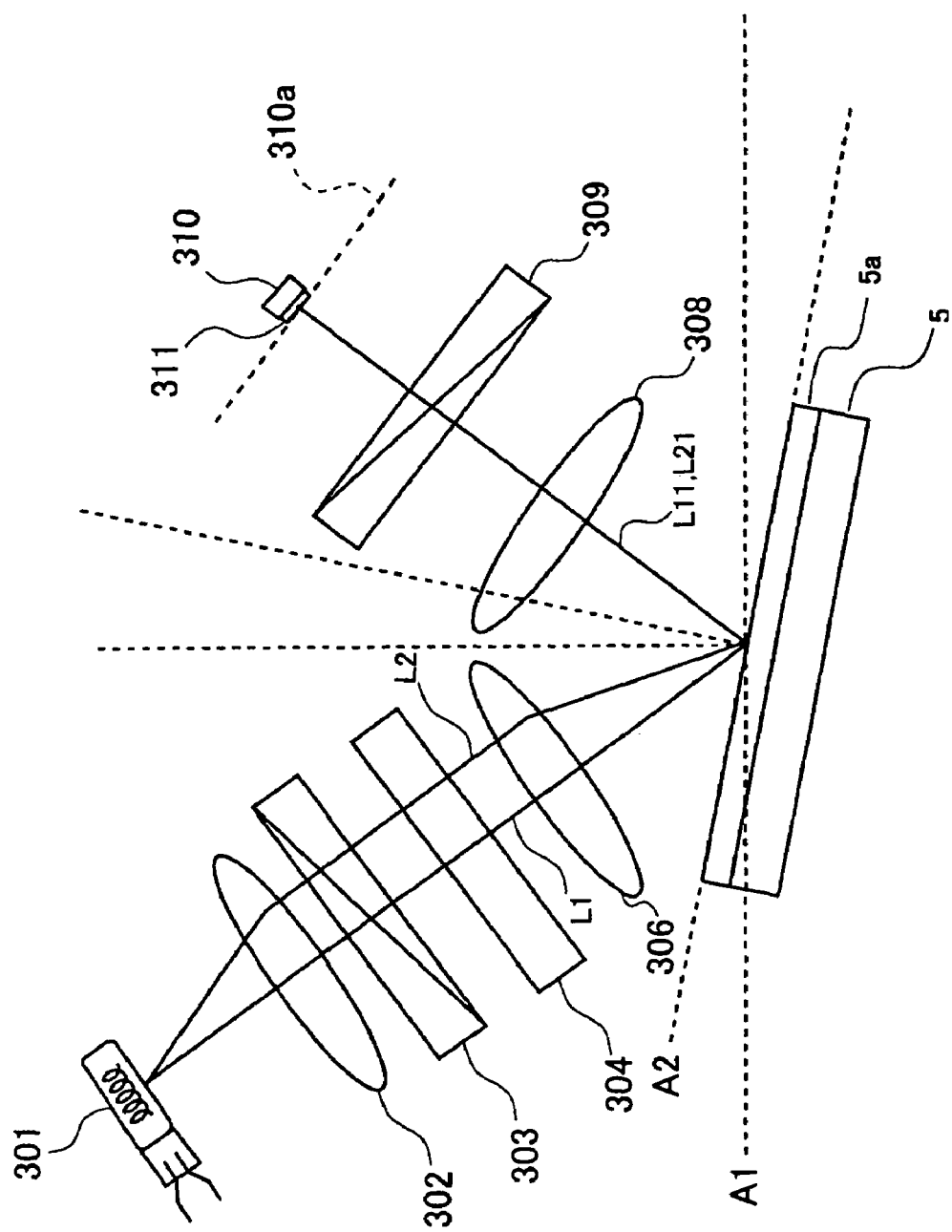
FIG. 27 shows an explanatory view of the case where distance fluttering has occurred (the retarder is in the light-projecting system).

An embodiment of an ellipsometer with a measure against the angle fluttering incorporated therein is specifically described while referring to FIGS. 27 to 29. It is to be noted that a configuration view showing the whole of a single incident angle spectroscopic ellipsometer, an electric configuration of an arithmetic processing part, and a basic operation for film-thickness measurement in the present embodiment are the same as shown in Embodiment 1 by reference to FIGS. 3, 5 and the like.

FIG. 28 shows an optical configuration of a sensor head part with a measure against the angle fluttering incorporated therein. As shown in this figure, this ellipsometer has a light-projecting optical system and a light-receiving optical system.

The light-projecting optical system includes: a light source (white light source in the illustrated example) 301; a collimator lens 302 for adjusting light emitted from the light source 301 into collimator light; an polarizer 303 for allowing only some polarized component in the collimator light launched from the collimator lens 302 to pass; a retarder 304 for retarding the phase of the light launched from the polarizer 303 by a quarter of light wavelength; a driving means 305 for rotating the retarder 304; and a condenser lens 306 for condensing the light after passage through the retarder to apply the light on a film-thickness measuring point of the thin film 5a of the substrate (sample) 5.

The light-receiving optical system comprises: a collimator lens (light-receiving lens) 308 for receiving reflected light of the measuring medium light applied on the substrate 5 and converting the light into collimator light; an analyzer 309 for allowing only some polarized component of the collimator light launched from the collimator lens 308 to pass; an inclined film 311 as a light-interference type spectroscopic element for gradually changing a transparent wavelength according to each position in the longitudinal direction; and a photoelectric transfer part array means (corresponding to one-dimensional CCD 310 in the illustrated example) formed by arranging a large number of photoelectric transfer parts in arrayed form in a direction perpendicular to the incident face (direction perpendicular to paper face). The inclined film 311 is in the state of being attached to the light-receiving face of the one-dimensional CCD 310 constituting the photoelectric transfer part array means, and oriented such that the longitudinal direction thereof matches the direction of a pixel line of the one-dimensional CCD 310.

Additionally, a distance between the lens included in the light-receiving side optical system (corresponding to the light-receiving lens in the illustrated example) and the light-receiving face of the photoelectric transfer part array means (corresponding to the one-dimensional CCD) is set so as to almost agree with a focal angle (f) of the lens.

A series of light-receiving amount data obtained from each photoelectric transfer part of the photoelectric transfer part array means is sent to an arithmetic means (corresponding to the arithmetic processing part 3 in the illustrated example), to obtain the thickness of the thin film 5a to be measured.

Further, the light-projecting side optical system includes a first characterization means (corresponding to a first slit 313A to function as an edge shaping means in the illustrated example) of characterizing variations in inclination of the sample in a direction rotating around a straight line as a central axis, the line being perpendicular to the incident face of the measured medium light, and further includes a second characterization means (corresponding to a second slit 313B to function as an edge shaping means in the illustrated example) of characterizing variations in inclination of the sample in a direction rotating around a straight line as a central axis, the line being an intersection between the incident face and a face to be measured.

Further, the light-receiving side optical system includes an inclination detecting photoelectric transfer means (one-dimensional CCD 314 in the figure) of receiving the reflected light of the measuring medium light reaching from a film thickness measuring point of the sample, to detect a characteristic in the first characterization means included in the received reflected light.

Moreover, the arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the first photoelectric transfer means, and further includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means. It is to be noted that details of the processing for the film-thickness measurement in the arithmetic processing part 3 are the same as described in Embodiment 1.

Main characteristics of the sensor head part of the present embodiment include: [1] adoption of a spectroscopic ellipsometer for use in the rotating retarder method; [2] adoption of an interference type spectroscopic element (inclined film) as the spectroscopic means; [3] arrangement of a characterization means of characterizing variations in inclination of the sample in a direction rotating around a straight line as a central axis, the line being perpendicular to the incident face; [4] arrangement of a characterization means of characterizing variations in inclination of the sample in a direction rotating around a straight line as a central axis, the line being an intersection between the incident face and a face to be measured; and [5] arrangement of a retarder in the light-projecting side optical system.

Since [1] and [2] are the same as shown in Embodiment 1, the descriptions thereof are left out. In the following, the characteristics of [3] and [4] are described. As described above, if the angle fluttering occurs in the ellipsometer of this kind, each end of the waveform in the direction of the pixel line, which is observed through the one-dimensional CCD, is displaced from its reference position. Since the arithmetic processing part cannot perform a normal waveform processing in such a state, it is necessary to accurately calculate an angle at which a light ray to be received on the one-dimensional CCD is incident on the sample, prior to the arithmetic processing for the film-thickness measurement.

As shown in FIG. 28, the characteristics of [3] and [4] relate to: (1) arrangement of a slit plate 313 to function as the edge shaping means on the incident side of the condenser lens, and edge-shaping of the cross section of the incident light, to characterize a reference light axes Lref0, Lref1 for mainly detecting the angle fluttering in the horizontal direction, and also characterize a reference light axes Lref2, Lref3 for mainly detecting the angle fluttering in the perpendicular direction; (2) detection of reaching points Pref0, Pref1 of the reference light axes Lref0', Lref1' for reflected light through the one-dimensional CCD 314; (3) detection of reaching points Pref2, Pref3 of the reference light axes Lref2', Lref3' for reflected light through the one-dimensional CCD 314; (4) correction of an error component included in an output signal s2 from the one-dimensional CCD 314, the component having been generated due mainly to the angle fluttering of the sample in the horizontal direction, based upon the detected incident points Pref0, Pref1; and (5) correction of an error component included in the output signal s2 from the one-dimensional CCD 314, the component having been generated due mainly to the angle fluttering of the sample in the perpendicular direction, based upon the detected incident points Pref2, Pref3.

The word "mainly" is used in the above descriptions because, in the case where the angle fluttering in the horizontal direction and the angle fluttering in the perpendicular direction occur, the reaching points pref0, pref1 vary in any way under the influence of the angle fluttering in the perpendicular direction, and the reaching points pref2, pref3 also vary in any way under the influence of the angle fluttering in the horizontal direction.

Namely, as shown in FIG. 29(*a*), a rectangular opening 313*a* is formed in the central part of the slit plate 313 as the edge shaping means arranged in the light-projecting optical system. An incident angle range (θ0 to θ1) is determined by the upper and lower edges 313*b*, 313*c* of the rectangular opening 313*a*, that is, the two reference light axes Lref0, Lref1 are characterized in the measuring medium light.

These two reference light axes Lref0, Lref1 are reflected on the sample to become the reference light axes Lref0', Lref1' of the reflected light, and then are incident on pixel positions Pref0, Pref1 on the light-receiving face of the one-dimensional CCD. Pixel coordinates Rref0, Rref1 of the incident points can be readily detected for example by binarizing the output signal from the one-dimensional CCD 314 with a threshold at a level equivalent to a dark level.

Therefore, the incident angles at the upper and lower edges 313*b*, 313*c* are observed through each pixel of the one-dimensional CCD 314 to measure a displacement of the pixel from the reference position, and it is thereby possible to mainly detect the angle fluttering in the horizontal direction, and also to determine an angle at which the light ray is incident on the one-dimensional CCD 314. Here, the reference position is a position of the pixel measured in the absence of the angle fluttering, as shown with Pref2, Pre3 in FIG. 28.

Similarly, the incident angle range is determined by the right and left edges 313*d*, 313*e* of the rectangular opening 313*a*, that is, two reference light axis Lref2, Lref3 are characterized in the measuring medium light.

These two reference light axes Lref2, Lref3 are reflected on the sample to become the reference light axes Lref2', Lref3' of the reflected light, and then are incident on pixel positions Pref2, Pref3 on the light-receiving face of the one-dimensional CCD 310. Pixel coordinates Rref2, Rref3 of the incident points can be readily detected for example by binarizing the output signal from the one-dimensional CCD 310 with a threshold at a level equivalent to a dark level.

Therefore, the incident angles at the right and left edges 313*d*, 313*e* are observed through each pixel of the one-dimensional CCD 310 to measure a displacement of the pixel from the reference position, and it is thereby possible to mainly detect the angle fluttering in the perpendicular direction, and also to determine an angle at which the light ray is incident on the one-dimensional CCD 310. Here, the reference position is a position of the pixel measured in the absence of the angle fluttering, as shown with Pref2, Pref3 in FIG. 28.

In the case where the angle fluttering in the horizontal direction and the angle fluttering in the perpendicular direction occur, each of the reaching points Pref0, Pref1, Pref2, Pref3 are affected by the angle fluttering in the horizontal direction and the angle fluttering in the perpendicular direction.

In the following shown is a method for calculating an angle at which a light ray to be received on one-dimensional CCD 310 is incident on the sample in the case where the angle fluttering in the horizontal direction and the angle fluttering in the perpendicular direction occur.

When it is defined that the angle fluttering in the horizontal direction is θ1, the angle fluttering in the perpendicular direction is θ2, a displacement of the pixel from its reference position in the one-dimensional CCD 1 is P1, and a displacement of the pixel from its reference position in the one-dimensional CCD 2 is P2, the following can be expressed.

$$P1 = F(\theta 1, \theta 2) \quad \text{Expression (16)}$$

$$P2 = G(\theta 1, \theta 2) \quad \text{Expression (17)}$$

Namely, θ1, θ2 can be calculated by solving the simultaneous equations of the expressions (16), (17). It should be noted that the method for calculating θ1, θ2 can be performed by using a numerical analysis such as fitting, or the like. Mathematic tracking of the light source of the present embodiment using θ1, θ2 can lead to calculation of an angle at which a light ray to be received on one-dimensional CCD 310 is incident on the sample. That is to say, the detection of the angle fluttering in the horizontal and perpendicular directions allows more accurate calculation of an angle at which a light ray to be received on one-dimensional CCD 310 is incident on the sample. This results in accurate film-thickness measurement, thereby enabling realization of an optical system resistant to the angle fluttering in the horizontal direction and the angle fluttering in the perpendicular direction.

It should be noted that, although the edge shaping means (slit plate) is arranged in the vicinity of the light-source side condenser lens, the same function can be obtained even when the above means is arranged in the vicinity of the substrate-side condenser lens. Further, although the slit plate was used as the edge shaping means for characterizing the reference light axes in the present embodiment, another edge shaping means such as an aperture plate 313' shown in FIG. 29(b) may also be employed in place of the slit plate. It is to be noted that numeral 313a' denotes an aperture.

Next, the characteristic of [5] is described. FIG. 27 shows the case where the retarder 304 is arranged in the light-projecting side optical system, and the angle fluttering occurs. Here, the following are assumed. A light ray incident on the CCD 310 at a reference angle A1 out of a light flux from a condenser lens is d L1. A light ray incident on the CCD 310 at an angle A2 is L2. A light ray reflected on the substrate on which the light ray L1 is incident at the reference angle A1 is L11. A light ray reflected on the substrate on which the light ray L2 is incident at the angle A2 is L21. At this time, the light L11 agrees with the light lay 21. Further, since the light ray L1 is in parallel with the light ray L2, the angles at which those light rays are incident on the retarder, as well as the polarized states of those light rays, become equal to one another. Accordingly, in the case of arrangement of the retarder in the light-receiving side optical system, it is possible to realize an optical system resistant to the angle fluttering. It should be noted that the applications shown in Embodiment 1 are applicable to the applications in the present embodiment.

Embodiment 4

An embodiment of an ellipsometer with a measure against the distance fluttering and the angle fluttering incorporated therein is specifically described while referring to FIGS. 30 to 33. It is to be noted that a configuration view showing the whole of a single incident angle spectroscopic ellipsometer, an electric configuration of an arithmetic processing part, and a basic operation for film-thickness measurement in the present embodiment are the same as shown in Embodiment 1.

As shown in FIG. 30, this ellipsometer has a light-projecting optical system and light-receiving optical system.

The light-projecting optical system includes: a light source (white light source in the illustrated example) 301; a collimator lens 302 for adjusting light emitted from the light source 301 into collimator light; an polarizer 303 for allowing only some polarized component in the collimator light launched from the collimator lens 302 to pass; a retarder 304 for retarding the phase of the light launched from the polarizer 303 by a quarter of light wavelength; a driving means 305 for rotating the retarder 304; and a condenser lens 306 for condensing the light after passage through the retarder to apply the light on a film-thickness measuring point of the thin film 5a of the substrate (sample) 5.

The light-receiving optical system comprises: a collimator lens (light-receiving lens) 308 for receiving reflected light of the measuring medium light applied on the substrate 5 and converting the light into collimator light; an analyzer 309 for allowing only some polarized component of the collimator light launched from the collimator lens 308 to pass; an inclined film 311 as a light-interference type spectroscopic element for gradually changing a transparent wavelength according to each position in the longitudinal direction; and a photoelectric transfer part array means (corresponding to one-dimensional CCD 310 in the illustrated example) formed by arranging a large number of photoelectric transfer parts in arrayed form in a direction perpendicular to the incident face (direction perpendicular to paper face). The inclined film 311 is in the state of being attached to the light-receiving face of the one-dimensional CCD 310 constituting the photoelectric transfer part array means, and oriented such that the longitudinal direction thereof matches the direction of a pixel line of the one-dimensional CCD 310.

A distance between the lens included in the light-receiving side optical system (corresponding to the light-receiving lens in the illustrated example) and the light-receiving face of the photoelectric transfer part array means (corresponding to the one-dimensional CCD) is set so as to almost agree with a focal angle (f) of the lens.

A series of light-receiving amount data obtained from each photoelectric transfer part of the photoelectric transfer part array means is sent to an arithmetic means (corresponding to the arithmetic processing part 3 in the illustrated example), to obtain the thickness of the thin film 5a to be measured.

The light-projecting side optical system includes a first characterization means (corresponding to a first slit 313A to function as an edge shaping means in the illustrated example) of characterizing variations in inclination of the sample in a direction rotating around a straight line as a central axis, the line being perpendicular to the incident face of the measured medium light, and further includes a second characterization means (corresponding to a second slit 313B to function as an edge shaping means in the illustrated example) of characterizing variations in inclination of the sample in a direction rotating around a straight line as a central axis, the line being an intersection between the incident face and a face to be measured.

The light-receiving side optical system includes an inclination detecting photoelectric transfer means (one-dimensional CCD 314 in the figure) of receiving the reflected light of the measuring medium light reaching from a film thickness measuring point of the sample, to detect a characteristic in the first characterization means included in the received reflected light.

The arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the first photoelectric transfer means, and also includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means. It is to be noted that details of the processing for the film-thickness measurement in the arithmetic processing part 3 are the same as described in Embodiment 1.

Main characteristics of the sensor head part of the present embodiment include: (1) adoption of a spectroscopic ellipsometer for use in the rotating retarder method; (2) adoption of an interference type spectroscopic element (inclined film) as the spectroscopic means; (3) arrangement of a photoelectric transfer part array means (corresponding to the one-dimensional CCD 1 in the illustrated example) at a rear focal distance from the light-projecting lens; (4) arrangement of a characterization means of characterizing variations in inclination of the sample in a direction rotating around a straight line as a central axis, the line being perpendicular to the incident face; (5) arrangement of a characterization means of characterizing variations in inclination of the sample in a direction rotating around a straight line as a central axis, the line being an intersection between the incident face and a face to be measured; (6) arrangement of an inclination detecting photoelectric transfer means (corresponding to the one-dimensional CCD 314 in the illustrated example) so that the focus is arranged on the light-receiving face; and (7) arrangement of a retarder in the light-projecting side optical system.

Since (1) and (2) are the same as shown in Embodiment 1, (3) is the same as shown in Embodiment 2, (4) and (5) are the same as shown in Embodiment 3, and (7) is the same as shown in Embodiments 2 and 3, the descriptions of those characteristics are left out.

Figure 31:
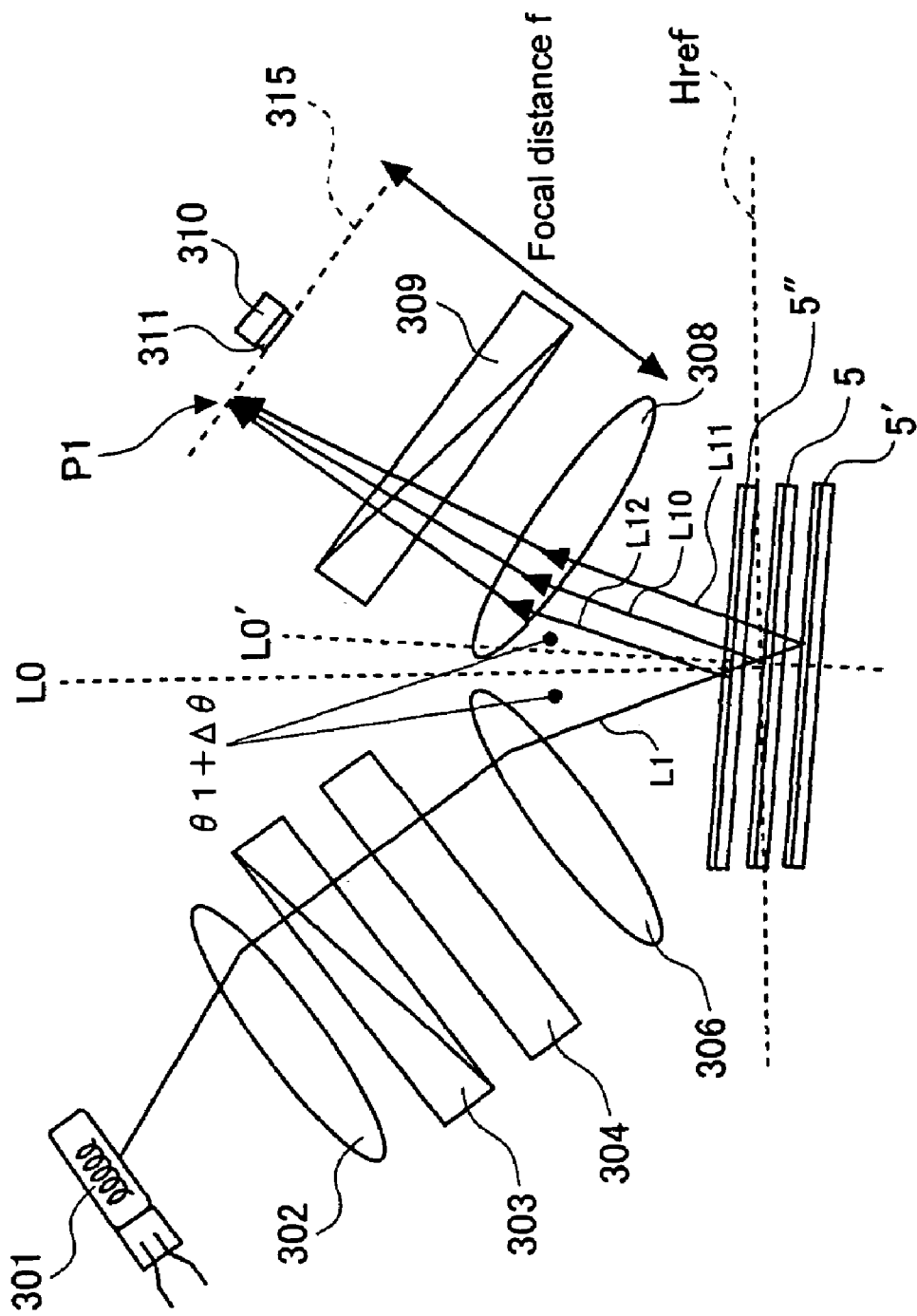
FIG. 31 shows an explanatory view showing a function of a measure against distance fluttering by incident optical path (No. 1).
Figure 32:
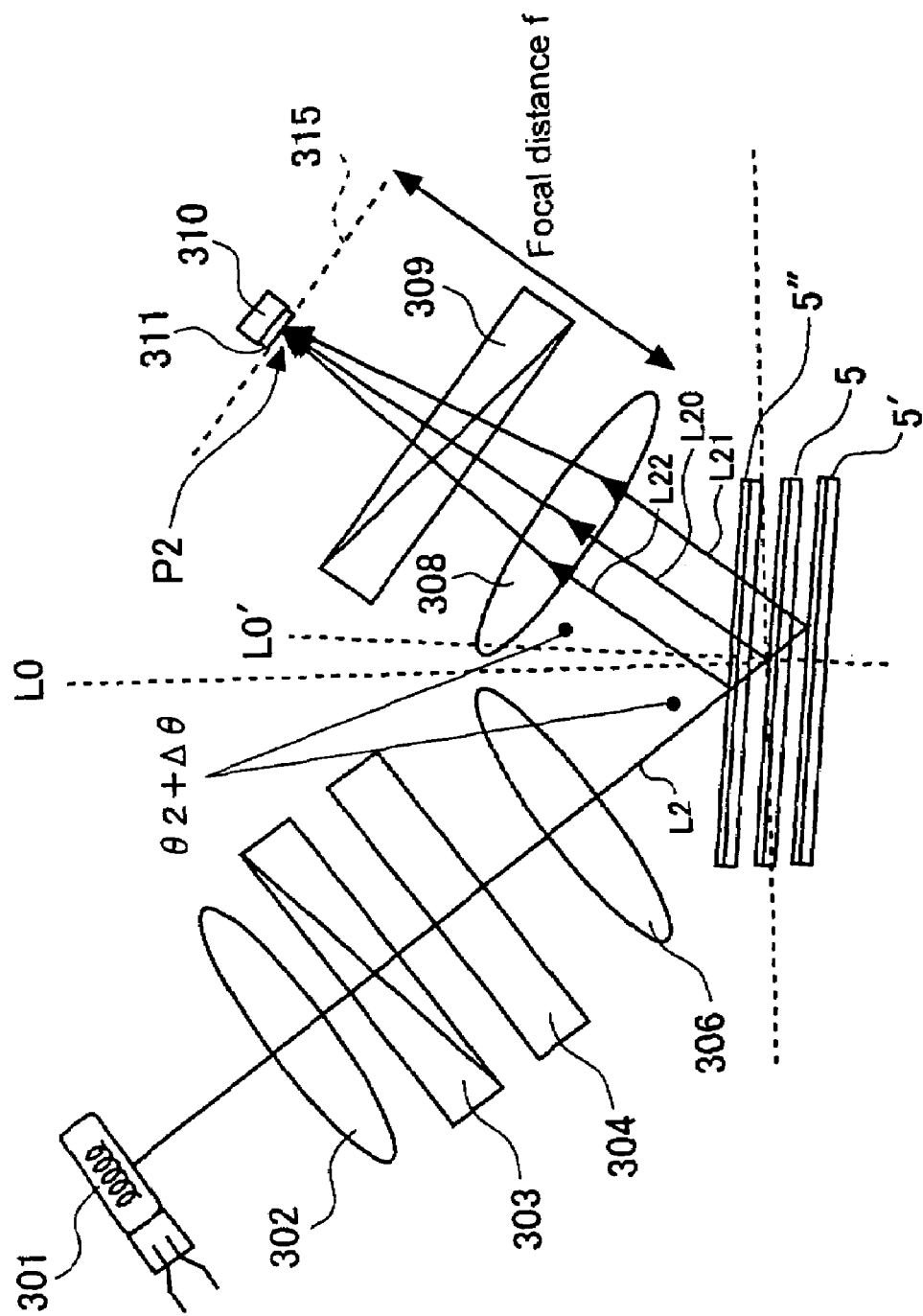
FIG. 32 shows an explanatory view showing a function of the measure against distance fluttering by incident optical path (No. 2).
Figure 33:
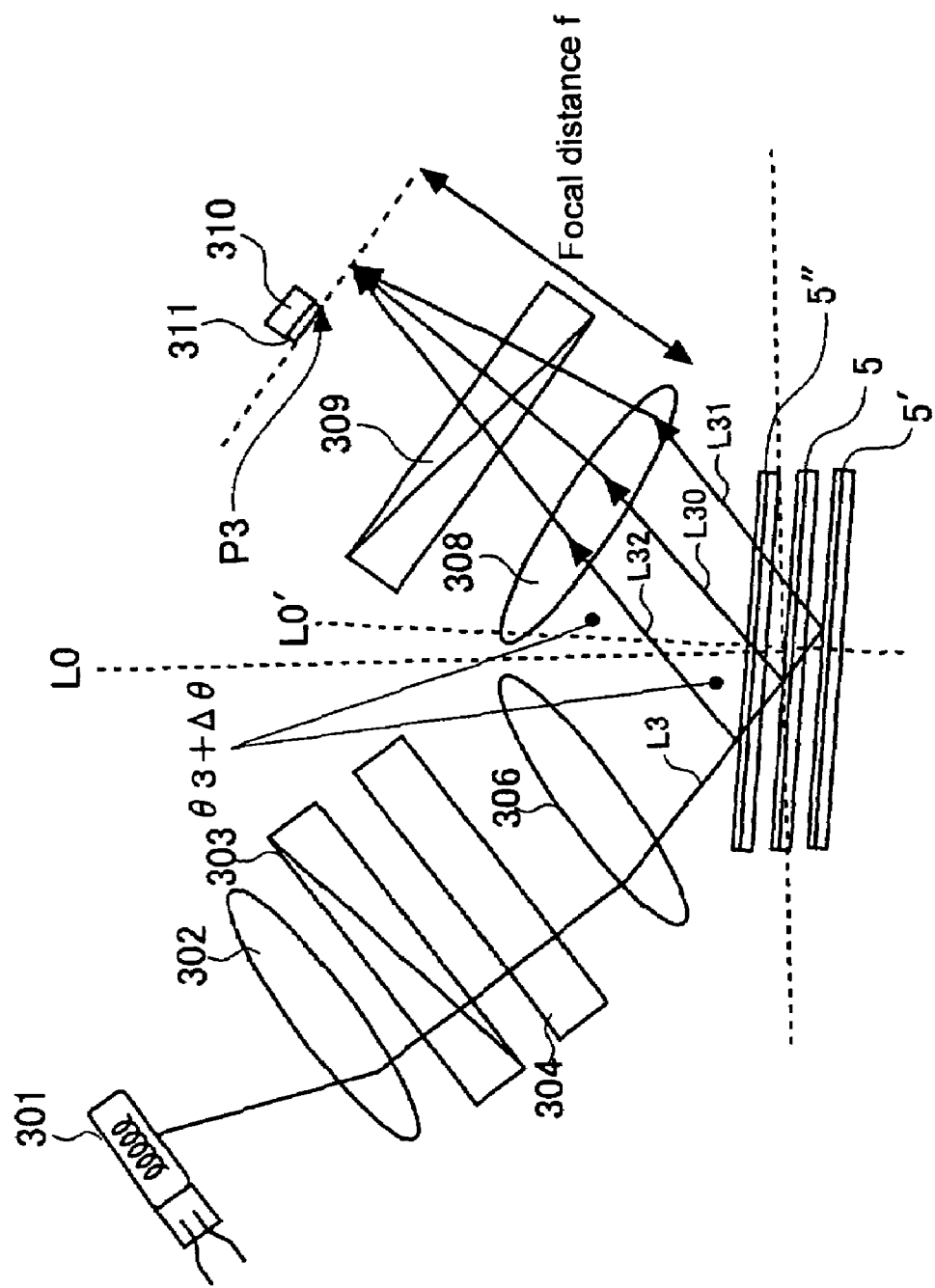
FIG. 33 shows an explanatory view showing a function of the measure against distance fluttering by incident optical path (No. 3).

In the following, before the characteristic of (6) is described, a function in the case of using the measure against the distance fluttering in combination with the measure against the angle fluttering is described. FIGS. 31 to 33 show explanatory views (No. 1 to No. 3) of a function in the case of using the measure against the distance fluttering in combination with the measure against the angle fluttering in the horizontal direction. FIGS. 31 to 33 are views where the one-dimensional CCD 314 in the present embodiment (FIG. 30) is omitted.

As above described by reference to FIGS. 19 to 22, so long as the condition is satisfied that an optical distance between the light-receiving lens 308 and the light-receiving face 315 of the one-dimensional CCD 310 almost agrees with a focal distance f of the light-receiving lens, parallel light rays to be incident on the light-receiving lens 310 converge on one point on the light-receiving face 315 of one-dimensional CCD 310.

Here, as apparent by reference to FIGS. 31 to 33, so long as the horizontally displaced angle $\Delta\theta$ is constant, each of reflected light in three groups (L10, L11, L12), (L20, L21, L22), (L30, L31, L32) from the substrates 5", 5, 5' arranged at the respective heights (raised height, reference height, lowered height) are kept in parallel relation with one another in each of the groups, regardless of the presence or absence of the distance fluttering.

Also in this embodiment, therefore, the reflected light (L10, L11, L12), (L20, L21, L22), (L30, L31, L32) with respect to the incident light L1, L2, L3 certainly converge on the three points P1, P2, P3 on the light-receiving plane of one-dimensional CCD 310, thereby allowing realization of an optical system unaffected by the distance fluttering.

Similarly, also as the measure against the angle fluttering in the perpendicular direction, so long as the condition is satisfied that a distance between the light-receiving lens 308 and the light-receiving face 315 of the one-dimensional CCD 310 almost agrees with the focal distance f of the light-receiving lens 308, parallel light rays to be incident on the light-receiving lens 310 converge on one point on the light-receiving face 315 of one-dimensional CCD 310.

In the following, the characteristic of (6) is described. What was described above can also be applied to the one-dimensional CCD 314 in the present embodiment (FIG. 30). Namely, so long as the condition is satisfied that an optical distance between the light-receiving lens 308 and the light-receiving face 315 of the one-dimensional CCD 310 almost agrees with the focal distance f of the light-receiving lens, parallel light rays to be incident on the light-receiving lens 310 converge on one point on the light-receiving face 315 of one-dimensional CCD 310. Consequently, it is possible to realize an optical system not affected by the distance fluttering.

It is to be note that the method for calculating an incident angle in the case where the angle fluttering in the horizontal direction and the angle fluttering in the perpendicular direction have occurred is the same as shown in Embodiment 3.

Therefore, according to the present embodiment, it is possible to measure a thickness/quality of a single-layered film or a multi-layered film as a sample regardless of the distance fluttering and the angle fluttering of the sample. Particularly, according to the present embodiment, correction concerning the distance fluttering has already been completed and a change in an observed waveform has been corrected at the time of observation with the one-dimensional CCD 310. Hence the change in the observed waveform is caused only by the angle fluttering, and thereby the arithmetic processing part may only perform a process for correcting an error component attributed to the angle fluttering (process for calculating an accurate incident angle).

As thus described, since the distance fluttering and the angle fluttering are corrected in mutually independent processes, there occurs no disadvantage in which two correction processes conflict with one another to prevent convergence of the arithmetic processing as in the case where changes in observed waveforms caused by the two kinds of fluttering are corrected by the arithmetic processing part in the one and the same process. Further, another characteristic is that, even with a spot diameter increased, the theories of the distance fluttering and the angle fluttering of the sample are held, and it is thereby possible to realize an optical system resistant to the distance fluttering and the angle fluttering.

Consequently, according to the present embodiment, setting conditions (distance/angle fluttering) are eased so that a conventionally required auto-focus function, or adjustment of a focus and inclination of a stage prior to measurement, becomes unnecessary. At the same time, size reduction of the instrument is realized, thereby enabling provision of an instrument suitable for the in-line measurement. It is to be noted that the applications shown in Embodiment 1 are applicable to the applications in the present embodiment.

Embodiment 5

Figure 34:
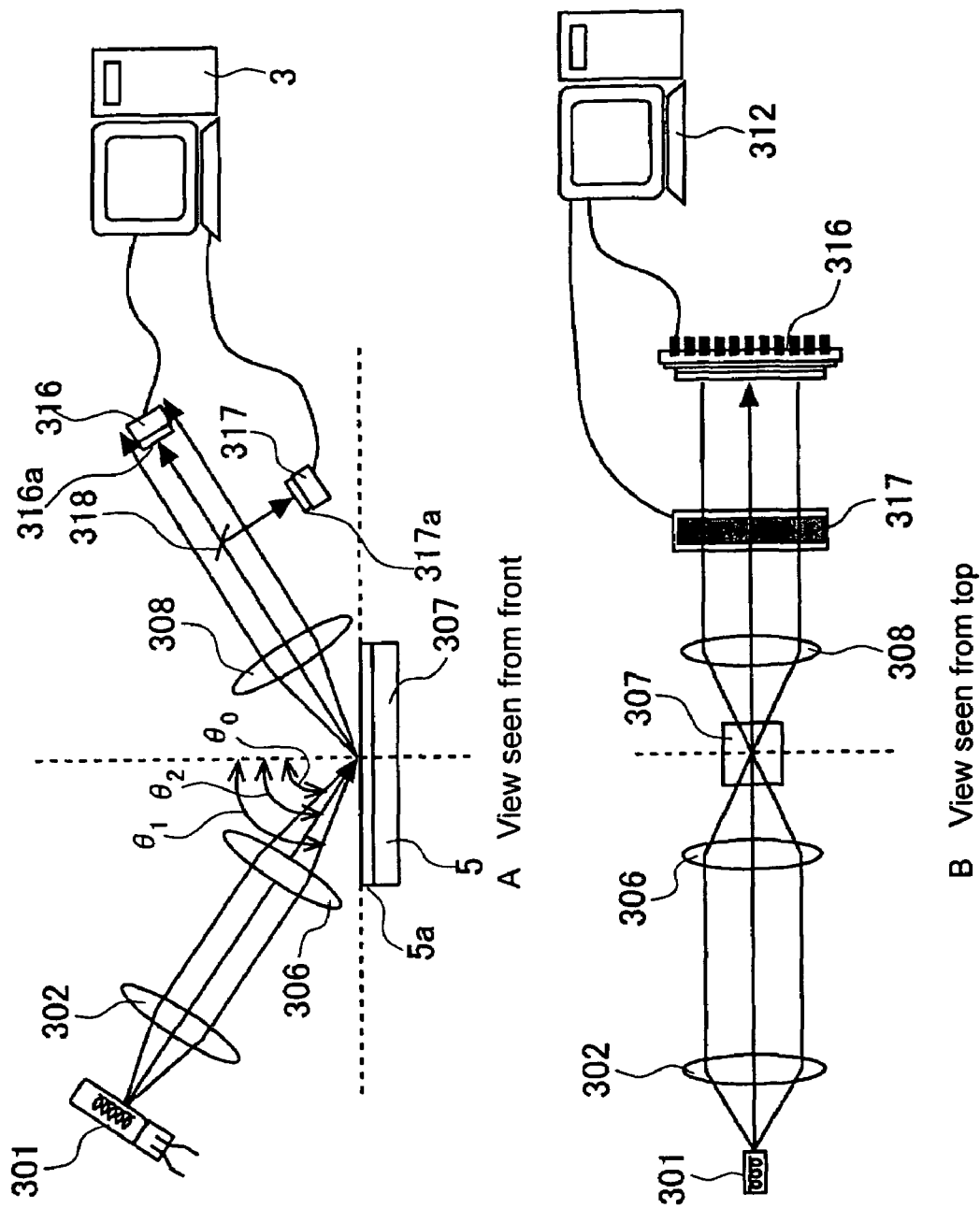
FIG. 34 shows a view showing another example of the optical system of the sensor head part.
Figure 36:
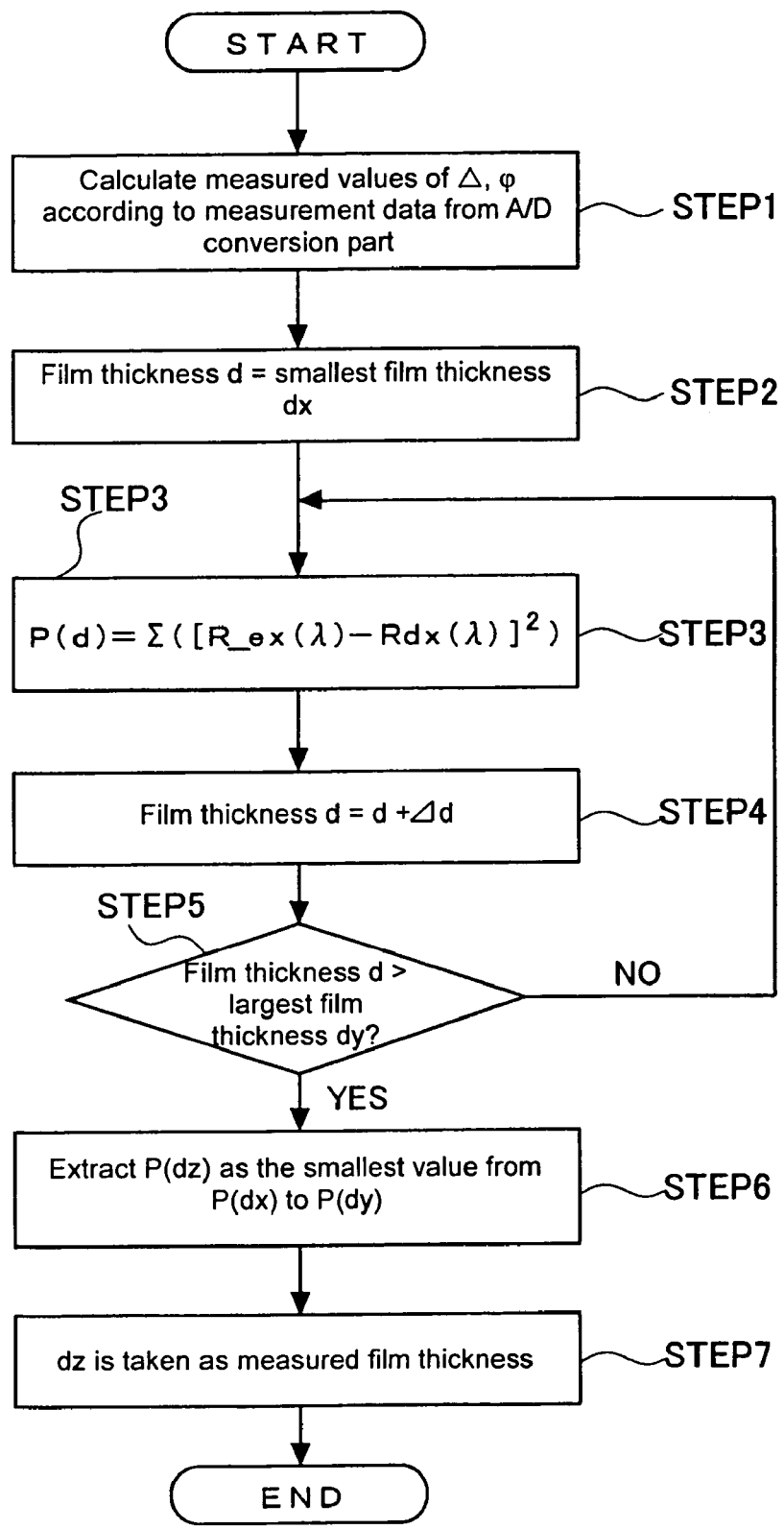
FIG. 36 shows a flowchart showing details of a film thickness measurement program.

Next, an embodiment of an ellipsometer with a size reduction technique incorporated therein, for separating light into S polarized light and P polarized light and detecting those light to measure a film thickness or film quality based upon a reflectance ratio, is specifically described while referring to FIGS. 34 to 36. It is to be noted that an overall configuration view of the present embodiment and an electric configuration view of an arithmetic processing part in the present embodiment are the same as shown in Embodiment 1.

FIG. 34 shows an optical configuration of a sensor head part with the size reduction technique incorporated therein. It is to be noted that component parts in the optical system configuration of FIG. 34, which are identical to shown in the above embodiments, are provided with the same numerals as those of the above embodiments, and descriptions thereof are omitted.

Main characteristics of the sensor head part of the present embodiment include adoption of an interference type spectroscopic element (inclined film) as the spectroscopic means. A basic operation for the film-thickness measurement is described while referring to FIG. 34.

The measuring medium light emitted from the light source 301 converges and is applied on the thin film 5a on the substrate 5 to be measured by the function of the condenser lens 306 through the collimator lens 302. A film-thickness measuring point of the sample is set to almost the position on which the incident light converges. At this time, the measuring medium light having sequential incident angle components in the range of $\theta 0$ to $\theta 1$ are to be incident.

The measuring medium light incident through the condenser lens is reflected on the sample. Light incident at an angle of $\theta 2$, out of the reflected light of the measuring medium light reaching from the film-thickness measurement point of the sample, is guided by the function of the light-receiving lens 308 through the collimator lens 308, a beam splitter 318, and inclined films 316a, 317a, and an S polarized component is guided to the light-receiving face of a one-dimensional CCD 316 while a P polarized component is guided to the light-receiving face of the one-dimensional CCD 317.

Accordingly, an output signal s2 is sent from each of the one-dimensional CCD 316 and the one-dimensional CCD 317, which corresponds to serially arranged data on light-receiving amount of each light-receiving element (pixel). Based upon this output signal s2 from the one-dimensional CCD, a reflected light intensity distribution according to the waveform at the incident angle ($\theta 2$) is observed.

The reflected light intensity distribution observed at this time is an amount according to the wavelength. A ratio of the reflectance of the S polarized light to the reflectance of the P polarized light (measured value $R_s/R_p$) is then calculated. Simultaneously, a ratio (theoretical value) of the reflectance of the S polarized light to the reflectance of the P polarized light (theoretical value $R_s/R_p$) is calculated. Lastly, the measured value and the theoretical value are put in contrast with one another to obtain a film thickness. The measured value $R_s/R_p$ is calculated by obtaining a ratio of the intensity distribution waveform of the one-dimensional CCD 1 to the intensity distribution waveform of the one-dimensional CCD 2. The theoretical values of $R_s$ and $R_p$ are calculated in the same manner as shown in Embodiment 1.

Eventually, the following expression:

$$S/P \text{ polarized light absolute reflectance ratio } R = |R_p|/|R_s| \quad \text{Expression (18)}$$

where the absolute reflectance ratio R is a theoretical value is calculated with respect to each waveform, to obtain a wavelength dependence spectrum.

Then, using a film thickness value d of the oxide film 701 as a parameter, the measured spectrum is compared with a theoretical spectrum (table data) (cf. FIG. 35) which is obtained after a later-described half value width correcting process for the inclined film, so that the film thickness value d can be calculated.

As a film-thickness arithmetic processing method in the CPU 31 of the arithmetic processing part 3, a curve fitting method can be used. As described above, the curve fitting method comprises the steps of: comparing waveform data (table data) on theoretical values of a S/P polarized light absolute reflectance ratio R after performance of a later-described inclined film half value width correcting process with respect to each film thickness, which was previously calculated and stored as a table, and waveform data on S/P polarized light absolute reflectance ratio R, which was calculated from measured data on a light-receiving amount; extracting data having a smallest error by the least-squares method; and obtaining a film thickness of the waveform data as a thickness of a thin film to be measured. Another usable film-thickness arithmetic processing method may be a method such as an extreme value searching method or a film-thickness calculating method for weighting the S/P polarized light absolute reflectance ratio R.

When a reflective index n of a thin film to be measured, $r_0$ and $r_1$ are previously inputted from the input/output part such as the keyboard, the arithmetic part performs an arithmetic operation on values of the phase difference $\Delta$ and the amplitude ratio $\psi$ with respect to each value of the film thickness d and the wavelength $\lambda$, at the incident angle $\theta$, and the obtained value is held as a table in a memory in the arithmetic part. FIG. 35 shows examples of such a table.

The curve fitting is executed according to a flowchart of FIG. 36. Namely, first, the CPU 31 acquires measurement data digitalized by the A/D conversion part 33, to calculate measured values of a phase difference $\Delta ex\,(\lambda)$ and an amplitude ratio $\psi ex\,(\lambda)$ (STEP 1). Next, the film thickness d is made the smallest film thickness dx (STEP 2), and using the theoretical table of FIG. 35, a square of a difference between theoretical values (film thickness d=dx) of the phase difference $\Delta dx\,(\lambda)$ and the amplitude ratio $\psi dx\,(\lambda)$ and measured values of the phase difference $\Delta ex\,(\lambda)$ and the amplitude ratio $\psi ex\,(\lambda)$, $[\Delta ex\,(\lambda) - \Delta dx\,(\lambda)]^2 + [\psi ex\,(\lambda) - \psi dx\,(\lambda)]^2$, is calculated in the wavelength range of $\lambda_p$ to $\lambda_q$ in units of $\Delta\lambda$. A sum of the squares is obtained using the following valuation expression (STEP 3):

$$\text{Valuation expression } P(d) = \Sigma([\Delta ex\,(\lambda) - \Delta dx\,(\lambda)]^2 + [\psi ex\,(\lambda) - \psi dx\,(\lambda)]^2),$$

and then stored into the memory. It is to be noted that the valuation expression P(d) in the fitting may be different from the one shown above so long as expressing differences between theoretical values and measured values.

As thus described, values of the film thickness d are sequentially increased by $\Delta d$ until reaching the largest film thickness dy (STEP 5). At that time, a sum of squares of difference in film thickness between theoretical data and measured data is obtained (STEP 3), and then stored into the memory.

Upon completion of the above-mentioned calculation of the sum of squares performed until the film thickness reaches the largest film thickness dy (in the case of YES in STEP 5), a sum of squares P(dz), taking the smallest value, out of the sums of squares P(dx) to P(dy) in the film thickness range of dx to dy having been stored into the memory is extracted (STEP 6), and the film thickness dz at that time is taken as a measurement film thickness (STEP 7)

Embodiment 6

Figure 37:
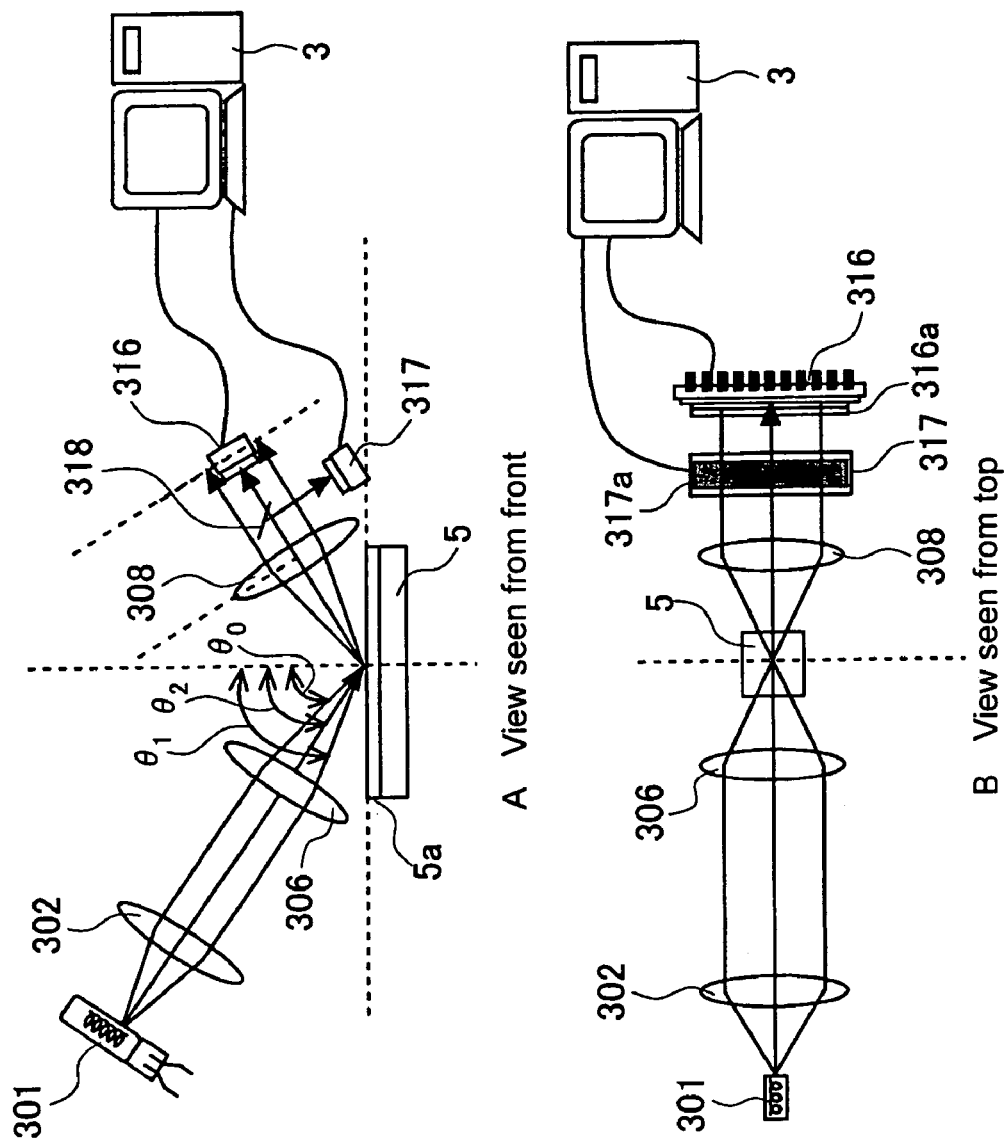
FIG. 37 shows a view showing another example of the optical system of the sensor head part.

Next, an embodiment of an ellipsometer with a size reduction technique incorporated therein, being resistant to the distance fluttering, is specifically described, while referring to FIG. 37. This ellipsometer separates light into S polarized light and P polarized light, and detects those light to measure a film thickness or film quality based upon a reflectance ratio. It is to be noted that an overall configuration view of the present embodiment and an electric configuration view of an arithmetic processing part in the present embodiment are the same as shown in Embodiment 1, and a basic operation for film-thickness measurement in the present embodiment is the same as shown in Embodiment 5.

FIG. 37 shows an optical configuration of a sensor head part with the measure against the distance fluttering incorporated therein. It is to be noted that component parts in FIG. 37, which are identical to shown in the above embodiments, are provided with the same numerals as those of the above embodiments, and descriptions thereof are omitted.

Main characteristics of the sensor head part of the present embodiment include: (1) adoption of an interference type spectroscopic element (inclined film) as the spectroscopic means; (2) arrangement of a one-dimensional CCD 1 and one-dimensional CCD 2 on an optical path at a rear focal distance from the light-projecting lens; and (3) arrangement of a retarder in the light-projecting side optical system. Each of these characteristics (1) to (3) is the same as described in Embodiments 1 and 2.

Embodiment 7

Figure 38:
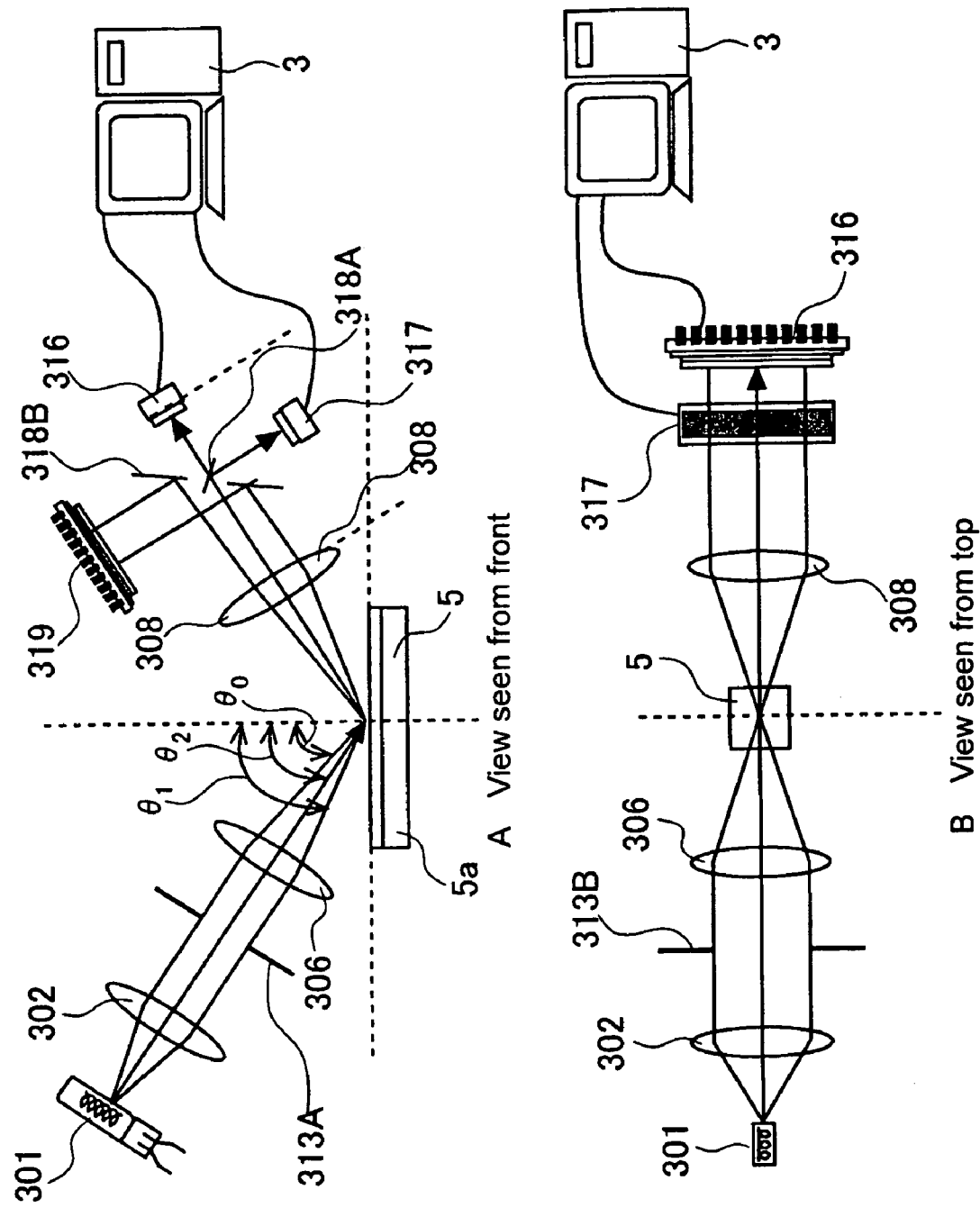
FIG. 38 shows a view showing another example of the optical system of the sensor head part.

Next, an embodiment of an ellipsometer with a size reduction technique incorporated therein, being resistant to the angle fluttering, is specifically described, while referring to FIG. 38. This ellipsometer separates light into S polarized light and P polarized light, and detects those light to measure a film thickness or film quality based upon a reflectance ratio. It is to be noted that an overall configuration view of the present embodiment and an electric configuration view of an arithmetic processing part in the present embodiment are the same as shown in Embodiment 1.

FIG. 38 shows an optical configuration of a sensor head part with the measure against the angle fluttering incorporated therein. It is to be noted that component parts in FIG. 38, which are identical to shown in the above embodiments, are provided with the same numerals as those of the above embodiments, and descriptions thereof are omitted.

This spectroscopic ellipsometer comprises a light-projecting side optical system, a light-receiving side optical system, and an arithmetic means (corresponding to the arithmetic processing part 3 in the illustrated example) of obtaining a film thickness to be measured based upon a series of data on light-receiving amount which is obtained from each of the photoelectric transfer parts of the photoelectric transfer part array means. The light-projecting side optical system includes: a collimator lens 302 for adjusting measuring medium light into collimator light to be incident on a film-thickness measuring point of the sample; and a condenser lens 306 for condensing light from a light source (white light source in the illustrated example) 301 and projecting the light on a film-thickness measuring point of the thin film 5a of the substrate (sample) 5. The light-receiving side optical system includes: a collimator lens (light-receiving lens) 308 for adjusting reflected light of the medium light into collimator light; a polarized beam splitter 318 for separating the light into S polarized light and P polarized light; a first photoelectric transfer part array means (corresponding to a one-dimensional CCD 316 in the illustrated example) of detecting the S polarized light, formed by arranging an inclined film and a large number of photoelectric transfer parts in arrayed form in a direction perpendicular to an incident face; and an inclination detecting photoelectric transfer part array means (corresponding to a one-dimensional CCD 317 in the illustrated example) of detecting the P polarized light.

Further, the light-projecting side optical system includes a first characterization means (corresponding to a slit 313A to function as an edge shaping means in the illustrated example) of characterizing variations in inclination of the sample in a direction rotating around a straight line as a central axis, the line being perpendicular to the incident face of the measured medium light, and further includes a second characterization means (corresponding to a slit 313B to function as the edge shaping means in the illustrated example) of characterizing variations in inclination of the sample in a direction rotating around a straight line as a central axis, the line being an intersection between the incident face and a face to be measured.

The light-receiving side optical system includes an inclination detecting photoelectric transfer means (corresponding to a one-dimensional CCD 319 in the illustrated example) of receiving the reflected light of the measuring medium light reaching from a film thickness measuring point of the sample, to detect a characteristic in the first characterization means included in the received reflected light.

The arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the first photoelectric transfer means, and further includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means. It is to be noted that details of the processing for the film-thickness measurement in the arithmetic processing part 3 are the same as described in Embodiment 1.

Main characteristics of the sensor head part of the present embodiment include: (1) adoption of an interference type spectroscopic element (inclined film) as the spectroscopic means; (2) arrangement of a characterization means of characterizing variations in inclination of the sample in a direction rotating around a straight line as a central axis, the line being perpendicular to the incident face; (3) arrangement of a characterization means of characterizing variations in inclination of the sample in a direction rotating around a straight line as a central axis, the line being an intersection between the incident face and a face to be measured; and (4) arrangement of a retarder in the light-projecting side optical system.

Since (1) is the same as shown in Embodiment 1, (2) and (3) are the same as shown in Embodiment 4, and (4) is the same as shown in Embodiment 3, the descriptions of these characteristics are left out. It is to be noted that the applications shown in Embodiment 1 are applicable to the applications of the present embodiment.

Embodiment 8

Next, an embodiment of an ellipsometer with a size reduction technique incorporated therein, being resistant to the distance fluttering and the angle fluttering, is specifically described. This ellipsometer separates light into S polarized light and P polarized light, and detects those light to measure a film thickness or film quality based upon a reflectance ratio. It is to be noted that an overall configuration view of the present embodiment and an electric configuration view of an arithmetic processing part in the present embodiment are the same as shown in Embodiment 1.

Figure 39:
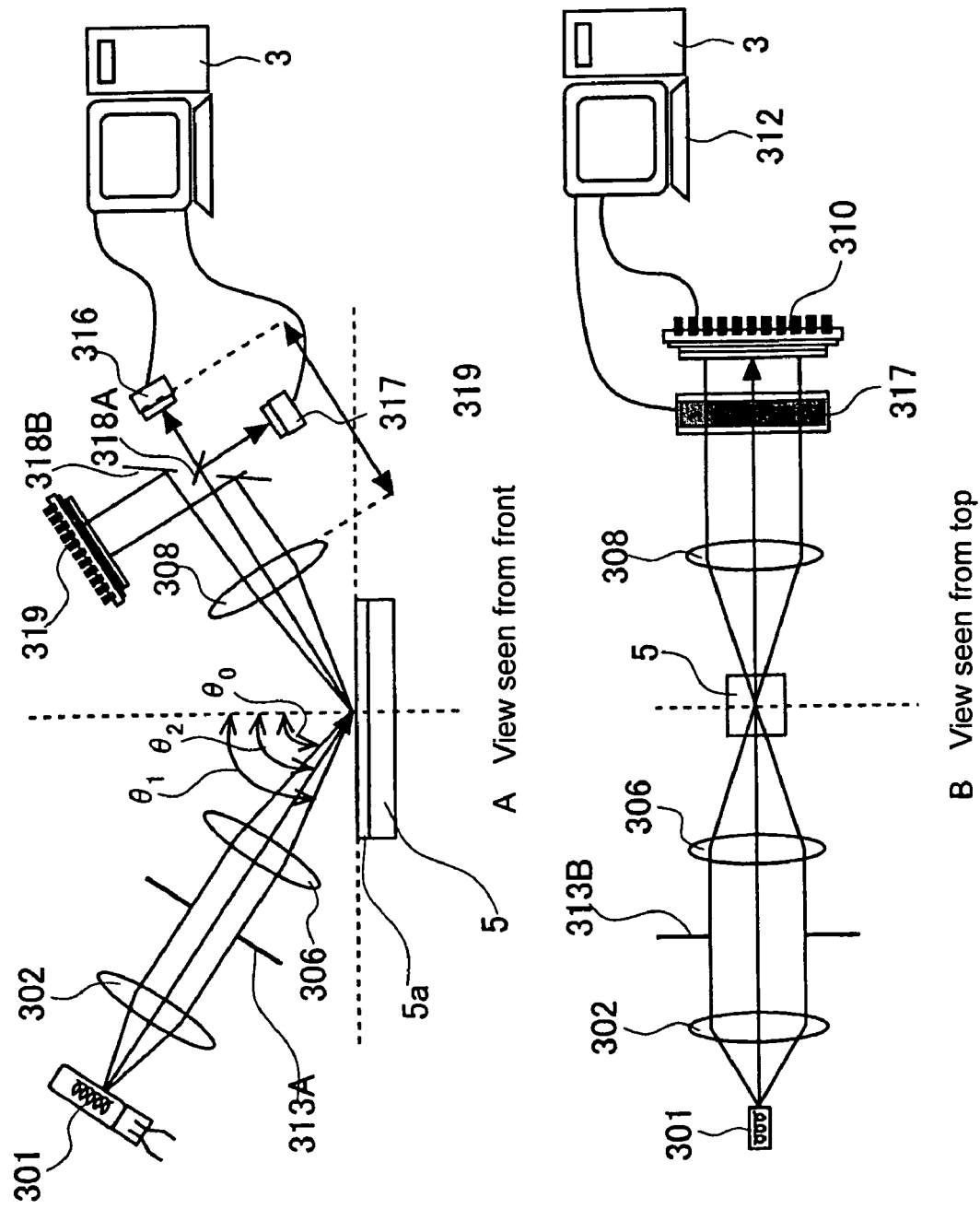
FIG. 39 shows a view showing another example of the optical system of the sensor head part.

FIG. 39 shows an optical configuration of a sensor head part with the measures against the distance fluttering and the angle fluttering incorporated therein. This spectroscopic ellipsometer comprises a light-projecting side optical system, a light-receiving side optical system, and an arithmetic means (corresponding to the arithmetic processing part 3 in the illustrated example) of obtaining a film thickness to be measured based upon a series of data on light-receiving amount which is obtained from each of the photoelectric transfer parts of the photoelectric transfer part array means. The light-projecting side optical system includes: a collimator lens 302 for adjusting measuring medium light into collimator light to be incident on a film-thickness measuring point of the sample; and a condenser lens 306 for condensing light from a light source (white light source in the illustrated example) 301 and projecting the light on a film-thickness measuring point of the thin film 5a of the substrate (sample) 5. The light-receiving side optical system includes: a collimator lens (light-receiving lens) 308 for adjusting reflected light of the medium light into collimator light; a polarized beam splitter 318A for separating the light into S polarized light and P polarized light; a first photoelectric transfer part array means (corresponding to a one-dimensional CCD 316 in the illustrated example) of detecting the S polarized light, formed by arranging an inclined film and a large number of photoelectric transfer parts in arrayed form in a direction perpendicular to an incident face; and an inclination detecting photoelectric transfer part array means (corresponding to a one-dimensional CCD 317 in the illustrated example) of detecting the P polarized light.

Further, the light-projecting side optical system includes a first characterization means (corresponding to a slit 313A to function as an edge shaping means in the illustrated example) of characterizing variations in inclination of the sample in a direction rotating around a straight line as a central axis, the line being perpendicular to the incident face of the measured medium light, and further includes a second characterization means (corresponding to a slit 313B to function as the edge shaping means in the illustrated example) of characterizing variations in inclination of the sample in a direction rotating around a straight line as a central axis, the line being an intersection between the incident face and a face to be measured.

The light-receiving side optical system includes an inclination detecting photoelectric transfer means (corresponding to a one-dimensional CCD 319 in the illustrated example) of receiving the reflected light of the measuring medium light reaching from a film thickness measuring point of the sample, to detect a characteristic in the first characterization means included in the received reflected light.

The arithmetic means includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the first photoelectric transfer means, and further includes a light-receiving amount data correcting means of correcting an error component generated due to variations in inclination of the sample included in a series of light-receiving amount data obtained from each of the photoelectric transfer parts, based upon the characteristic of the variations in inclination of the sample detected by the inclination detecting photoelectric transfer means.

Additionally, a distance on the optical path between the lens (corresponding to the light-receiving lens 308 in the illustrated example) included in the light-receiving side optical system and the light-receiving face of the first/inclination detecting photoelectric transfer part array means (corresponding to the one-dimensional CCD 316, the one-dimensional CCD 317) is set so as to almost agree with a focal distance (f) of the lens. It is to be noted that details of the processing for the film-thickness measurement in the arithmetic processing part 3 are the same as described in Embodiment 1.

Embodiment 9

Figure 40:
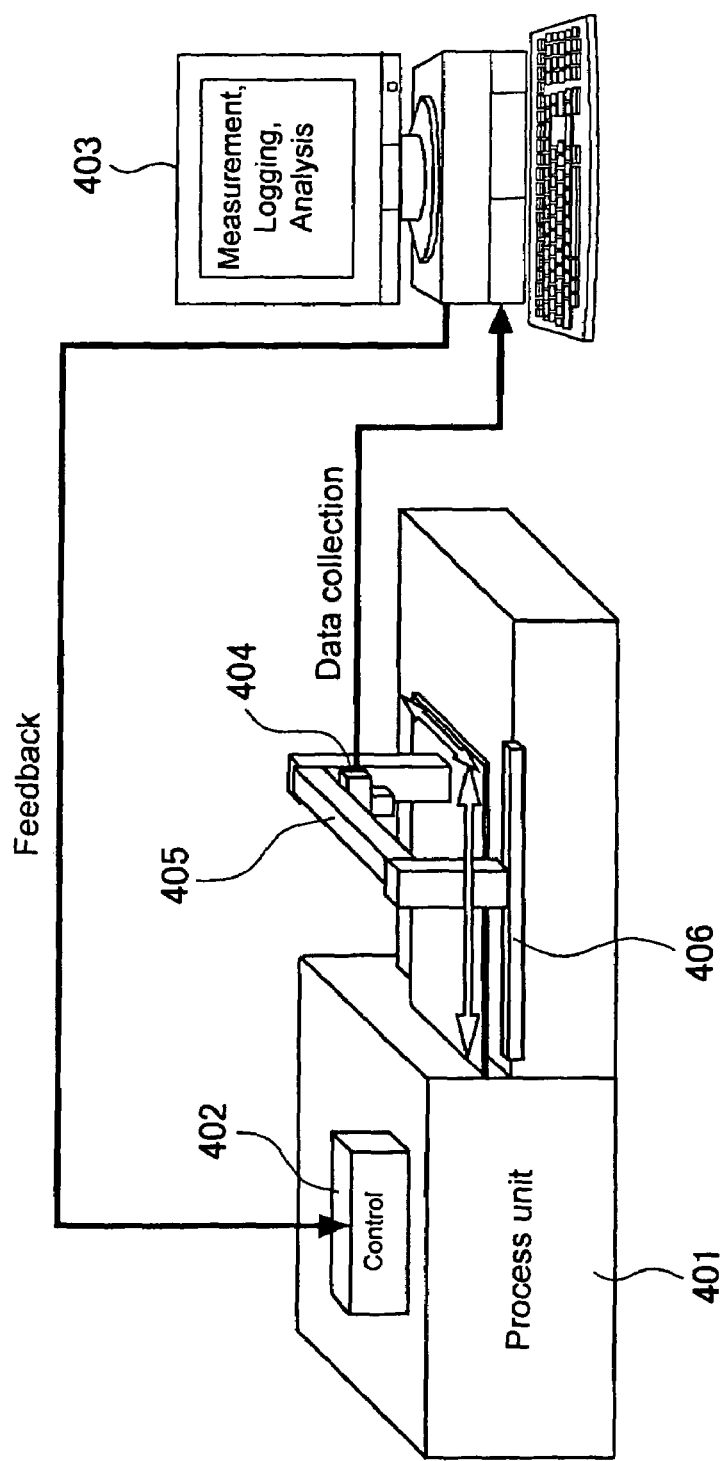
FIG. 40 shows a view showing an example of applying the instrument of the present invention to an inline measurement.
Figure 42:
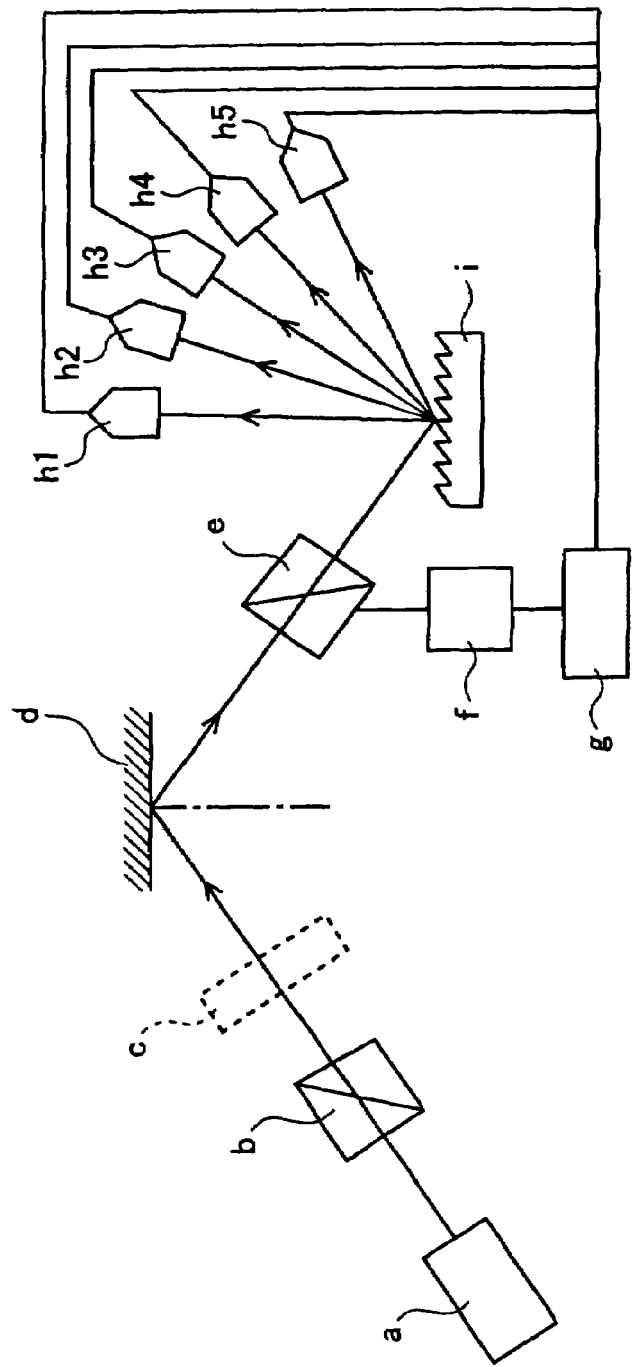
FIG. 42 shows a configuration view showing one example of a conventional single incident angle spectroscopic ellipsometer for rotating an analyzer.
Figure 43:
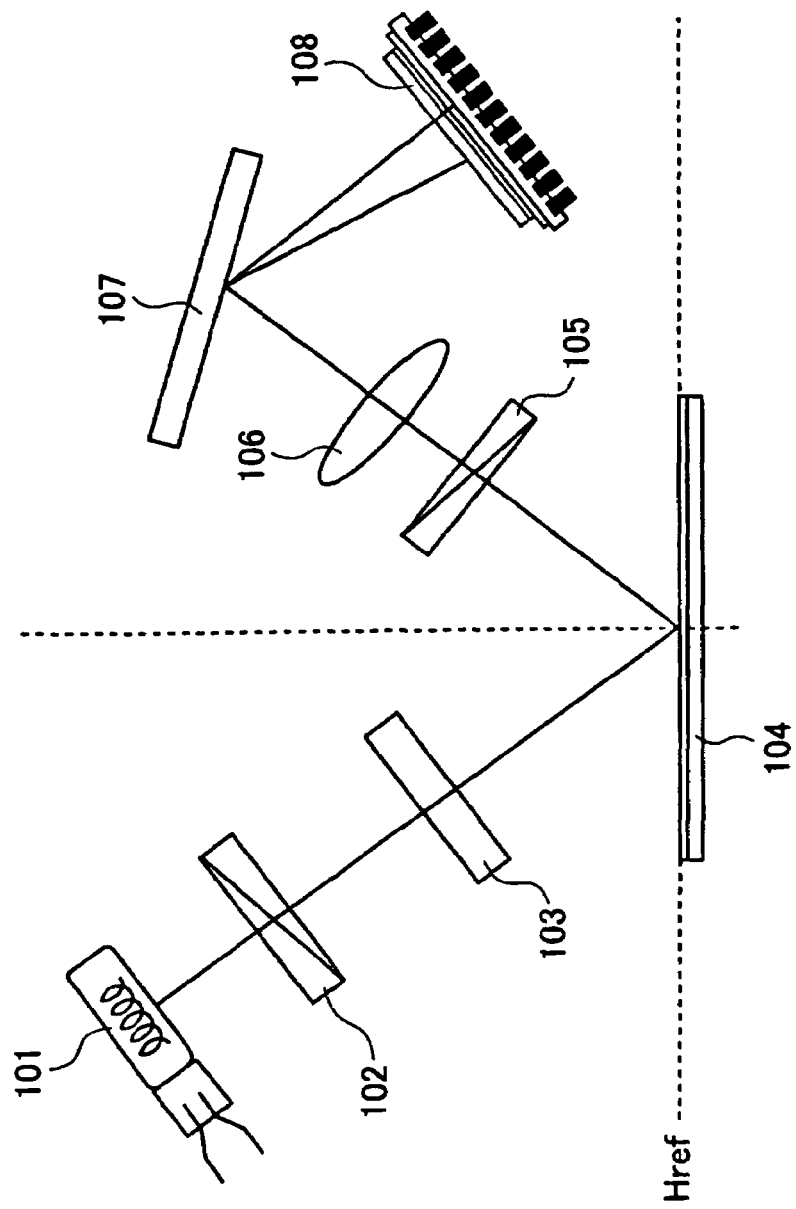
FIG. 43 shows a view showing a simplified configuration of the single incident angle spectroscopic ellipsometer shown in FIG. 42.

Next, an application of any one of Embodiments 1 to 8 is described while referring to FIG. 40. FIG. 40 shows an example of application into a manufacturing line for a product involving a film formation process, such as a semiconductor product or an FPD. In the figure, numeral 401 denotes a process unit, numeral 402 denotes a controller, numeral 403 denotes a computer such as a personal computer, numeral 404 denotes a measuring device, numeral 405 denotes a shifting guide in a width direction, and numeral 406 is a guide for shift in the line direction. According to this application, first, a sensor (instrument of the present invention) is arranged on a product flowing in the manufacturing line, data on every product is collected in-line, and the collected data is transferred to the computer 403 such as a personal computer. Subsequently, the transferred data is logged and analyzed in the computer 403. Finally, the analysis result is fed back to the controller 402 of the process unit 401, thereby enabling improvement in manufacturing process as well as product yield.

According to the spectrometric measuring instrument of the present invention, it is possible to realize size reduction of the instrument and also obtain resistance to the distance fluttering, the angle fluttering in the horizontal direction, and the angle fluttering in the perpendicular direction, whereby a spectrometric measuring instrument can be realized which is suitable for in-line measurement for example in a semiconductor manufacturing process, an FPD manufacturing process, or the like.

What is claimed is:

1. A spectrometric measuring instrument, which is a measuring instrument for irradiating a sample with measuring medium light to receive a reflected light and detecting a change in polarized state of the reflected light from the irradiated light, to obtain a film thickness or film quality of the sample, wherein the instrument comprises:

a light-projecting side optical system for applying and condensing the measuring medium light onto a sample surface;

a light-receiving side optical system, which includes a photoelectric transfer part array device comprising an array of photoelectric transfer parts arrayed in a direction perpendicular to a plane defined by the incoming light to an incident face and the reflected light from the incident face, and a light interference type spectral element for changing a transmission wavelength at which light is transmitted by means of a lens according to the position of the spectral element at which light is incident on, and in which the spectral element is provided immediately before the photoelectric transfer part array device and a distance between the lens and the light-receiving face of the photoelectric transfer part array device is set so as to substantially agree with a focal distance of the lens so that the light is received from the sample through the lens by the photoelectric transfer part array device; and an arithmetic device for calculating an amount of change in state of polarization of the reflected light from the irradiated light corresponding to the transmission wavelength of the spectral element based upon a received light intensity data which is obtained from each of the photoelectric transfer parts of the photoelectric transfer part array device and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness or a film quality, and further, the light-projecting side optical system includes a characterization device for characterizing variations in inclination of the sample around a straight line as a central axis, the line being perpendicular to the incident face of the measured medium light, the light-receiving side optical system includes an inclination detecting photoelectric transfer device that receives the reflected light of the measuring medium light from a film-thickness measuring point of the sample, to detect a characteristic of variations in inclination of the sample included in the received reflected light, and the arithmetic device includes a received light intensity data correcting device that corrects an error component generated due to variations in inclination of the sample included in the received light intensity data obtained from each of the photoelectric transfer parts, based upon the characteristic of the variations in inclination of the sample detected by the inclination detecting photoelectric transfer device.

2. The spectrometric measuring instrument according to claim 1, wherein the characterization device is a beam shaping device that edge shapes a beam, corresponding to an inclination reference of the sample, in a section contour of the measuring medium light.

3. The spectrometric measuring instrument according to claim 1, wherein a light source of the measuring medium light is a white LED light source.

4. The spectrometric measuring instrument according to claim 1, wherein a diameter of a spot on the sample is not larger than 1 mm.

5. The spectrometric measuring instrument according to claim 1, wherein a two-dimensional array device is used as the photoelectric transfer part array device.

6. The spectrometric measuring instrument according to claim 1, wherein the arithmetic part for calculating the theoretical waveform includes a process for correcting an error due to wavelength resolution of the spectrometric element.

7. The spectrometric measuring instrument according to claim 1, wherein the arithmetic part includes a process for calculating a theoretical waveform according to a theoretical formula of reflectance of light including light reflected from the rear face of a sample substrate in the case where the sample substrate is a transparent substrate.

8. The spectrometric measuring instrument according to claim 7, wherein the arithmetic part has an input device capable of inputting whether the sample substrate is a transparent substrate or an opaque substrate.

9. The spectrometric measuring instrument according to claim 1, wherein the light-projecting side optical system comprises a retarder having the function of retarding a phase.

10. The spectrometric measuring instrument according to claim 9, wherein the instrument comprises a mechanism for rotating the retarder having the function of retarding a phase, the light-projecting side optical system includes a polarizer, and the light-receiving side optical system includes an analyzer.

11. The spectrometric measuring instrument according to claim 1, wherein the measuring medium light irradiated from the light-projecting side optical system includes two or more polarized components, and the light-receiving side optical system includes: two or more photoelectric transfer part array device corresponding to the respective polarized components; and a polarization splitting device of splitting reflected light, reaching from a film-thickness measuring point on the sample, into polarized components to guide the respective split polarized components to appropriate photoelectric transfer part array device.

12. The spectrometric measuring instrument according to claim 1, wherein the chromaticity of the sample is measured.

13. The spectrometric measuring instrument according to claim 1, wherein the film thickness of the sample is measured.

14. The spectrometric measuring instrument according to claim 13, wherein the instrument is disposed in a manufacturing line and performs an in-line measurement.

15. The spectrometric measuring instrument according to claim 14, wherein the instrument is disposed in the manufacturing line and performs a one-hundred-percent, testing, and then a logged and analyzed result can be fed back to the instrument in the manufacturing line.

16. The spectrometric measuring instrument according to claim 1, wherein the film quality of the sample is measured.

17. The spectrometric measuring instrument according to claim 16, wherein the instrument is disposed in a manufacturing line and performs an in-line measurement.

18. A spectrometric measuring instrument, which is a measuring instrument for irradiating a sample with measuring medium light to receive a reflected light and detecting a change in state of polarization of the reflected light from the irradiated light, to obtain a film thickness or film quality of the sample, wherein the instrument comprises:

a light-projecting side optical system for applying and condensing the measuring medium light onto a sample surface;

a light-receiving side optical system, which includes a photoelectric transfer part array device comprising an array of photoelectric transfer parts arrayed in a direction perpendicular to a plane defined by the incoming light to an incident face and the reflected light from the incident face, and a light interference type spectral element for changing a transmission wavelength at which light is transmitted by means of a lens according to the position of the spectral element at which light is incident on, and in which the spectral element is provided immediately before the photoelectric transfer part array device and a distance between the lens and the light-receiving face of the photoelectric transfer part array device is set so as to substantially agree with a focal distance of the lens so that the light is received from the sample through the lens by the photoelectric transfer part array device; and an arithmetic device for calculating an amount of change in state of polarization of the reflected light from the irradiated light corresponding to the transmission wavelength of the spectral element based upon a received light intensity data which is obtained from each of the photoelectric transfer parts of the photoelectric transfer part array device and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness or film quality, and further, the light-projecting side optical system includes a characterization device for characterizing variations in inclination of the sample around a straight line as a central axis, the line being an intersection between the incident face and a face to be measured, and the arithmetic device includes a received light intensity data correcting device that corrects an error component generated due to variations in inclination of the sample included in the received light intensity data obtained from each of the photoelectric transfer parts, based upon the characteristic of the variations in inclination of the sample detected by the detecting photoelectric transfer device.

19. The spectrometric measuring instrument according to claim 18, wherein the characterization device is a beam shaping device that edge shapes a beam, corresponding to an inclination reference of the sample, in a section contour of the measuring medium light.

20. A spectrometric measuring instrument, which is a measuring instrument for irradiating a sample with measuring medium light to receive a reflected light and detecting a change in state of polarization of the reflected light from the irradiated light, to obtain a film thickness or film quality of the sample, wherein the instrument comprises:

a light-projecting side optical system for applying and condensing the measuring medium light, onto a sample surface;

a light-receiving side optical system, which includes a photoelectric transfer part array device comprising an array of photoelectric transfer parts arrayed in a direction perpendicular to a plane defined by the incoming light to an incident face and the reflected light from the incident face, and a light interference type spectral element for changing a transmission wavelength at which light is transmitted by means of a lens according to the position of the spectral element at which light is incident on, and in which the spectral element is provided immediately before the photoelectric transfer part array device and a distance between the lens and the light-receiving face of the photoelectric transfer part array device is set so as to substantially agree with a focal distance of the lens so that the light is received from the sample through the lens by the photoelectric transfer part array device; and an arithmetic device for calculating an amount of change in state of polarization of the reflected light from the irradiated light corresponding to the transmission wavelength of the spectral element based upon a received light intensity data which is obtained from each of the photoelectric transfer parts of the photoelectric transfer part array device and analyzing the result of the correspondence to obtain a measured spectrometric waveform, while theoretically calculating a theoretical spectrometric waveform from an assumed film thickness and/or film quality, to perform fitting of the measured spectrometric waveform to the theoretical spectrometric waveform so as to obtain a film thickness or film quality, and further, the light-projecting side optical system includes a first characterization device for characterizing variations in inclination of the sample around a straight line as a central axis, the line being perpendicular to the incident face of the measured medium light, and further includes a second characterization device for characterizing variations in inclination of the sample around a straight line as a central axis, the line being an intersection between the incident face and a face to be measured, the light-receiving side optical system includes an inclination detecting photoelectric transfer device that receives the reflected light of the measuring medium light from a film-thickness measuring point of the sample, to detect a characteristic in the first characterization device included in the received reflected light, and further, a distance between the lens and the inclination detecting photoelectric transfer device, which are included in the light-receiving side optical system, is set so as to almost agree with a focal distance of the lens, and the arithmetic device includes a received light intensity data correcting device that corrects an error component generated due to variations in inclination of the sample included in the received light intensity data obtained from each of the photoelectric transfer parts, based upon the characteristic of the variations in inclination of the sample detected by the detecting photoelectric transfer device, and further includes a received light intensity data correcting device that corrects an error component generated due to variations in inclination of the sample included in the received light intensity data obtained from each of the photoelectric transfer parts, based upon the characteristic of the variations in inclination of the sample detected by the inclination detecting photoelectric transfer device.

21. The spectrometric measuring instrument according to claim 20, wherein the characterization device is a beam shaping device that edge shapes a beam, corresponding to an inclination reference of the sample, in a section contour of the measuring medium light.

22. The spectrometric measuring instrument according to claim 21, wherein the beam shaping device at least includes a slit, an aperture, or a knife edge.

* * * * *